US006489542B1

(12) United States Patent
Corbin et al.

(10) Patent No.: US 6,489,542 B1
(45) Date of Patent: Dec. 3, 2002

(54) METHODS FOR TRANSFORMING PLANTS TO EXPRESS CRY2AB δ-ENDOTOXINS TARGETED TO THE PLASTIDS

(75) Inventors: David R. Corbin, Chesterfield, MO (US); Charles P. Romano, Medfield, MA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/186,002

(22) Filed: Nov. 4, 1998

(51) Int. Cl.$^7$ ............................ A01H 5/00; A01H 5/10; C12N 5/14; C12N 15/32; C12N 15/82

(52) U.S. Cl. .................... 800/302; 435/419; 536/23.71; 800/279; 800/320.1

(58) Field of Search ............................ 435/69.1, 320.1, 435/419, 468; 536/23.71, 24.1; 800/279, 302, 320.1, 320.2, 320.3, 320, 314, 312, 317.2, 317.4, 317.3, 316, 306

(56) References Cited

U.S. PATENT DOCUMENTS

| | | | |
|---|---|---|---|
| 5,338,544 | A | 8/1994 | Donovan |
| 5,378,619 | A | 1/1995 | Rogers |
| 5,500,365 | A | 3/1996 | Fischhoff et al. |
| 5,689,052 | A | 11/1997 | Brown et al. |

FOREIGN PATENT DOCUMENTS

| | | |
|---|---|---|
| EP | 385 962 | 9/1990 |
| WO | WO 95/24492 | 9/1995 |

OTHER PUBLICATIONS

Stam M, et al. "The silence of genes in transgenic plants." Ann. Bot. 79: 3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

Crickmore et al., Revision of the Nomenclature for the *Bacillus thuringiensis* Pesticidal Crystal Proteins, *Microbiology and Molecular Biology Reviews 62*:807–813 (1998).

Armstrong et al., Plant Cell Rep. 9:335–339, 1990.

Diehn et al., Genetic Engineering; J.K Setlow, Ed., Plenum Press (New York, NY), vol. 18, p. 83–99, (1996).

Kay et al., Science, 236:1299–1302, 1987.

Koziel et al., Bio/Technology, 11:194–200, 1993.

MacIntosh et al., J. Invert. Pathol., 56:258–266, 1990.

McGaughey et al., Science, 258:1451–1455, 1993.

Perlak et al., Bio/Technology, 8:939–943, 1990.

Perlak et al., Plant Mol. Biol., 22:313–321, 1993.

Roush, Biocontrol Sci. Technol., 4:501–516, 1994.

Widner et al., J. Bacteriol., 171:965–974, 1989.

Widner et al. (a), J. Bacteriol., 172:2826–2832, 1990.

Wong et al., Plant Mol. Biol., 20:81–93, 1992.

Kota et al., Overexpression of the *Bacillus thuringiensis* (Bt) Cry2Aa2 protein in chloroplasts confers resistance to plants against susceptible and Bt–resistant insects; PNAS,USA 96:1840–1845 (Mar. 1999).

* cited by examiner

*Primary Examiner*—Amy J. Nelson
(74) *Attorney, Agent, or Firm*—Timothy K. Ball; Dennis R. Hoerner, Jr.

(57) ABSTRACT

Disclosed is a means of controlling plant pests by a novel method of expressing Cry2Ab *B. thuringiensis* δ-endotoxins in plants, targeted to the plastids. The invention comprises novel nucleic acid segments encoding proteins comprising Cry2Ab *B. thuringiensis* δ-endotoxins. The nucleic acid segments are disclosed, as are transformation vectors containing the nucleic acid segments, plants transformed with the claimed segments, methods for transforming plants, and methods of controlling plant infestation by pests.

63 Claims, 7 Drawing Sheets

Monocot plant cry2Ab expression vectors

Figure 1:
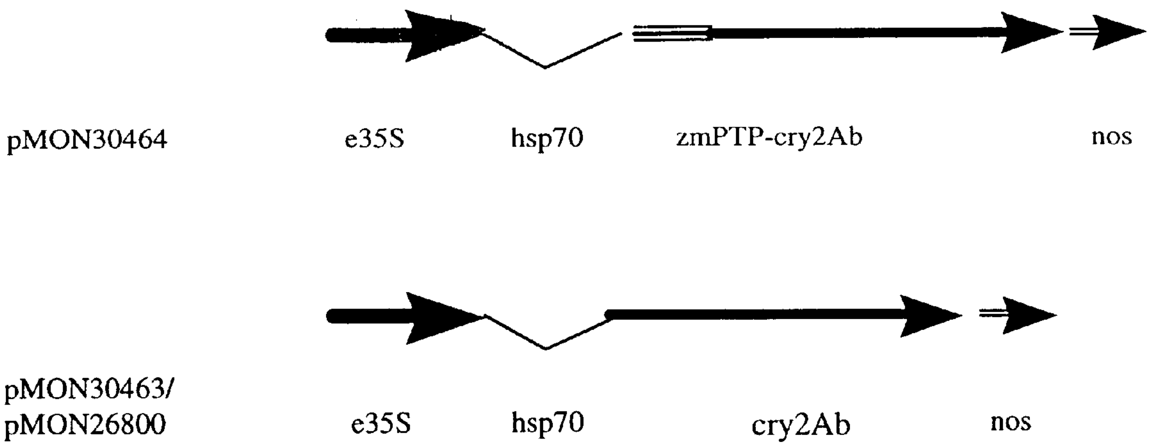

Dicot plant cry2Ab expression vectors.

Dicot plant cry2Aa expression vectors

| | | | | | |
|---|---|---|---|---|---|
| pMON33803 | FMV | hsp70 | | Cry2Aa | E9 |
| | | | | | |
| pMON33812 | FMV | hsp70 | PTP1 | Cry2Aa | E9 |
| pMON33811 | FMV | hsp70 | PTP1 Δ | Cry2Aa | E9 |
| pMON33806 | FMV | hsp70 | PTP2 | Cry2Aa | E9 |

SEQUENCE LISTING

<160> NUMBER OF SEQ ID NOS: 18

<210> SEQ ID NO 1
<211> LENGTH: 1934
<212> TYPE: DNA
<213> ORGANISM: Artificial Sequence
<220> FEATURE:
<223> OTHER INFORMATION: Completely Synthesized

<400> SEQUENCE: 1

```
ccatggacaa ctccgtcctg aactctggtc gcaccaccat ctgcgacgcc tacaacgtcg     60
cggcgcatga tccattcagc ttccagcaca agagcctcga cactgttcag aaggagtgga    120
cggagtggaa gaagaacaac cacagcctgt acctggaccc catcgtcggc acggtggcca    180
gcttccttct caagaaggtc ggctctctcg tcgggaagcg catcctctcg gaactccgca    240
acctgatctt tccatctggc tccaccaacc tcatgcaaga catcctcagg gagaccgaga    300
agtttctcaa ccagcgcctc aacactgata cccttgctcg cgtcaacgct gagctgacgg    360
gtctgcaagc aaacgtggag gagttcaacc gccaagtgga caacttcctc aaccccaacc    420
gcaatgcggt gcctctgtcc atcacttctt ccgtgaacac catgcaacaa ctgttcctca    480
accgcttgcc tcagttccag atgcaaggct accagctgct cctgctgcca ctctttgctc    540
aggctgccaa cctgcacctc tccttcattc gtgacgtgat cctcaacgct gacgagtggg    600
gcatctctgc agccacgctg aggacctacc gcgactacct gaagaactac accagggact    660
actccaacta ttgcatcaac acctaccagt cggccttcaa gggcctcaat acgaggcttc    720
acgacatgct ggagttcagg acctacatgt tcctgaacgt gttcgagtac gtcagcatct    780
ggtcgctctt caagtaccag agcctgctgg tgtccagcgg cgccaacctc tacgccagcg    840
gctctggtcc ccaacaaact cagagcttca ccagccagga ctggccattc ctgtattcgt    900
tgttccaagt caactccaac tacgtcctca acggcttctc tggtgctcgc ctctccaaca    960
ccttccccaa cattgttggc ctccccggct ccaccacaac tcatgctctg cttgctgcca   1020
gagtgaacta ctccggcggc atctcgagcg gcgacattgg tgcatcgccg ttcaaccaga   1080
acttcaactg ctccaccttc ctgccgccgc tgctcacccc gttcgtgagg tcctggctcg   1140
acagcggctc cgaccgcgag ggcgtggcca ccgtcaccaa ctggcaaacc gagtccttcg   1200
agaccaccct tggcctccgg agcggcgcct tcacggcgcg tgggaattct aactacttcc   1260
ccgactactt catcaggaac atctctggtg ttcctctcgt cgtccgcaac gaggacctcc   1320
gccgtccact gcactacaac gagatcagga acatcgcctc tccgtccggg acgcccggag   1380
gtgcaagggc gtacatggtg agcgtccata acaggaagaa caacatccac gctgtgcatg   1440
agaacggctc catgatccac ctggcgccca atgattacac cggcttcacc atctctccaa   1500
tccacgccac ccaagtgaac aaccagacac gcaccttcat ctccgagaag ttcggcaacc   1560
agggcgactc cctgaggttc gagcagaaca acaccaccgc caggtacacc ctgcgcggca   1620
acggcaacag ctacaacctg tacctgcgcg tcagctccat tggcaactcc accatcaggg   1680
tcaccatcaa cgggagggtg tacacagcca ccaatgtgaa cacgacgacc aacaatgatg   1740
gcgtcaacga caacggcgcc cgcttcagcg acatcaacat tggcaacgtg gtggccagca   1800
```

-continued gcaactccga cgtcccgctg gacatcaacg tgaccctgaa ctctggcacc cagttcgacc 1860
tcatgaacat catgctggtg ccaactaaca tctcgccgct gtactgatag gagctctgat 1920
ccccatggga attc 1934

<210> SEQ ID NO 2
<211> LENGTH: 634
<212> TYPE: PRT
<213> ORGANISM: Bacillus thuringiensis

<400> SEQUENCE: 2

```
Met Asp Asn Ser Val Leu Asn Ser Gly Arg Thr Thr Ile Cys Asp Ala
  1               5                  10                  15

Tyr Asn Val Ala Ala His Asp Pro Phe Ser Phe Gln His Lys Ser Leu
             20                  25                  30

Asp Thr Val Gln Lys Glu Trp Thr Glu Trp Lys Lys Asn Asn His Ser
         35                  40                  45

Leu Tyr Leu Asp Pro Ile Val Gly Thr Val Ala Ser Phe Leu Leu Lys
     50                  55                  60

Lys Val Gly Ser Leu Val Gly Lys Arg Ile Leu Ser Glu Leu Arg Asn
 65                  70                  75                  80

Leu Ile Phe Pro Ser Gly Ser Thr Asn Leu Met Gln Asp Ile Leu Arg
                 85                  90                  95

Glu Thr Glu Lys Phe Leu Asn Gln Arg Leu Asn Thr Asp Thr Leu Ala
            100                 105                 110

Arg Val Asn Ala Glu Leu Thr Gly Leu Gln Ala Asn Val Glu Glu Phe
        115                 120                 125

Asn Arg Gln Val Asp Asn Phe Leu Asn Pro Asn Arg Asn Ala Val Pro
    130                 135                 140

Leu Ser Ile Thr Ser Ser Val Asn Thr Met Gln Gln Leu Phe Leu Asn
145                 150                 155                 160

Arg Leu Pro Gln Phe Gln Met Gln Gly Tyr Gln Leu Leu Leu Leu Pro
                165                 170                 175

Leu Phe Ala Gln Ala Ala Asn Leu His Leu Ser Phe Ile Arg Asp Val
            180                 185                 190

Ile Leu Asn Ala Asp Glu Trp Gly Ile Ser Ala Ala Thr Leu Arg Thr
        195                 200                 205

Tyr Arg Asp Tyr Leu Lys Asn Tyr Thr Arg Asp Tyr Ser Asn Tyr Cys
    210                 215                 220

Ile Asn Thr Tyr Gln Ser Ala Phe Lys Gly Leu Asn Thr Arg Leu His
225                 230                 235                 240

Asp Met Leu Glu Phe Arg Thr Tyr Met Phe Leu Asn Val Phe Glu Tyr
                245                 250                 255

Val Ser Ile Trp Ser Leu Phe Lys Tyr Gln Ser Leu Leu Val Ser Ser
            260                 265                 270

Gly Ala Asn Leu Tyr Ala Ser Gly Ser Gly Pro Gln Gln Thr Gln Ser
        275                 280                 285

Phe Thr Ser Gln Asp Trp Pro Phe Leu Tyr Ser Leu Phe Gln Val Asn
    290                 295                 300

Ser Asn Tyr Val Leu Asn Gly Phe Ser Gly Ala Arg Leu Ser Asn Thr
305                 310                 315                 320

Phe Pro Asn Ile Val Gly Leu Pro Gly Ser Thr Thr Thr His Ala Leu
                325                 330                 335

Leu Ala Ala Arg Val Asn Tyr Ser Gly Gly Ile Ser Ser Gly Asp Ile
```

-continued

```
            340                 345                 350

Gly Ala Ser Pro Phe Asn Gln Asn Phe Asn Cys Ser Thr Phe Leu Pro
        355                 360                 365

Pro Leu Leu Thr Pro Phe Val Arg Ser Trp Leu Asp Ser Gly Ser Asp
    370                 375                 380

Arg Glu Gly Val Ala Thr Val Thr Asn Trp Gln Thr Glu Ser Phe Glu
385                 390                 395                 400

Thr Thr Leu Gly Leu Arg Ser Gly Ala Phe Thr Ala Arg Gly Asn Ser
                405                 410                 415

Asn Tyr Phe Pro Asp Tyr Phe Ile Arg Asn Ile Ser Gly Val Pro Leu
            420                 425                 430

Val Val Arg Asn Glu Asp Leu Arg Arg Pro Leu His Tyr Asn Glu Ile
        435                 440                 445

Arg Asn Ile Ala Ser Pro Ser Gly Thr Pro Gly Gly Ala Arg Ala Tyr
    450                 455                 460

Met Val Ser Val His Asn Arg Lys Asn Asn Ile His Ala Val His Glu
465                 470                 475                 480

Asn Gly Ser Met Ile His Leu Ala Pro Asn Asp Tyr Thr Gly Phe Thr
                485                 490                 495

Ile Ser Pro Ile His Ala Thr Gln Val Asn Asn Gln Thr Arg Thr Phe
            500                 505                 510

Ile Ser Glu Lys Phe Gly Asn Gln Gly Asp Ser Leu Arg Phe Glu Gln
        515                 520                 525

Asn Asn Thr Thr Ala Arg Tyr Thr Leu Arg Gly Asn Gly Asn Ser Tyr
    530                 535                 540

Asn Leu Tyr Leu Arg Val Ser Ser Ile Gly Asn Ser Thr Ile Arg Val
545                 550                 555                 560

Thr Ile Asn Gly Arg Val Tyr Thr Ala Thr Asn Val Asn Thr Thr Thr
                565                 570                 575

Asn Asn Asp Gly Val Asn Asp Asn Gly Ala Arg Phe Ser Asp Ile Asn
            580                 585                 590

Ile Gly Asn Val Val Ala Ser Ser Asn Ser Asp Val Pro Leu Asp Ile
        595                 600                 605

Asn Val Thr Leu Asn Ser Gly Thr Gln Phe Asp Leu Met Asn Ile Met
    610                 615                 620

Leu Val Pro Thr Asn Ile Ser Pro Leu Tyr
625                 630
```

<210> SEQ ID NO 3
<211> LENGTH: 415
<212> TYPE: DNA
<213> ORGANISM: Zea mays

<400> SEQUENCE: 3

```
tctagaggat cagcatggcg cccaccgtga tgatggcctc gtcggccacc gccgtcgctc     60

cgttcctggg gctcaagtcc accgccagcc tccccgtcgc ccgccgctcc tccagaagcc    120

tcggcaacgt cagcaacggc ggaaggatcc ggtgcatgca ggtaacaaat gcatcctagc    180

tagtagttct ttgcattgca gcagctgcag ctagcgagtt agtaatagga agggaactga    240

tgatccatgc atggactgat gtgtgttgcc catcccatcc catcccattt cccaaacgaa    300

ccgaaaacac cgtactacgt gcaggtgtgg ccctacggca acaagaagtt cgagacgctg    360

tcgtacctgc cgccgctgtc gaccggcggg cgcatccgct gcatgcaggc catgg         415
```

-continued

<210> SEQ ID NO 4
<211> LENGTH: 79
<212> TYPE: PRT
<213> ORGANISM: Zea mays

<400> SEQUENCE: 4

Met Ala Pro Thr Val Met Met Ala Ser Ser Ala Thr Ala Val Ala Pro
1 5 10 15

Phe Leu Gly Leu Lys Ser Thr Ala Ser Leu Pro Val Ala Arg Arg Ser
20 25 30

Ser Arg Ser Leu Gly Asn Val Ser Asn Gly Gly Arg Ile Arg Cys Met
35 40 45

Gln Val Trp Pro Tyr Gly Asn Lys Lys Phe Glu Thr Leu Ser Tyr Leu
50 55 60

Pro Pro Leu Ser Thr Gly Gly Arg Ile Arg Cys Met Gln Ala Met
65 70 75

<210> SEQ ID NO 5
<211> LENGTH: 268
<212> TYPE: DNA
<213> ORGANISM: Artificial Sequence
<220> FEATURE:
<221> NAME/KEY: transit_peptide
<222> LOCATION: (1)..(267)
<223> OTHER INFORMATION: coding sequence for PTP1 comprising an
Arabidopsis thaliana ssRUBISCO (SSU) chloroplast targeting
sequence and sequences coding for the first 24
amino acids of ssRUBISCO (SSU) protein

<400> SEQUENCE: 5
atggcttcct ctatgctctc ttccgctact atggttgcct ctccggctca ggccactatg 60
gtcgctcctt tcaacggact taagtcctcc gctgccttcc cagccacccg caaggctaac 120
aacgacatta cttccatcac aagcaacggc ggaagagtta actgcatgca ggtgtggcct 180
ccgattggaa agaagaagtt tgagactctc tcttaccttc ctgaccttac cgattccggt 240
ggtcgcgtca actgcatgca ggccatgg 268

<210> SEQ ID NO 6
<211> LENGTH: 89
<212> TYPE: PRT
<213> ORGANISM: Arabidopsis thaliana

<400> SEQUENCE: 6

Met Ala Ser Ser Met Leu Ser Ser Ala Thr Met Val Ala Ser Pro Ala
1 5 10 15

Gln Ala Thr Met Val Ala Pro Phe Asn Gly Leu Lys Ser Ser Ala Ala
20 25 30

Phe Pro Ala Thr Arg Lys Ala Asn Asn Asp Ile Thr Ser Ile Thr Ser
35 40 45

Asn Gly Gly Arg Val Asn Cys Met Gln Val Trp Pro Pro Ile Gly Lys
50 55 60

Lys Lys Phe Glu Thr Leu Ser Tyr Leu Pro Asp Leu Thr Asp Ser Gly
65 70 75 80

Gly Arg Val Asn Cys Met Gln Ala Met
85

<210> SEQ ID NO 7
<211> LENGTH: 178
<212> TYPE: DNA
<213> ORGANISM: Arabidopsis thaliana -continued

<400> SEQUENCE: 7
atggcttcct ctatgctctc ttccgctact atggttgcct ctccggctca ggccactatg 60
gtcgctcctt tcaacggact taagtcctcc gctgccttcc cagccacccg caaggctaac 120
aacgacatta cttccatcac aagcaacggc ggaagagtta actgcatgca ggccatgg 178

<210> SEQ ID NO 8
<211> LENGTH: 59
<212> TYPE: PRT
<213> ORGANISM: Arabidopsis thaliana

<400> SEQUENCE: 8

Met Ala Ser Ser Met Leu Ser Ser Ala Thr Met Val Ala Ser Pro Ala
1 5 10 15

Gln Ala Thr Met Val Ala Pro Phe Asn Gly Leu Lys Ser Ser Ala Ala
20 25 30

Phe Pro Ala Thr Arg Lys Ala Asn Asn Asp Ile Thr Ser Ile Thr Ser
35 40 45

Asn Gly Gly Arg Val Asn Cys Met Gln Ala Met
50 55

<210> SEQ ID NO 9
<211> LENGTH: 240
<212> TYPE: DNA
<213> ORGANISM: Arabidopsis thaliana

<400> SEQUENCE: 9
atggcgcaag ttagcagaat ctgcaatggt gtgcagaacc catctcttat ctccaatctc 60
tcgaaatcca gtcaacgcaa atctccctta tcggtttctc tgaagacgca gcagcatcca 120
cgagcttatc cgatttcgtc gtcgtgggga ttgaagaaga gtgggatgac gttaattggc 180
tctgagcttc gtcctcttaa ggtcatgtct tctgtttcca cggcgtgcat gcttgccatg 240

<210> SEQ ID NO 10
<211> LENGTH: 80
<212> TYPE: PRT
<213> ORGANISM: Arabidopsis thaliana

<400> SEQUENCE: 10

Met Ala Gln Val Ser Arg Ile Cys Asn Gly Val Gln Asn Pro Ser Leu
1 5 10 15

Ile Ser Asn Leu Ser Lys Ser Ser Gln Arg Lys Ser Pro Leu Ser Val
20 25 30

Ser Leu Lys Thr Gln Gln His Pro Arg Ala Tyr Pro Ile Ser Ser Ser
35 40 45

Trp Gly Leu Lys Lys Ser Gly Met Thr Leu Ile Gly Ser Glu Leu Arg
50 55 60

Pro Leu Lys Val Met Ser Ser Val Ser Thr Ala Cys Met Leu Ala Met
65 70 75 80

<210> SEQ ID NO 11
<211> LENGTH: 1907
<212> TYPE: DNA
<213> ORGANISM: Artificial Sequence
<220> FEATURE:
<223> OTHER INFORMATION: completely synthsized

<400> SEQUENCE: 11
ccatggacaa caacgtcttg aactctggta gaacaaccat ctgcgacgca tacaacgtcg 60

-continued

```
tggctcacga tccattcagc ttcgaacaca agagcctcga cactattcag aaggagtgga    120

tggaatggaa acgtactgac cactctctct acgtcgcacc tgtggttgga acagtgtcca    180

gcttccttct caagaaggtc ggctctctca tcggaaaacg tatcttgtcc gaactctggg    240

gtatcatctt tccatctggg tccactaatc tcatgcaaga catcttgagg gagaccgaac    300

agtttctcaa ccagcgtctc aacactgata ccttggctag agtcaacgct gagttgatcg    360

gtctccaagc aaacattcgt gagttcaacc agcaagtgga caacttcttg aatccaactc    420

agaatcctgt gcctctttcc atcacttctt ccgtgaacac tatgcagcaa ctcttcctca    480

acagattgcc tcagtttcag attcaaggct accagttgct ccttcttcca ctctttgctc    540

aggctgccaa catgcacttg tccttcatac gtgacgtgat cctcaacgct gacgaatggg    600

gaatctctgc agccactctt aggacataca gagactactt gaggaactac actcgtgatt    660

actccaacta ttgcatcaac acttatcaga ctgcctttcg tggactcaat actaggcttc    720

acgacatgct tgagttcagg acctacatgt tccttaacgt gtttgagtac gtcagcattt    780

ggagtctctt caagtaccag agcttgatgg tgtcctctgg agccaatctc tacgcctctg    840

gcagtggacc acagcaaact cagagcttca cagctcagaa ctggccattc ttgtatagct    900

tgttccaagt caactccaac tacattctca gtggtatctc tgggaccaga ctctccataa    960

cctttcccaa cattggtgga cttccaggct ccactacaac ccatagcctt aactctgcca   1020

gagtgaacta cagtggaggt gtcagctctg gattgattgg tgcaactaac ttgaaccaca   1080

acttcaattg ctccaccgtc ttgccacctc tgagcacacc gtttgtgagg tcctggcttg   1140

acagcggtac tgatcgcgaa ggagttgcta cctctacaaa ctggcaaacc gagtccttcc   1200

aaaccactct tagccttcgg tgtggagctt tctctgcacg tgggaattca aactactttc   1260

cagactactt cattaggaac atctctggtg ttcctctcgt catcaggaat gaagacctca   1320

cccgtccact tcattacaac cagattagga acatcgagtc tccatccggt actccaggag   1380

gtgcaagagc ttacctcgtg tctgtccata acaggaagaa caacatctac gctgccaacg   1440

agaatggcac catgattcac cttgcaccag aagattacac tggattcacc atctctccaa   1500

tccatgctac ccaagtgaac aatcagacac gcaccttcat ctccgaaaag ttcggaaatc   1560

aaggtgactc cttgaggttc gagcaatcca acactaccgc taggtacact ttgagaggca   1620

atggaaacag ctacaacctt tacttgagag ttagctccat tggtaactcc accatccgtg   1680

ttaccatcaa cggacgtgtt tacacagtct ctaatgtgaa cactacaacg aacaatgatg   1740

gcgttaacga caacggagcc agattcagcg acatcaacat tggcaacatc gtggcctctg   1800

acaacactaa cgttactttg gacatcaatg tgaccctcaa ttctggaact ccatttgatc   1860

tcatgaacat catgtttgtg ccaactaacc tccctccatt gtactaa                 1907
```

<210> SEQ ID NO 12
<211> LENGTH: 634
<212> TYPE: PRT
<213> ORGANISM: Bacillus thuringiensis

<400> SEQUENCE: 12

```
Met Asp Asn Asn Val Leu Asn Ser Gly Arg Thr Thr Ile Cys Asp Ala
  1               5                  10                  15

Tyr Asn Val Val Ala His Asp Pro Phe Ser Phe Glu His Lys Ser Leu
             20                  25                  30

Asp Thr Ile Gln Lys Glu Trp Met Glu Trp Lys Arg Thr Asp His Ser
         35                  40                  45
```

-continued

```
Leu Tyr Val Ala Pro Val Val Gly Thr Val Ser Ser Phe Leu Leu Lys
     50                  55                  60

Lys Val Gly Ser Leu Ile Gly Lys Arg Ile Leu Ser Glu Leu Trp Gly
 65                  70                  75                  80

Ile Ile Phe Pro Ser Gly Ser Thr Asn Leu Met Gln Asp Ile Leu Arg
                 85                  90                  95

Glu Thr Glu Gln Phe Leu Asn Gln Arg Leu Asn Thr Asp Thr Leu Ala
            100                 105                 110

Arg Val Asn Ala Glu Leu Ile Gly Leu Gln Ala Asn Ile Arg Glu Phe
        115                 120                 125

Asn Gln Gln Val Asp Asn Phe Leu Asn Pro Thr Gln Asn Pro Val Pro
    130                 135                 140

Leu Ser Ile Thr Ser Ser Val Asn Thr Met Gln Gln Leu Phe Leu Asn
145                 150                 155                 160

Arg Leu Pro Gln Phe Gln Ile Gln Gly Tyr Gln Leu Leu Leu Leu Pro
                165                 170                 175

Leu Phe Ala Gln Ala Ala Asn Met His Leu Ser Phe Ile Arg Asp Val
            180                 185                 190

Ile Leu Asn Ala Asp Glu Trp Gly Ile Ser Ala Ala Thr Leu Arg Thr
        195                 200                 205

Tyr Arg Asp Tyr Leu Arg Asn Tyr Thr Arg Asp Tyr Ser Asn Tyr Cys
    210                 215                 220

Ile Asn Thr Tyr Gln Thr Ala Phe Arg Gly Leu Asn Thr Arg Leu His
225                 230                 235                 240

Asp Met Leu Glu Phe Arg Thr Tyr Met Phe Leu Asn Val Phe Glu Tyr
                245                 250                 255

Val Ser Ile Trp Ser Leu Phe Lys Tyr Gln Ser Leu Met Val Ser Ser
            260                 265                 270

Gly Ala Asn Leu Tyr Ala Ser Gly Ser Gly Pro Gln Gln Thr Gln Ser
        275                 280                 285

Phe Thr Ala Gln Asn Trp Pro Phe Leu Tyr Ser Leu Phe Gln Val Asn
    290                 295                 300

Ser Asn Tyr Ile Leu Ser Gly Ile Ser Gly Thr Arg Leu Ser Ile Thr
305                 310                 315                 320

Phe Pro Asn Ile Gly Gly Leu Pro Gly Ser Thr Thr Thr His Ser Leu
                325                 330                 335

Asn Ser Ala Arg Val Asn Tyr Ser Gly Gly Val Ser Ser Gly Leu Ile
            340                 345                 350

Gly Ala Thr Asn Leu Asn His Asn Phe Asn Cys Ser Thr Val Leu Pro
        355                 360                 365

Pro Leu Ser Thr Pro Phe Val Arg Ser Trp Leu Asp Ser Gly Thr Asp
    370                 375                 380

Arg Glu Gly Val Ala Thr Ser Thr Asn Trp Gln Thr Glu Ser Phe Gln
385                 390                 395                 400

Thr Thr Leu Ser Leu Arg Cys Gly Ala Phe Ser Ala Arg Gly Asn Ser
                405                 410                 415

Asn Tyr Phe Pro Asp Tyr Phe Ile Arg Asn Ile Ser Gly Val Pro Leu
            420                 425                 430

Val Ile Arg Asn Glu Asp Leu Thr Arg Pro Leu His Tyr Asn Gln Ile
        435                 440                 445

Arg Asn Ile Glu Ser Pro Ser Gly Thr Pro Gly Gly Ala Arg Ala Tyr
    450                 455                 460

Leu Val Ser Val His Asn Arg Lys Asn Asn Ile Tyr Ala Ala Asn Glu
```

-continued 465 470 475 480

Asn Gly Thr Met Ile His Leu Ala Pro Glu Asp Tyr Thr Gly Phe Thr
485 490 495

Ile Ser Pro Ile His Ala Thr Gln Val Asn Asn Gln Thr Arg Thr Phe
500 505 510

Ile Ser Glu Lys Phe Gly Asn Gln Gly Asp Ser Leu Arg Phe Glu Gln
515 520 525

Ser Asn Thr Thr Ala Arg Tyr Thr Leu Arg Gly Asn Gly Asn Ser Tyr
530 535 540

Asn Leu Tyr Leu Arg Val Ser Ser Ile Gly Asn Ser Thr Ile Arg Val
545 550 555 560

Thr Ile Asn Gly Arg Val Tyr Thr Val Ser Asn Val Asn Thr Thr Thr
565 570 575

Asn Asn Asp Gly Val Asn Asp Asn Gly Ala Arg Phe Ser Asp Ile Asn
580 585 590

Ile Gly Asn Ile Val Ala Ser Asp Asn Thr Asn Val Thr Leu Asp Ile
595 600 605

Asn Val Thr Leu Asn Ser Gly Thr Pro Phe Asp Leu Met Asn Ile Met
610 615 620

Phe Val Pro Thr Asn Leu Pro Pro Leu Tyr
625 630

<210> SEQ ID NO 13
<211> LENGTH: 10339
<212> TYPE: DNA
<213> ORGANISM: Artificial Sequence
<220> FEATURE:
<221> NAME/KEY: unsure
<222> LOCATION: (3687)..(3760)
<223> OTHER INFORMATION: "n"=g, a, c, or t
<220> FEATURE:
<221> NAME/KEY: unsure
<222> LOCATION: (4382)..(4434)
<223> OTHER INFORMATION: "n" = g, a, c, or t

<400> SEQUENCE: 13
ggccgcgtta actgcaggtc cgatgtgaga cttttcaaca aagggtaata tccggaaacc 60
tcctcggatt ccattgccca gctatctgtc actttattgt gaagatagtg gaaaaggaag 120
gtggctccta caaatgccat cattgcgata aaggaaaggc catcgttgaa gatgcctctg 180
ccgacagtgg tcccaaagat ggacccccac ccacgaggag catcgtggaa aaagaagacg 240
ttccaaccac gtcttcaaag caagtggatt gatgtgatgg tccgatgtga gacttttcaa 300
caaagggtaa tatccggaaa cctcctcgga ttccattgcc cagctatctg tcactttatt 360
gtgaagatag tggaaaagga aggtggctcc tacaaatgcc atcattgcga taaaggaaag 420
gccatcgttg aagatgcctc tgccgacagt ggtcccaaag atggaccccc acccacgagg 480
agcatcgtgg aaaaagaaga cgttccaacc acgtcttcaa agcaagtgga ttgatgtgat 540
atctccactg acgtaaggga tgacgcacaa tcccactatc cttcgcaaga cccttcctct 600
atataaggaa gttcatttca tttggagagg acacagaaaa atttgctaca ttgtttcaca 660
aacttcaaat attattcatt tatttgtcag ctttcaaact ctttgtttct tgtttgttga 720
ttgagaatac aatggcttcc tctatgctct cttccgctac tatggttgcc tctccggctc 780
aggccactat ggtcgctcct ttcaacggac ttaagtcctc cgctgccttc ccagccaccc 840
gcaaggctaa caacgacatt acttccatca caagcaacgg cggaagagtt aactgcatgc 900
aggtgtggcc tccgattgga aagaagaagt ttgagactct ctcttacctt cctgacctta 960

-continued

```
ccgattccgg tggtcgcgtc aactgcatgc aggccatgga caactccgtc ctgaactctg   1020
gtcgcaccac catctgcgac gcctacaacg tcgcggcgca tgatccattc agcttccagc   1080
acaagagcct cgacactgtt cagaaggagt ggacggagtg gaagaagaac aaccacagcc   1140
tgtacctgga ccccatcgtc ggcacggtgg ccagcttcct tctcaagaag gtcggctctc   1200
tcgtcgggaa gcgcatcctc tcggaactcc gcaacctgat ctttccatct ggctccacca   1260
acctcatgca agacatcctc agggagaccg agaagtttct caaccagcgc ctcaacactg   1320
ataccttgc tcgcgtcaac gctgagctga cgggtctgca agcaaacgtg gaggagttca   1380
accgccaagt ggacaacttc ctcaacccca accgcaatgc ggtgcctctg tccatcactt   1440
cttccgtgaa caccatgcaa caactgttcc tcaaccgctt gcctcagttc cagatgcaag   1500
gctaccagct gctcctgctg ccactctttg ctcaggctgc caacctgcac ctctccttca   1560
ttcgtgacgt gatcctcaac gctgacgagt ggggcatctc tgcagccacg ctgaggacct   1620
accgcgacta cctgaagaac tacaccaggg actactccaa ctattgcatc aacacctacc   1680
agtcggcctt caagggcctc aatacgaggc ttcacgacat gctggagttc aggacctaca   1740
tgttcctgaa cgtgttcgag tacgtcagca tctggtcgct cttcaagtac cagagcctgc   1800
tggtgtccag cggcgccaac ctctacgcca gcggctctgg tccccaacaa actcagagct   1860
tcaccagcca ggactggcca ttcctgtatt cgttgttcca agtcaactcc aactacgtcc   1920
tcaacggctt ctctggtgct cgcctctcca acaccttccc caacattgtt ggcctccccg   1980
gctccaccac aactcatgct ctgcttgctg ccagagtgaa ctactccggc ggcatctcga   2040
gcggcgacat tggtgcatcg ccgttcaacc agaacttcaa ctgctccacc ttcctgccgc   2100
cgctgctcac cccgttcgtg aggtcctggc tcgacagcgg ctccgaccgc gagggcgtgg   2160
ccaccgtcac caactggcaa accgagtcct tcgagaccac ccttggcctc cggagcggcg   2220
ccttcacggc gcgtgggaat tctaactact tccccgacta cttcatcagg aacatctctg   2280
gtgttcctct cgtcgtccgc aacgaggacc tccgccgtcc actgcactac aacgagatca   2340
ggaacatcgc ctctccgtcc gggacgcccg gaggtgcaag ggcgtacatg gtgagcgtcc   2400
ataacaggaa gaacaacatc cacgctgtgc atgagaacgg ctccatgatc cacctggcgc   2460
ccaatgatta caccggcttc accatctctc caatccacgc cacccaagtg aacaaccaga   2520
cacgcacctt catctccgag aagttcggca accagggcga ctccctgagg ttcgagcaga   2580
acaacaccac cgccaggtac accctgcgcg gcaacggcaa cagctacaac ctgtacctgc   2640
gcgtcagctc cattggcaac tccaccatca gggtcaccat caacgggagg gtgtacacag   2700
ccaccaatgt gaacacgacg accaacaatg atggcgtcaa cgacaacggc gcccgcttca   2760
gcgacatcaa cattggcaac gtggtggcca gcagcaactc cgacgtcccg ctggacatca   2820
acgtgaccct gaactctggc acccagttcg acctcatgaa catcatgctg gtgccaacta   2880
acatctcgcc gctgtactga taggagctct gatccccatg ggaattcccg atcgttcaaa   2940
catttggcaa taaagtttct taagattgaa tcctgttgcc ggtcttgcga tgattatcat   3000
ataatttctg ttgaattacg ttaagcatgt aataattaac atgtaatgca tgacgttatt   3060
tatgagatgg gtttttatga ttagagtccc gcaattatac atttaatacg cgatagaaaa   3120
caaaatatag cgcgcaaact aggataaatt atcgcgcgcg gtgtcatcta tgttactaga   3180
tcggggatat ccccggggcg gccgctcgag tggtggccgc atcgatcgtg aagtttctca   3240
tctaagcccc catttggacg tgaatgtaga cacgtcgaaa taaagatttc cgaattagaa   3300
```

-continued

```
taatttgttt attgctttcg cctataaata cgacggatcg taatttgtcg ttttatcaaa   3360
atgtactttc attttataat aacgctgcgg acatctacat ttttgaattg aaaaaaaatt   3420
ggtaattact ctttctttt ctccatattg accatcatac tcattgctga tccatgtaga   3480
tttcccggac atgaagccat ttacaattga atatatcctg ccgccgctgc cgctttgcac   3540
ccggtggagc ttgcatgttg gtttctacgc agaactgagc cggttaggca gataatttcc   3600
attgagaact gagccatgtg caccttcccc ccaacacggt gagcgacggg gcaacggagt   3660
gatccacatg ggacttttcc tagcttnnnn nnnnnnnnnn nnnnnnnnnn nnnnnnnnnn   3720
nnnnnnnnnn nnnnnnnnnn nnnnnnnnnn nnnnnnnnnn ccgggagggt tcgagaaggg   3780
ggggcacccc ccttcggcgt gcgcggtcac gcgccagggc gcagccctgg ttaaaaacaa   3840
ggtttataaa tattggttta aaagcaggtt aaaagacagg ttagcggtgg ccgaaaaacg   3900
ggcggaaacc cttgcaaatg ctggattttc tgcctgtgga cagcccctca aatgtcaata   3960
ggtgcgcccc tcatctgtca tcactctgcc cctcaagtgt caaggatcgc gcccctcatc   4020
tgtcagtagt cgcgcccctc aagtgtcaat accgcagggc acttatcccc aggcttgtcc   4080
acatcatctg tgggaaactc gcgtaaaatc aggcgttttc gccgatttgc gaggctggcc   4140
agctccacgt cgccggccga aatcgagcct gcccctcatc tgtcaacgcc gcgccgggtg   4200
agtcggcccc tcaagtgtca acgtccgccc ctcatctgtc agtgagggcc aagttttccg   4260
cgtggtatcc acaacgccgg cggccggccg cggtgtctcg cacacggctt cgacggcgtt   4320
tctggcgcgt ttgcagggcc atagacggcc gccagcccag cggcgagggc aaccagcccg   4380
gnnnnnnnnn nnnnnnnnnn nnnnnnnnnn nnnnnnnnnn nnnnnnnnnn nnnngtcgat   4440
cgaccgatgc ccttgagagc cttcaaccca gtcagctcct tccggtgggc gcggggcatg   4500
actatcgtcg ccgcacttat gactgtcttc tttatcatgc aactcgtagg acaggtgccg   4560
gcagcgctct gggtcatttt cggcgaggac cgctttcgct ggagcgcgac gatgatcggc   4620
ctgtcgcttg cggtattcgg aatcttgcac gccctcgctc aagccttcgt cactggtccc   4680
gccaccaaac gtttcggcga gaagcaggcc attatcgccg gcatggcggc cgacgcgctg   4740
ggctacgtct tgctggcgtt cgcgacgcga ggctggatgg ccttccccat tatgattctt   4800
ctcgcttccg gcggcatcgg gatgcccgcg ttgcaggcca tgctgtccag gcaggtagat   4860
gacgaccatc agggacagct tcaaggatcg ctcgcggctc ttaccagcct aacttcgatc   4920
actggaccgc tgatcgtcac ggcgatttat gccgcctcgg cgagcacatg gaacgggttg   4980
gcatggattg taggcgccgc cctatacctt gtctgcctcc ccgcgttgcg tcgcggtgca   5040
tggagccggg ccacctcgac ctgaatggaa gccggcggca cctcgctaac ggattcacca   5100
ctccaagaat tggagccaat caattcttgc ggagaactgt gaatgcgcaa accaaccctt   5160
ggcagaacat atccatcgcg tccgccatct ccagcagccg cacgcggcgc atctcgggca   5220
gcgttgggtc ctggccacgg gtgcgcatga tcgtgctcct gtcgttgagg acccggctag   5280
gctggcgggg ttgccttact ggttagcaga atgaatcacc gatacgcgag cgaacgtgaa   5340
gcgactgctg ctgcaaaacg tctgcgacct gagcaacaac atgaatggtc ttcggtttcc   5400
gtgtttcgta aagtctggaa acgcggaagt cagcgccctg caccattatg ttccggatct   5460
gcatcgcagg atgctgctgg ctaccctgtg gaacacctac atctgtatta acgaagcgct   5520
ggcattgacc ctgagtgatt tttctctggt cccgccgcat ccataccgcc agttgtttac   5580
cctcacaacg ttccagtaac cgggcatgtt catcatcagt aacccgtatc gtgagcatcc   5640
tctctcgttt catcggtatc attaccccca tgaacagaaa ttccccctta cacggaggca   5700
```

-continued

```
tcaagtgacc aaacaggaaa aaaccgccct taacatggcc cgctttatca gaagccagac   5760
attaacgctt ctggagaaac tcaacgagct ggacgcggat gaacaggcag acatctgtga   5820
atcgcttcac gaccacgctg atgagcttta ccgcagctgc ctcgcgcgtt tcggtgatga   5880
cggtgaaaac ctctgacaca tgcagctccc ggagacggtc acagcttgtc tgtaagcgga   5940
tgccgggagc agacaagccc gtcagggcgc gtcagcgggt gttggcgggt gtcggggcgc   6000
agccatgacc cagtcacgta gcgatagcgg agtgtatact ggcttaacta tgcggcatca   6060
gagcagattg tactgagagt gcaccatatg cggtgtgaaa taccgcacag atgcgtaagg   6120
agaaaatacc gcatcaggcg ctcttccgct tcctcgctca ctgactcgct gcgctcggtc   6180
gttcggctgc ggcgagcggt atcagctcac tcaaaggcgg taatacggtt atccacagaa   6240
tcaggggata acgcaggaaa gaacatgtga gcaaaaggcc agcaaaaggc caggaaccgt   6300
aaaaaggccg cgttgctggc gtttttccat aggctccgcc cccctgacga gcatcacaaa   6360
aatcgacgct caagtcagag gtggcgaaac ccgacaggac tataaagata ccaggcgttt   6420
ccccctggaa gctccctcgt gcgctctcct gttccgaccc tgccgcttac cggatacctg   6480
tccgcctttc tcccttcggg aagcgtggcg ctttctcata gctcacgctg taggtatctc   6540
agttcggtgt aggtcgttcg ctccaagctg ggctgtgtgc acgaaccccc cgttcagccc   6600
gaccgctgcg ccttatccgg taactatcgt cttgagtcca acccggtaag acacgactta   6660
tcgccactgg cagcagccac tggtaacagg attagcagag cgaggtatgt aggcggtgct   6720
acagagttct tgaagtggtg gcctaactac ggctacacta gaaggacagt atttggtatc   6780
tgcgctctgc tgaagccagt taccttcgga aaaagagttg gtagctcttg atccggcaaa   6840
caaaccaccg ctggtagcgg tggttttttt gtttgcaagc agcagattac gcgcagaaaa   6900
aaaggatctc aagaagatcc tttgatcttt tctacggggt ctgacgctca gtggaacgaa   6960
aactcacgtt aagggatttt ggtcatgaga ttatcaaaaa ggatcttcac ctagatcctt   7020
ttaaattaaa aatgaagttt taaatcaatc taaagtatat atgagtaaac ttggtctgac   7080
agttaccaat gcttaatcag tgaggcacct atctcagcga tctgtctatt tcgttcatcc   7140
atagttgcct gactccccgt cgtgtagata actacgatac gggagggctt accatctggc   7200
cccagtgctg caatgatacc gcgagaccca cgctcaccgg ctccagattt atcagcaata   7260
aaccagccag ccggaagggc cgagcgcaga agtggtcctg caactttatc cgcctccatc   7320
cagtctatta attgttgccg ggaagctaga gtaagtagtt cgccagttaa tagtttgcgc   7380
aacgttgttg ccattgctgc aggtcgggag cacaggatga cgcctaacaa ttcattcaag   7440
ccgacaccgc ttcgcggcgc ggcttaattc aggagttaaa catcatgagg gaagcggtga   7500
tcgccgaagt atcgactcaa ctatcagagg tagttggcgt catcgagcgc catctcgaac   7560
cgacgttgct ggccgtacat ttgtacggct ccgcagtgga tggcggcctg aagccacaca   7620
gtgatattga tttgctggtt acggtgaccg taaggcttga tgaaacaacg cggcgagctt   7680
tgatcaacga ccttttggaa acttcggctt cccctggaga gagcgagatt ctccgcgctg   7740
tagaagtcac cattgttgtg cacgacgaca tcattccgtg gcgttatcca gctaagcgcg   7800
aactgcaatt tggagaatgg cagcgcaatg acattcttgc aggtatcttc gagccagcca   7860
cgatcgacat tgatctggct atcttgctga caaaagcaag agaacatagc gttgccttgg   7920
taggtccagc ggcggaggaa ctctttgatc cggttcctga acaggatcta tttgaggcgc   7980
taaatgaaac cttaacgcta tggaactcgc cgcccgactg ggctggcgat gagcgaaatg   8040
```

-continued

```
tagtgcttac gttgtcccgc atttggtaca gcgcagtaac cggcaaaatc gcgccgaagg   8100
atgtcgctga agactgggca atggagcgcc tgccggccca gtatcagccc gtcatacttg   8160
aagctaggca ggcttatctt ggacaagaag atcgcttggc ctcgcgcgca gatcagttgg   8220
aagaatttgt tcactacgtg aaaggcgaga tcaccaaggt agtcggcaaa taatgtctaa   8280
caattcgttc aagccgacgc cgcttcgcgg cgcggcttaa ctcaagcgtt agatgctgca   8340
ggcatcgtgg tgtcacgctc gtcgtttggt atggcttcat tcagctccgg ttcccaacga   8400
tcaaggcgag ttacatgatc ccccatgttg tgcaaaaaag cggttagctc cttcggtcct   8460
ccgatcgagg atttttcggc gctgcgctac gtccgckacc gcgttgaggg atcaagccac   8520
agcagcccac tcgacctcta gccgacccag acgagccaag ggatcttttt ggaatgctgc   8580
tccgtcgtca ggctttccga cgtttgggtg gttgaacaga agtcattatc gtacggaatg   8640
ccaagcactc ccgaggggaa ccctgtggtt ggcatgcaca tacaaatgga cgaacggata   8700
aaccttttca cgccctttta aatatccgtt attctaataa acgctctttt ctcttaggtt   8760
tacccgccaa tatatcctgt caaacactga tagtttaaac tgaaggcggg aaacgacaat   8820
ctgatcccca tcaagcttgg tcgagtggaa gctagcttcc cgatcctatc tgtcacttca   8880
tcaaaaggac agtagaaaag gaaggtggca ctacaaatgc catcattgcg ataaaggaaa   8940
ggctatcgtt caagatgcct ctgccgacag tggtcccaaa gatggacccc cacccacgag   9000
gagcatcgtg gaaaaagaag acgttccaac cacgtcttca aagcaagtgg attgatgtga   9060
tacttccact gacgtaaggg atgacgcaca atcccactat ccttcgcaag acccttcctc   9120
tatataagga agttcatttc atttggagag gacacgctga aatcaccagt ctctctctac   9180
aagatcgggg atctctagct agacgatcgt ttcgcatgat tgaacaagat ggattgcacg   9240
caggttctcc ggccgcttgg gtggagaggc tattcggcta tgactgggca caacagacaa   9300
tcggctgctc tgatgccgcc gtgttccggc tgtcagcgca ggggcgcccg gttctttttg   9360
tcaagaccga cctgtccggt gccctgaatg aactgcagga cgaggcagcg cggctatcgt   9420
ggctggccac gacgggcgtt ccttgcgcag ctgtgctcga cgttgtcact gaagcgggaa   9480
gggactggct gctattgggc gaagtgccgg ggcaggatct cctgtcatct caccttgctc   9540
ctgccgagaa agtatccatc atggctgatg caatgcggcg gctgcatacg cttgatccgg   9600
ctacctgccc attcgaccac caagcgaaac atcgcatcga gcgagcacgt actcggatgg   9660
aagccggtct tgtcgatcag gatgatctgg acgaagagca tcaggggctc gcgccagccg   9720
aactgttcgc caggctcaag gcgcgcatgc ccgacggcga ggatctcgtc gtgacccatg   9780
gcgatgcctg cttgccgaat atcatggtgg aaaatggccg cttttctgga ttcatcgact   9840
gtggccggct gggtgtggcg gaccgctatc aggacatagc gttggctacc cgtgatattg   9900
ctgaagagct tggcggcgaa tgggctgacc gcttcctcgt gctttacggt atcgccgctc   9960
ccgattcgca gcgcatcgcc ttctatcgcc ttcttgacga gttcttctga gcgggactct  10020
ggggttcgat ccccaattcc cgatcgttca aacatttggc aataaagttt cttaagattg  10080
aatcctgttg ccggtcttgc gatgattatc atataatttc tgttgaatta cgttaagcat  10140
gtaataatta acatgtaatg catgacgtta tttatgagat gggtttttat gattagagtc  10200
ccgcaattat acatttaata cgcgatagaa aacaaaatat agcgcgcaaa ctaggataaa  10260
ttatcgcgcg cggtgtcatc tatgttacta gatcggggat cgggccactc gaccaagctt  10320
ctgcaggtcc tgctcgagc                                               10339
```

-continued

<210> SEQ ID NO 14
<211> LENGTH: 10249
<212> TYPE: DNA
<213> ORGANISM: Artificial Sequence
<220> FEATURE:
<221> NAME/KEY: unsure
<222> LOCATION: (3597)..(3670)
<223> OTHER INFORMATION: "n" = g, a, c, or t
<220> FEATURE:
<221> NAME/KEY: unsure
<222> LOCATION: (4292)..(4344)
<223> OTHER INFORMATION: "n" = g, a, c, or t

<400> SEQUENCE: 14
ggccgcgtta actgcaggtc cgatgtgaga cttttcaaca aagggtaata tccggaaacc 60
tcctcggatt ccattgccca gctatctgtc actttattgt gaagatagtg gaaaaggaag 120
gtggctccta caaatgccat cattgcgata aaggaaaggc catcgttgaa gatgcctctg 180
ccgacagtgg tcccaaagat ggacccccac ccacgaggag catcgtggaa aaagaagacg 240
ttccaaccac gtcttcaaag caagtggatt gatgtgatgg tccgatgtga gacttttcaa 300
caaagggtaa tatccggaaa cctcctcgga ttccattgcc cagctatctg tcactttatt 360
gtgaagatag tggaaaagga aggtggctcc tacaaatgcc atcattgcga taaaggaaag 420
gccatcgttg aagatgcctc tgccgacagt ggtcccaaag atggaccccc acccacgagg 480
agcatcgtgg aaaaagaaga cgttccaacc acgtcttcaa agcaagtgga ttgatgtgat 540
atctccactg acgtaaggga tgacgcacaa tcccactatc cttcgcaaga cccttcctct 600
atataaggaa gttcatttca tttggagagg acacagaaaa atttgctaca ttgtttcaca 660
aacttcaaat attattcatt tatttgtcag ctttcaaact ctttgtttct tgtttgttga 720
ttgagaatac aatggcttcc tctatgctct cttccgctac tatggttgcc tctccggctc 780
aggccactat ggtcgctcct ttcaacggac ttaagtcctc cgctgccttc ccagccaccc 840
gcaaggctaa caacgacatt acttccatca caagcaacgg cggaagagtt aactgcatgc 900
aggccatgga caactccgtc ctgaactctg gtcgcaccac catctgcgac gcctacaacg 960
tcgcggcgca tgatccattc agcttccagc acaagagcct cgacactgtt cagaaggagt 1020
ggacggagtg gaagaagaac aaccacagcc tgtacctgga ccccatcgtc ggcacggtgg 1080
ccagcttcct tctcaagaag gtcggctctc tcgtcgggaa gcgcatcctc tcggaactcc 1140
gcaacctgat ctttccatct ggctccacca acctcatgca agacatcctc agggagaccg 1200
agaagtttct caaccagcgc ctcaacactg atacccttgc tcgcgtcaac gctgagctga 1260
cgggtctgca agcaaacgtg gaggagttca accgccaagt ggacaacttc ctcaacccca 1320
accgcaatgc ggtgcctctg tccatcactt cttccgtgaa caccatgcaa caactgttcc 1380
tcaaccgctt gcctcagttc cagatgcaag gctaccagct gctcctgctg ccactctttg 1440
ctcaggctgc caacctgcac ctctccttca ttcgtgacgt gatcctcaac gctgacgagt 1500
ggggcatctc tgcagccacg ctgaggacct accgcgacta cctgaagaac tacaccaggg 1560
actactccaa ctattgcatc aacacctacc agtcggcctt caagggcctc aatacgaggc 1620
ttcacgacat gctggagttc aggacctaca tgttcctgaa cgtgttcgag tacgtcagca 1680
tctggtcgct cttcaagtac cagagcctgc tggtgtccag cggcgccaac ctctacgcca 1740
gcggctctgg tccccaacaa actcagagct tcaccagcca ggactggcca ttcctgtatt 1800
cgttgttcca agtcaactcc aactacgtcc tcaacggctt ctctggtgct cgcctctcca 1860
acaccttccc caacattgtt ggcctccccg gctccaccac aactcatgct ctgcttgctg 1920

-continued

```
ccagagtgaa ctactccggc ggcatctcga gcggcgacat tggtgcatcg ccgttcaacc   1980
agaacttcaa ctgctccacc ttcctgccgc cgctgctcac cccgttcgtg aggtcctggc   2040
tcgacagcgg ctccgaccgc gagggcgtgg ccaccgtcac caactggcaa accgagtcct   2100
tcgagaccac ccttggcctc cggagcggcg ccttcacggc gcgtgggaat tctaactact   2160
tccccgacta cttcatcagg aacatctctg gtgttcctct cgtcgtccgc aacgaggacc   2220
tccgccgtcc actgcactac aacgagatca ggaacatcgc ctctccgtcc gggacgcccg   2280
gaggtgcaag ggcgtacatg gtgagcgtcc ataacaggaa gaacaacatc cacgctgtgc   2340
atgagaacgg ctccatgatc cacctggcgc ccaatgatta caccggcttc accatctctc   2400
caatccacgc cacccaagtg aacaaccaga cacgcacctt catctccgag aagttcggca   2460
accagggcga ctccctgagg ttcgagcaga acaacaccac cgccaggtac accctgcgcg   2520
gcaacggcaa cagctacaac ctgtacctgc gcgtcagctc cattggcaac tccaccatca   2580
gggtcaccat caacgggagg gtgtacacag ccaccaatgt gaacacgacg accaacaatg   2640
atggcgtcaa cgacaacggc gcccgcttca gcgacatcaa cattggcaac gtggtggcca   2700
gcagcaactc cgacgtcccg ctggacatca acgtgaccct gaactctggc acccagttcg   2760
acctcatgaa catcatgctg gtgccaacta acatctcgcc gctgtactga taggagctct   2820
gatccccatg ggaattcccg atcgttcaaa catttggcaa taaagtttct taagattgaa   2880
tcctgttgcc ggtcttgcga tgattatcat ataatttctg ttgaattacg ttaagcatgt   2940
aataattaac atgtaatgca tgacgttatt tatgagatgg gtttttatga ttagagtccc   3000
gcaattatac atttaatacg cgatagaaaa caaaatatag cgcgcaaact aggataaatt   3060
atcgcgcgcg gtgtcatcta tgttactaga tcggggatat ccccggggcg gccgctcgag   3120
tggtggccgc atcgatcgtg aagtttctca tctaagcccc catttggacg tgaatgtaga   3180
cacgtcgaaa taaagatttc cgaattagaa taatttgttt attgctttcg cctataaata   3240
cgacggatcg taatttgtcg ttttatcaaa atgtactttc attttataat aacgctgcgg   3300
acatctacat ttttgaattg aaaaaaaatt ggtaattact ctttcttttt ctccatattg   3360
accatcatac tcattgctga tccatgtaga tttcccggac atgaagccat ttacaattga   3420
atatatcctg ccgccgctgc cgctttgcac ccggtggagc ttgcatgttg gtttctacgc   3480
agaactgagc cggttaggca gataatttcc attgagaact gagccatgtg caccttcccc   3540
ccaacacggt gagcgacggg gcaacggagt gatccacatg ggacttttcc tagcttnnnn   3600
nnnnnnnnnn nnnnnnnnnn nnnnnnnnnn nnnnnnnnnn nnnnnnnnnn nnnnnnnnnn   3660
nnnnnnnnnn ccgggagggt tcgagaaggg ggggcacccc ccttcggcgt gcgcggtcac   3720
gcgccagggc gcagccctgg ttaaaaacaa ggtttataaa tattggttta aaagcaggtt   3780
aaaagacagg ttagcggtgg ccgaaaaacg ggcggaaacc cttgcaaatg ctggattttc   3840
tgcctgtgga cagcccctca aatgtcaata ggtgcgcccc tcatctgtca tcactctgcc   3900
cctcaagtgt caaggatcgc gcccctcatc tgtcagtagt cgcgcccctc aagtgtcaat   3960
accgcagggc acttatcccc aggcttgtcc acatcatctg tgggaaactc gcgtaaaatc   4020
aggcgttttc gccgatttgc gaggctggcc agctccacgt cgccggccga aatcgagcct   4080
gcccctcatc tgtcaacgcc gcgccgggtg agtcggcccc tcaagtgtca acgtccgccc   4140
ctcatctgtc agtgagggcc aagttttccg cgtggtatcc acaacgccgg cggccggccg   4200
cggtgtctcg cacacggctt cgacggcgtt tctggcgcgt ttgcagggcc atagacggcc   4260
gccagcccag cggcgagggc aaccagcccg gnnnnnnnnn nnnnnnnnnn nnnnnnnnnn   4320
```

-continued

```
nnnnnnnnnn nnnnnnnnnn nnnngtcgat cgaccgatgc ccttgagagc cttcaaccca   4380
gtcagctcct tccggtgggc gcggggcatg actatcgtcg ccgcacttat gactgtcttc   4440
tttatcatgc aactcgtagg acaggtgccg gcagcgctct gggtcatttt cggcgaggac   4500
cgctttcgct ggagcgcgac gatgatcggc ctgtcgcttg cggtattcgg aatcttgcac   4560
gccctcgctc aagccttcgt cactggtccc gccaccaaac gtttcggcga gaagcaggcc   4620
attatcgccg gcatggcggc cgacgcgctg ggctacgtct tgctggcgtt cgcgacgcga   4680
ggctggatgg ccttccccat tatgattctt ctcgcttccg gcggcatcgg gatgcccgcg   4740
ttgcaggcca tgctgtccag gcaggtagat gacgaccatc agggacagct tcaaggatcg   4800
ctcgcggctc ttaccagcct aacttcgatc actggaccgc tgatcgtcac ggcgatttat   4860
gccgcctcgg cgagcacatg gaacgggttg gcatggattg taggcgccgc cctatacctt   4920
gtctgcctcc ccgcgttgcg tcgcggtgca tggagccggg ccacctcgac ctgaatggaa   4980
gccggcggca cctcgctaac ggattcacca ctccaagaat tggagccaat caattcttgc   5040
ggagaactgt gaatgcgcaa accaaccctt ggcagaacat atccatcgcg tccgccatct   5100
ccagcagccg cacgcggcgc atctcgggca gcgttgggtc ctggccacgg gtgcgcatga   5160
tcgtgctcct gtcgttgagg acccggctag gctggcgggg ttgccttact ggttagcaga   5220
atgaatcacc gatacgcgag cgaacgtgaa gcgactgctg ctgcaaaacg tctgcgacct   5280
gagcaacaac atgaatggtc ttcggtttcc gtgtttcgta aagtctggaa acgcggaagt   5340
cagcgccctg caccattatg ttccggatct gcatcgcagg atgctgctgg ctaccctgtg   5400
gaacacctac atctgtatta acgaagcgct ggcattgacc ctgagtgatt tttctctggt   5460
cccgccgcat ccataccgcc agttgtttac cctcacaacg ttccagtaac cgggcatgtt   5520
catcatcagt aacccgtatc gtgagcatcc tctctcgttt catcggtatc attaccccca   5580
tgaacagaaa ttccccctta cacggaggca tcaagtgacc aaacaggaaa aaaccgccct   5640
taacatggcc cgctttatca gaagccagac attaacgctt ctggagaaac tcaacgagct   5700
ggacgcggat gaacaggcag acatctgtga atcgcttcac gaccacgctg atgagcttta   5760
ccgcagctgc ctcgcgcgtt tcggtgatga cggtgaaaac ctctgacaca tgcagctccc   5820
ggagacggtc acagcttgtc tgtaagcgga tgccgggagc agacaagccc gtcagggcgc   5880
gtcagcgggt gttggcgggt gtcggggcgc agccatgacc cagtcacgta gcgatagcgg   5940
agtgtatact ggcttaacta tgcggcatca gagcagattg tactgagagt gcaccatatg   6000
cggtgtgaaa taccgcacag atgcgtaagg agaaaatacc gcatcaggcg ctcttccgct   6060
tcctcgctca ctgactcgct gcgctcggtc gttcggctgc ggcgagcggt atcagctcac   6120
tcaaaggcgg taatacggtt atccacagaa tcaggggata acgcaggaaa gaacatgtga   6180
gcaaaaggcc agcaaaaggc caggaaccgt aaaaaggccg cgttgctggc gtttttccat   6240
aggctccgcc cccctgacga gcatcacaaa aatcgacgct caagtcagag gtggcgaaac   6300
ccgacaggac tataaagata ccaggcgttt ccccctggaa gctccctcgt gcgctctcct   6360
gttccgaccc tgccgcttac cggatacctg tccgcctttc tcccttcggg aagcgtggcg   6420
ctttctcata gctcacgctg taggtatctc agttcggtgt aggtcgttcg ctccaagctg   6480
ggctgtgtgc acgaaccccc cgttcagccc gaccgctgcg ccttatccgg taactatcgt   6540
cttgagtcca acccggtaag acacgactta tcgccactgg cagcagccac tggtaacagg   6600
attagcagag cgaggtatgt aggcggtgct acagagttct tgaagtggtg gcctaactac   6660
```

-continued

```
ggctacacta gaaggacagt atttggtatc tgcgctctgc tgaagccagt taccttcgga   6720
aaaagagttg gtagctcttg atccggcaaa caaaccaccg ctggtagcgg tggttttttt   6780
gtttgcaagc agcagattac gcgcagaaaa aaaggatctc aagaagatcc tttgatcttt   6840
tctacggggt ctgacgctca gtggaacgaa aactcacgtt aagggatttt ggtcatgaga   6900
ttatcaaaaa ggatcttcac ctagatcctt ttaaattaaa aatgaagttt taaatcaatc   6960
taaagtatat atgagtaaac ttggtctgac agttaccaat gcttaatcag tgaggcacct   7020
atctcagcga tctgtctatt tcgttcatcc atagttgcct gactccccgt cgtgtagata   7080
actacgatac gggagggctt accatctggc cccagtgctg caatgatacc gcgagaccca   7140
cgctcaccgg ctccagattt atcagcaata aaccagccag ccggaagggc cgagcgcaga   7200
agtggtcctg caactttatc cgcctccatc cagtctatta attgttgccg ggaagctaga   7260
gtaagtagtt cgccagttaa tagtttgcgc aacgttgttg ccattgctgc aggtcgggag   7320
cacaggatga cgcctaacaa ttcattcaag ccgacaccgc ttcgcggcgc ggcttaattc   7380
aggagttaaa catcatgagg gaagcggtga tcgccgaagt atcgactcaa ctatcagagg   7440
tagttggcgt catcgagcgc catctcgaac cgacgttgct ggccgtacat ttgtacggct   7500
ccgcagtgga tggcggcctg aagccacaca gtgatattga tttgctggtt acggtgaccg   7560
taaggcttga tgaaacaacg cggcgagctt tgatcaacga ccttttggaa acttcggctt   7620
cccctggaga gagcgagatt ctccgcgctg tagaagtcac cattgttgtg cacgacgaca   7680
tcattccgtg gcgttatcca gctaagcgcg aactgcaatt tggagaatgg cagcgcaatg   7740
acattcttgc aggtatcttc gagccagcca cgatcgacat tgatctggct atcttgctga   7800
caaaagcaag agaacatagc gttgccttgg taggtccagc ggcggaggaa ctctttgatc   7860
cggttcctga acaggatcta tttgaggcgc taaatgaaac cttaacgcta tggaactcgc   7920
cgcccgactg ggctggcgat gagcgaaatg tagtgcttac gttgtcccgc atttggtaca   7980
gcgcagtaac cggcaaaatc gcgccgaagg atgtcgctga agactgggca atggagcgcc   8040
tgccggccca gtatcagccc gtcatacttg aagctaggca ggcttatctt ggacaagaag   8100
atcgcttggc ctcgcgcgca gatcagttgg aagaatttgt tcactacgtg aaaggcgaga   8160
tcaccaaggt agtcggcaaa taatgtctaa caattcgttc aagccgacgc cgcttcgcgg   8220
cgcggcttaa ctcaagcgtt agatgctgca ggcatcgtgg tgtcacgctc gtcgtttggt   8280
atggcttcat tcagctccgg ttcccaacga tcaaggcgag ttacatgatc ccccatgttg   8340
tgcaaaaaag cggttagctc cttcggtcct ccgatcgagg atttttcggc gctgcgctac   8400
gtccgckacc gcgttgaggg atcaagccac agcagcccac tcgacctcta gccgacccag   8460
acgagccaag ggatcttttt ggaatgctgc tccgtcgtca ggctttccga cgtttgggtg   8520
gttgaacaga agtcattatc gtacggaatg ccaagcactc ccgaggggaa ccctgtggtt   8580
ggcatgcaca tacaaatgga cgaacggata aaccttttca cgccctttta aatatccgtt   8640
attctaataa acgctctttt ctcttaggtt tacccgccaa tatatcctgt caaacactga   8700
tagtttaaac tgaaggcggg aaacgacaat ctgatcccca tcaagcttgg tcgagtggaa   8760
gctagcttcc cgatcctatc tgtcacttca tcaaaaggac agtagaaaag gaaggtggca   8820
ctacaaatgc catcattgcg ataaaggaaa ggctatcgtt caagatgcct ctgccgacag   8880
tggtcccaaa gatggacccc cacccacgag gagcatcgtg gaaaaagaag acgttccaac   8940
cacgtcttca aagcaagtgg attgatgtga tacttccact gacgtaaggg atgacgcaca   9000
atcccactat ccttcgcaag acccttcctc tatataagga agttcatttc atttggagag   9060
```

-continued gacacgctga aatcaccagt ctctctctac aagatcgggg atctctagct agacgatcgt 9120
ttcgcatgat tgaacaagat ggattgcacg caggttctcc ggccgcttgg gtggagaggc 9180
tattcggcta tgactgggca caacagacaa tcggctgctc tgatgccgcc gtgttccggc 9240
tgtcagcgca ggggcgcccg gttctttttg tcaagaccga cctgtccggt gccctgaatg 9300
aactgcagga cgaggcagcg cggctatcgt ggctggccac gacgggcgtt ccttgcgcag 9360
ctgtgctcga cgttgtcact gaagcgggaa gggactggct gctattgggc gaagtgccgg 9420
ggcaggatct cctgtcatct caccttgctc ctgccgagaa agtatccatc atggctgatg 9480
caatgcggcg gctgcatacg cttgatccgg ctacctgccc attcgaccac caagcgaaac 9540
atcgcatcga gcgagcacgt actcggatgg aagccggtct tgtcgatcag gatgatctgg 9600
acgaagagca tcaggggctc gcgccagccg aactgttcgc caggctcaag gcgcgcatgc 9660
ccgacggcga ggatctcgtc gtgacccatg gcgatgcctg cttgccgaat atcatggtgg 9720
aaaatggccg cttttctgga ttcatcgact gtggccggct gggtgtggcg gaccgctatc 9780
aggacatagc gttggctacc cgtgatattg ctgaagagct tggcggcgaa tgggctgacc 9840
gcttcctcgt gctttacggt atcgccgctc ccgattcgca gcgcatcgcc ttctatcgcc 9900
ttcttgacga gttcttctga gcgggactct ggggttcgat ccccaattcc cgatcgttca 9960
aacatttggc aataaagttt cttaagattg aatcctgttg ccggtcttgc gatgattatc 10020
atataatttc tgttgaatta cgttaagcat gtaataatta acatgtaatg catgacgtta 10080
tttatgagat gggtttttat gattagagtc ccgcaattat acatttaata cgcgatagaa 10140
aacaaaatat agcgcgcaaa ctaggataaa ttatcgcgcg cggtgtcatc tatgttacta 10200
gatcggggat cgggccactc gaccaagctt ctgcaggtcc tgctcgagc 10249

<210> SEQ ID NO 15
<211> LENGTH: 10252
<212> TYPE: DNA
<213> ORGANISM: Artificial Sequence
<220> FEATURE:
<221> NAME/KEY: unsure
<222> LOCATION: (3660)..(3773)
<223> OTHER INFORMATION: “n” = g, a, c, or t
<220> FEATURE:
<221> NAME/KEY: unsure
<222> LOCATION: (4355)..(4407)
<223> OTHER INFORMATION: “n” = g, a, c, or t

<400> SEQUENCE: 15
tcctcggatt ccattgccca gctatctgtc actttattgt gaagatagtg gaaaaggaag 60
gtggctccta caaatgccat cattgcgata aaggaaaggc catcgttgaa gatgcctctg 120
ccgacagtgg tcccaaagat ggacccccac ccacgaggag catcgtggaa aaagaagacg 180
ttccaaccac gtcttcaaag caagtggatt gatgtgatgg tccgatgtga gacttttcaa 240
caaagggtaa tatccggaaa cctcctcgga ttccattgcc cagctatctg tcactttatt 300
gtgaagatag tggaaaagga aggtggctcc tacaaatgcc atcattgcga taaaggaaag 360
gccatcgttg aagatgcctc tgccgacagt ggtcccaaag atggaccccc acccacgagg 420
agcatcgtgg aaaaagaaga cgttccaacc acgtcttcaa agcaagtgga ttgatgtgat 480
atctccactg acgtaaggga tgacgcacaa tcccactatc cttcgcaaga cccttcctct 540
atataaggaa gttcatttca tttggagagg acacagaaaa atttgctaca ttgtttcaca 600
aacttcaaat attattcatt tatttgtcag ctttcaaact ctttgtttct tgtttgttga 660

-continued

```
ttgagaatac aatggcgcaa gttagcagaa tctgcaatgg tgtgcagaac ccatctctta    720
tctccaatct ctcgaaatcc agtcaacgca aatctccctt atcggtttct ctgaagacgc    780
agcagcatcc acgagcttat ccgatttcgt cgtcgtgggg attgaagaag agtgggatga    840
cgttaattgg ctctgagctt cgtcctctta aggtcatgtc ttctgtttcc acggcgtgca    900
tgcttgccat ggacaactcc gtcctgaact ctggtcgcac caccatctgc gacgcctaca    960
acgtcgcggc gcatgatcca ttcagcttcc agcacaagag cctcgacact gttcagaagg   1020
agtggacgga gtggaagaag aacaaccaca gcctgtacct ggaccccatc gtcggcacgg   1080
tggccagctt ccttctcaag aaggtcggct ctctcgtcgg gaagcgcatc ctctcggaac   1140
tccgcaacct gatctttcca tctggctcca ccaacctcat gcaagacatc ctcagggaga   1200
ccgagaagtt tctcaaccag cgcctcaaca ctgataccct tgctcgcgtc aacgctgagc   1260
tgacgggtct gcaagcaaac gtggaggagt tcaaccgcca agtggacaac ttcctcaacc   1320
ccaaccgcaa tgcggtgcct ctgtccatca cttcttccgt gaacaccatg caacaactgt   1380
tcctcaaccg cttgcctcag ttccagatgc aaggctacca gctgctcctg ctgccactct   1440
ttgctcaggc tgccaacctg cacctctcct tcattcgtga cgtgatcctc aacgctgacg   1500
agtggggcat ctctgcagcc acgctgagga cctaccgcga ctacctgaag aactacacca   1560
gggactactc caactattgc atcaacacct accagtcggc cttcaagggc ctcaatacga   1620
ggcttcacga catgctggag ttcaggacct acatgttcct gaacgtgttc gagtacgtca   1680
gcatctggtc gctcttcaag taccagagcc tgctggtgtc cagcggcgcc aacctctacg   1740
ccagcggctc tggtccccaa caaactcaga gcttcaccag ccaggactgg ccattcctgt   1800
attcgttgtt ccaagtcaac tccaactacg tcctcaacgg cttctctggt gctcgcctct   1860
ccaacacctt ccccaacatt gttggcctcc ccggctccac cacaactcat gctctgcttg   1920
ctgccagagt gaactactcc ggcggcatct cgagcggcga cattggtgca tcgccgttca   1980
accagaactt caactgctcc accttcctgc cgccgctgct caccccgttc gtgaggtcct   2040
ggctcgacag cggctccgac cgcgagggcg tggccaccgt caccaactgg caaaccgagt   2100
ccttcgagac cacccttggc ctccggagcg gcgccttcac ggcgcgtggg aattctaact   2160
acttccccga ctacttcatc aggaacatct ctggtgttcc tctcgtcgtc cgcaacgagg   2220
acctccgccg tccactgcac tacaacgaga tcaggaacat cgcctctccg tccgggacgc   2280
ccggaggtgc aagggcgtac atggtgagcg tccataacag gaagaacaac atccacgctg   2340
tgcatgagaa cggctccatg atccacctgg cgcccaatga ttacaccggc ttcaccatct   2400
ctccaatcca cgccacccaa gtgaacaacc agacacgcac cttcatctcc gagaagttcg   2460
gcaaccaggg cgactccctg aggttcgagc agaacaacac caccgccagg tacaccctgc   2520
gcggcaacgg caacagctac aacctgtacc tgcgcgtcag ctccattggc aactccacca   2580
tcagggtcac catcaacggg agggtgtaca cagccaccaa tgtgaacacg acgaccaaca   2640
atgatggcgt caacgacaac ggcgcccgct tcagcgacat caacattggc aacgtggtgg   2700
ccagcagcaa ctccgacgtc ccgctggaca tcaacgtgac cctgaactct ggcacccagt   2760
tcgacctcat gaacatcatg ctggtgccaa ctaacatctc gccgctgtac tgataggagc   2820
tctgatcccc atgggaattc ccgatcgttc aaacatttgg caataaagtt tcttaagatt   2880
gaatcctgtt gccggtcttg cgatgattat catataattt ctgttgaatt acgttaagca   2940
tgtaataatt aacatgtaat gcatgacgtt atttatgaga tgggttttta tgattagagt   3000
cccgcaatta tacatttaat acgcgataga aaacaaaata tagcgcgcaa actaggataa   3060
```

-continued

```
attatcgcgc gcggtgtcat ctatgttact agatcgggga tatccccggg gcggccgctc   3120
gagtggtggc cgcatcgatc gtgaagtttc tcatctaagc cccatttgg acgtgaatgt   3180
agacacgtcg aaataaagat ttccgaatta gaataatttg tttattgctt tcgcctataa   3240
atacgacgga tcgtaatttg tcgttttatc aaaatgtact ttcattttat aataacgctg   3300
cggacatcta catttttgaa ttgaaaaaaa attggtaatt actctttctt tttctccata   3360
ttgaccatca tactcattgc tgatccatgt agatttcccg gacatgaagc catttacaat   3420
tgaatatatc ctgccgccgc tgccgctttg cacccggtgg agcttgcatg ttggtttcta   3480
cgcagaactg agccggttag gcagataatt tccattgaga actgagccat gtgcaccttc   3540
cccccaacac ggtgagcgac ggggcaacgg agtgatccac atgggacttt tcctagcttn   3600
nnnnnnnnnn nnnnnnnnnn nnnnnnnnnn nnnnnnnnnn nnnnnnnnnn nnnnnnnnnn   3660
nnnnnnnnnn nnnccgggag ggttcgagaa gggggggcac ccccttcgg cgtgcgcggt   3720
cacgcgccag ggcgcagccc tggttaaaaa caaggtttat aaatattggt ttaaaagcag   3780
gttaaaagac aggttagcgg tggccgaaaa acgggcggaa acccttgcaa atgctggatt   3840
ttctgcctgt ggacagcccc tcaaatgtca ataggtgcgc ccctcatctg tcatcactct   3900
gcccctcaag tgtcaaggat cgcgcccctc atctgtcagt agtcgcgccc ctcaagtgtc   3960
aataccgcag ggcacttatc cccaggcttg tccacatcat ctgtgggaaa ctcgcgtaaa   4020
atcaggcgtt ttcgccgatt tgcgaggctg gccagctcca cgtcgccggc cgaaatcgag   4080
cctgcccctc atctgtcaac gccgcgccgg gtgagtcggc ccctcaagtg tcaacgtccg   4140
cccctcatct gtcagtgagg gccaagtttt ccgcgtggta tccacaacgc cggcggccgg   4200
ccgcggtgtc tcgcacacgg cttcgacggc gtttctggcg cgtttgcagg gccatagacg   4260
gccgccagcc cagcggcgag ggcaaccagc ccggnnnnnn nnnnnnnnnn nnnnnnnnnn   4320
nnnnnnnnnn nnnnnnnnnn nnnnnnngtc gatcgaccga tgcccttgag agccttcaac   4380
ccagtcagct ccttccggtg ggcgcggggc atgactatcg tcgccgcact tatgactgtc   4440
ttctttatca tgcaactcgt aggacaggtg ccggcagcgc tctgggtcat tttcggcgag   4500
gaccgctttc gctggagcgc gacgatgatc ggcctgtcgc ttgcggtatt cggaatcttg   4560
cacgccctcg ctcaagcctt cgtcactggt cccgccacca aacgtttcgg cgagaagcag   4620
gccattatcg ccggcatggc ggccgacgcg ctgggctacg tcttgctggc gttcgcgacg   4680
cgaggctgga tggccttccc cattatgatt cttctcgctt ccggcggcat cgggatgccc   4740
gcgttgcagg ccatgctgtc caggcaggta gatgacgacc atcagggaca gcttcaagga   4800
tcgctcgcgg ctcttaccag cctaacttcg atcactggac cgctgatcgt cacggcgatt   4860
tatgccgcct cggcgagcac atggaacggg ttggcatgga ttgtaggcgc cgccctatac   4920
cttgtctgcc tccccgcgtt gcgtcgcggt gcatggagcc gggccacctc gacctgaatg   4980
gaagccggcg gcacctcgct aacggattca ccactccaag aattggagcc aatcaattct   5040
tgcggagaac tgtgaatgcg caaaccaacc cttggcagaa catatccatc gcgtccgcca   5100
tctccagcag ccgcacgcgg cgcatctcgg gcagcgttgg gtcctggcca cgggtgcgca   5160
tgatcgtgct cctgtcgttg aggacccggc taggctggcg gggttgcctt actggttagc   5220
agaatgaatc accgatacgc gagcgaacgt gaagcgactg ctgctgcaaa acgtctgcga   5280
cctgagcaac aacatgaatg gtcttcggtt tccgtgtttc gtaaagtctg gaaacgcgga   5340
agtcagcgcc ctgcaccatt atgttccgga tctgcatcgc aggatgctgc tggctaccct   5400
```

-continued

```
gtggaacacc tacatctgta ttaacgaagc gctggcattg accctgagtg atttttctct   5460
ggtcccgccg catccatacc gccagttgtt taccctcaca acgttccagt aaccgggcat   5520
gttcatcatc agtaacccgt atcgtgagca tcctctctcg tttcatcggt atcattaccc   5580
ccatgaacag aaattccccc ttacacggag gcatcaagtg accaaacagg aaaaaaccgc   5640
ccttaacatg gcccgcttta tcagaagcca gacattaacg cttctggaga aactcaacga   5700
gctggacgcg gatgaacagg cagacatctg tgaatcgctt cacgaccacg ctgatgagct   5760
ttaccgcagc tgcctcgcgc gtttcggtga tgacggtgaa aacctctgac acatgcagct   5820
cccggagacg gtcacagctt gtctgtaagc ggatgccggg agcagacaag cccgtcaggg   5880
cgcgtcagcg ggtgttggcg ggtgtcgggg cgcagccatg acccagtcac gtagcgatag   5940
cggagtgtat actggcttaa ctatgcggca tcagagcaga ttgtactgag agtgcaccat   6000
atgcggtgtg aaataccgca cagatgcgta aggagaaaat accgcatcag gcgctcttcc   6060
gcttcctcgc tcactgactc gctgcgctcg gtcgttcggc tgcggcgagc ggtatcagct   6120
cactcaaagg cggtaatacg gttatccaca gaatcagggg ataacgcagg aaagaacatg   6180
tgagcaaaag gccagcaaaa ggccaggaac cgtaaaaagg ccgcgttgct ggcgtttttc   6240
cataggctcc gcccccctga cgagcatcac aaaaatcgac gctcaagtca gaggtggcga   6300
aacccgacag gactataaag ataccaggcg tttccccctg gaagctccct cgtgcgctct   6360
cctgttccga ccctgccgct taccggatac ctgtccgcct ttctcccttc gggaagcgtg   6420
gcgctttctc atagctcacg ctgtaggtat ctcagttcgg tgtaggtcgt tcgctccaag   6480
ctgggctgtg tgcacgaacc ccccgttcag cccgaccgct gcgccttatc cggtaactat   6540
cgtcttgagt ccaacccggt aagacacgac ttatcgccac tggcagcagc cactggtaac   6600
aggattagca gagcgaggta tgtaggcggt gctacagagt tcttgaagtg gtggcctaac   6660
tacggctaca ctagaaggac agtatttggt atctgcgctc tgctgaagcc agttaccttc   6720
ggaaaaagag ttggtagctc ttgatccggc aaacaaacca ccgctggtag cggtggtttt   6780
tttgtttgca agcagcagat tacgcgcaga aaaaaaggat ctcaagaaga tcctttgatc   6840
ttttctacgg ggtctgacgc tcagtggaac gaaaactcac gttaagggat tttggtcatg   6900
agattatcaa aaaggatctt cacctagatc cttttaaatt aaaaatgaag ttttaaatca   6960
atctaaagta tatatgagta aacttggtct gacagttacc aatgcttaat cagtgaggca   7020
cctatctcag cgatctgtct atttcgttca tccatagttg cctgactccc cgtcgtgtag   7080
ataactacga tacgggaggg cttaccatct ggccccagtg ctgcaatgat accgcgagac   7140
ccacgctcac cggctccaga tttatcagca ataaaccagc cagccggaag ggccgagcgc   7200
agaagtggtc ctgcaacttt atccgcctcc atccagtcta ttaattgttg ccgggaagct   7260
agagtaagta gttcgccagt taatagtttg cgcaacgttg ttgccattgc tgcaggtcgg   7320
gagcacagga tgacgcctaa caattcattc aagccgacac cgcttcgcgg cgcggcttaa   7380
ttcaggagtt aaacatcatg agggaagcgg tgatcgccga agtatcgact caactatcag   7440
aggtagttgg cgtcatcgag cgccatctcg aaccgacgtt gctggccgta catttgtacg   7500
gctccgcagt ggatggcggc ctgaagccac acagtgatat tgatttgctg gttacggtga   7560
ccgtaaggct tgatgaaaca acgcggcgag ctttgatcaa cgaccttttg gaaacttcgg   7620
cttcccctgg agagagcgag attctccgcg ctgtagaagt caccattgtt gtgcacgacg   7680
acatcattcc gtggcgttat ccagctaagc gcgaactgca atttggagaa tggcagcgca   7740
atgacattct tgcaggtatc ttcgagccag ccacgatcga cattgatctg gctatcttgc   7800
```

-continued

```
tgacaaaagc aagagaacat agcgttgcct tggtaggtcc agcggcggag gaactctttg   7860
atccggttcc tgaacaggat ctatttgagg cgctaaatga aaccttaacg ctatggaact   7920
cgccgcccga ctgggctggc gatgagcgaa atgtagtgct tacgttgtcc cgcatttggt   7980
acagcgcagt aaccggcaaa atcgcgccga aggatgtcgc tgaagactgg gcaatggagc   8040
gcctgccggc ccagtatcag cccgtcatac ttgaagctag gcaggcttat cttggacaag   8100
aagatcgctt ggcctcgcgc gcagatcagt tggaagaatt tgttcactac gtgaaaggcg   8160
agatcaccaa ggtagtcggc aaataatgtc taacaattcg ttcaagccga cgccgcttcg   8220
cggcgcggct taactcaagc gttagatgct gcaggcatcg tggtgtcacg ctcgtcgttt   8280
ggtatggctt cattcagctc cggttcccaa cgatcaaggc gagttacatg atcccccatg   8340
ttgtgcaaaa aagcggttag ctccttcggt cctccgatcg aggatttttc ggcgctgcgc   8400
tacgtccgck accgcgttga gggatcaagc cacagcagcc cactcgacct ctagccgacc   8460
cagacgagcc aagggatctt tttggaatgc tgctccgtcg tcaggctttc cgacgtttgg   8520
gtggttgaac agaagtcatt atcgtacgga atgccaagca ctcccgaggg gaaccctgtg   8580
gttggcatgc acatacaaat ggacgaacgg ataaaccttt tcacgccctt ttaaatatcc   8640
gttattctaa taaacgctct tttctcttag gtttacccgc caatatatcc tgtcaaacac   8700
tgatagttta aactgaaggc gggaaacgac aatctgatcc ccatcaagct tggtcgagtg   8760
gaagctagct tcccgatcct atctgtcact tcatcaaaag gacagtagaa aaggaaggtg   8820
gcactacaaa tgccatcatt gcgataaagg aaaggctatc gttcaagatg cctctgccga   8880
cagtggtccc aaagatggac ccccacccac gaggagcatc gtggaaaaag aagacgttcc   8940
aaccacgtct tcaaagcaag tggattgatg tgatacttcc actgacgtaa gggatgacgc   9000
acaatcccac tatccttcgc aagacccttc ctctatataa ggaagttcat ttcatttgga   9060
gaggacacgc tgaaatcacc agtctctctc tacaagatcg gggatctcta gctagacgat   9120
cgtttcgcat gattgaacaa gatggattgc acgcaggttc tccggccgct tgggtggaga   9180
ggctattcgg ctatgactgg gcacaacaga caatcggctg ctctgatgcc gccgtgttcc   9240
ggctgtcagc gcaggggcgc ccggttcttt ttgtcaagac cgacctgtcc ggtgccctga   9300
atgaactgca ggacgaggca gcgcggctat cgtggctggc cacgacgggc gttccttgcg   9360
cagctgtgct cgacgttgtc actgaagcgg gaagggactg gctgctattg ggcgaagtgc   9420
cggggcagga tctcctgtca tctcaccttg ctcctgccga gaaagtatcc atcatggctg   9480
atgcaatgcg gcggctgcat acgcttgatc cggctacctg cccattcgac caccaagcga   9540
aacatcgcat cgagcgagca cgtactcgga tggaagccgg tcttgtcgat caggatgatc   9600
tggacgaaga gcatcagggg ctcgcgccag ccgaactgtt cgccaggctc aaggcgcgca   9660
tgcccgacgg cgaggatctc gtcgtgaccc atggcgatgc ctgcttgccg aatatcatgg   9720
tggaaaatgg ccgcttttct ggattcatcg actgtggccg gctgggtgtg gcggaccgct   9780
atcaggacat agcgttggct acccgtgata ttgctgaaga gcttggcggc gaatgggctg   9840
accgcttcct cgtgctttac ggtatcgccg ctcccgattc gcagcgcatc gccttctatc   9900
gccttcttga cgagttcttc tgagcgggac tctggggttc gatccccaat tcccgatcgt   9960
tcaaacattt ggcaataaag tttcttaaga ttgaatcctg ttgccggtct tgcgatgatt  10020
atcatataat ttctgttgaa ttacgttaag catgtaataa ttaacatgta atgcatgacg  10080
ttatttatga gatgggtttt tatgattaga gtcccgcaat tatacattta atacgcgata  10140
```

-continued

```
gaaaacaaaa tatagcgcgc aaactaggat aaattatcgc gcgcggtgtc atctatgtta  10200

ctagatcggg gatcgggcca ctcgaccaag cttctgcagg tcctgctcga gc          10252


<210> SEQ ID NO 16
<211> LENGTH: 8349
<212> TYPE: DNA
<213> ORGANISM: Artificial Sequence
<220> FEATURE:
<221> NAME/KEY: gene
<222> LOCATION: (3666)..(5573)
<223> OTHER INFORMATION: completely synthesized

<400> SEQUENCE: 16

gcaactgttg ggaagggcga tcggtgcggg cctcttcgct attacgccag ctggcgaaag     60

ggggatgtgc tgcaaggcga ttaagttggg taacgccagg gttttcccag tcacgacgtt    120

gtaaaacgac ggccagtgaa ttgcggccac gcgtggtacc aagcttcccg atcctatctg    180

tcacttcatc aaaaggacag tagaaaagga aggtggcacc tacaaatgcc atcattgcga    240

taaaggaaag gctatcattc aagatgcctc tgccgacagt ggtcccaaag atggaccccc    300

acccacgagg agcatcgtgg aaaaagaaga cgttccaacc acgtcttcaa agcaagtgga    360

ttgatgtgat acttccactg acgtaaggga atgacgcaca atcccactat ccttcgcaag    420

acccttcctc tatataagga agttcatttc atttggagag gacacgctga aatcaccagt    480

ctctctctac aagatcgggg atctctagct agacgatcgt ttcgcatgat tgaacaagat    540

ggattgcacg caggttctcc ggccgcttgg gtggagaggc tattcggcta tgactgggca    600

caacagacaa tcggctgctc tgatgccgcc gtgttccggc tgtcagcgca ggggcgcccg    660

gttctttttg tcaagaccga cctgtccggt gccctgaatg aactgcagga cgaggcagcg    720

cggctatcgt ggctggccac gacgggcgtt ccttgcgcag ctgtgctcga cgttgtcact    780

gaagcgggaa gggactggct gctattgggc gaagtgccgg ggcaggatct cctgtcatct    840

caccttgctc ctgccgagaa agtatccatc atggctgatg caatgcggcg gctgcatacg    900

cttgatccgg ctacctgccc attcgaccac caagcgaaac atcgcatcga gcgagcacgt    960

actcggatgg aagccggtct tgtcgatcag gatgatctgg acgaagagca tcaggggctc   1020

gcgccagccg aactgttcgc caggctcaag gcgcgcatgc ccgacggcga ggatctcgtc   1080

gtgacccatg gcgatgcctg cttgccgaat atcatggtgg aaaatggccg cttttctgga   1140

ttcatcgact gtggccggct gggtgtggcg gaccgctatc aggacatagc gttggctacc   1200

cgtgatattg ctgaagagct tggcggcgaa tgggctgacc gcttcctcgt gctttacggt   1260

atcgccgctc ccgattcgca gcgcatcgcc ttctatcgcc ttcttgacga gttcttctga   1320

gcgggactct ggggttcgaa atgaccgacc aagcgacgcc caacctgcca tcacgagatt   1380

tcgattccac cgccgccttc tatgaaaggt tgggcttcgg aatcgttttc cgggacgccg   1440

gctggatgat cctccagcgc ggggatctca tgctggagtt cttcgcccac cccggatcc    1500

ccatgggaat tcccgatcgt tcaaacattt ggcaataaag tttcttaaga ttgaatcctg   1560

ttgccggtct tgcgatgatt atcatataat ttctgttgaa ttacgttaag catgtaataa   1620

ttaacatgta atgcatgacg ttatttatga gatgggtttt tatgattaga gtcccgcaat   1680

tatacattta atacgcgata gaaaacaaaa tatagcgcgc aaactaggat aaattatcgc   1740

gcgcggtgtc atctatgtta ctagatcggg gatatccccg cggccgcgtt aacaagcttc   1800

tgcaggtccg atgtgagact tttcaacaaa gggtaatatc cggaaacctc ctcggattcc   1860

attgcccagc tatctgtcac tttattgtga agatagtgga aaaggaaggt ggctcctaca   1920
```

-continued

```
aatgccatca ttgcgataaa ggaaaggcca tcgttgaaga tgcctctgcc gacagtggtc   1980
ccaaagatgg acccccaccc acgaggagca tcgtggaaaa agaagacgtt ccaaccacgt   2040
cttcaaagca agtggattga tgtgatggtc cgatgtgaga cttttcaaca aagggtaata   2100
tccggaaacc tcctcggatt ccattgccca gctatctgtc actttattgt gaagatagtg   2160
gaaaaggaag gtggctccta caaatgccat cattgcgata aaggaaaggc catcgttgaa   2220
gatgcctctg ccgacagtgg tcccaaagat ggacccccac ccacgaggag catcgtggaa   2280
aaagaagacg ttccaaccac gtcttcaaag caagtggatt gatgtgatat ctccactgac   2340
gtaagggatg acgcacaatc ccactatcct tcgcaagacc cttcctctat ataaggaagt   2400
tcatttcatt tggagaggac acgctgacaa gctgactcta gcagatctac cgtcttcggt   2460
acgcgctcac tccgccctct gcctttgtta ctgccacgtt tctctgaatg ctctcttgtg   2520
tggtgattgc tgagagtggt ttagctggat ctagaattac actctgaaat cgtgttctgc   2580
ctgtgctgat tacttgccgt cctttgtagc agcaaaatat agggacatgg tagtacgaaa   2640
cgaagataga acctacacag caatacgaga aatgtgtaat ttggtgctta gcggtattta   2700
tttaagcaca tgttggtgtt atagggcact tggattcaga agtttgctgt taatttaggc   2760
acaggcttca tactacatgg gtcaatagta tagggattca tattataggc gatactataa   2820
taatttgttc gtctgcagag cttattattt gccaaaatta gatattccta ttctgttttt   2880
gtttgtgtgc tgttaaattg ttaacgcctg aaggaataaa tataaatgac gaaattttga   2940
tgtttatctc tgctccttta ttgtgaccat aagtcaagat cagatgcact tgttttaaat   3000
attgttgtct gaagaaataa gtactgacag tattttgatg cattgatctg cttgtttgtt   3060
gtaacaaaat ttaaaaataa agagtttcct ttttgttgct ctccttacct cctgatggta   3120
tctagtatct accaactgac actatattgc ttctctttac atacgtatct tgctcgatgc   3180
cttctcccta gtgttgacca gtgttactca catagtcttt gctcatttca ttgtaatgca   3240
gataccaagc ggcctctaga ggatcagcat ggcgcccacc gtgatgatgg cctcgtcggc   3300
caccgccgtc gctccgttcc tggggctcaa gtccaccgcc agcctccccg tcgcccgccg   3360
ctcctccaga agcctcggca acgtcagcaa cggcggaagg atccggtgca tgcaggtaac   3420
aaatgcatcc tagctagtag ttctttgcat tgcagcagct gcagctagcg agttagtaat   3480
aggaagggaa ctgatgatcc atgcatggac tgatgtgtgt tgcccatccc atcccatccc   3540
atttcccaaa cgaaccgaaa acaccgtact acgtgcaggt gtggccctac ggcaacaaga   3600
agttcgagac gctgtcgtac ctgccgccgc tgtcgaccgg cgggcgcatc cgctgcatgc   3660
aggccatgga caactccgtc ctgaactctg gtcgcaccac catctgcgac gcctacaacg   3720
tcgcggcgca tgatccattc agcttccagc acaagagcct cgacactgtt cagaaggagt   3780
ggacggagtg gaagaagaac aaccacagcc tgtacctgga ccccatcgtc ggcacggtgg   3840
ccagcttcct tctcaagaag gtcggctctc tcgtcgggaa gcgcatcctc tcggaactcc   3900
gcaacctgat ctttccatct ggctccacca acctcatgca agacatcctc agggagaccg   3960
agaagtttct caaccagcgc ctcaacactg atacccttgc tcgcgtcaac gctgagctga   4020
cgggtctgca agcaaacgtg gaggagttca accgccaagt ggacaacttc ctcaacccca   4080
accgcaatgc ggtgcctctg tccatcactt cttccgtgaa caccatgcaa caactgttcc   4140
tcaaccgctt gcctcagttc cagatgcaag gctaccagct gctcctgctg ccactctttg   4200
ctcaggctgc caacctgcac ctctccttca ttcgtgacgt gatcctcaac gctgacgagt   4260
```

-continued

```
ggggcatctc tgcagccacg ctgaggacct accgcgacta cctgaagaac tacaccaggg   4320
actactccaa ctattgcatc aacacctacc agtcggcctt caagggcctc aatacgaggc   4380
ttcacgacat gctggagttc aggacctaca tgttcctgaa cgtgttcgag tacgtcagca   4440
tctggtcgct cttcaagtac cagagcctgc tggtgtccag cggcgccaac ctctacgcca   4500
gcggctctgg tccccaacaa actcagagct tcaccagcca ggactggcca ttcctgtatt   4560
cgttgttcca agtcaactcc aactacgtcc tcaacggctt ctctggtgct cgcctctcca   4620
acaccttccc caacattgtt ggcctccccg gctccaccac aactcatgct ctgcttgctg   4680
ccagagtgaa ctactccggc ggcatctcga gcggcgacat tggtgcatcg ccgttcaacc   4740
agaacttcaa ctgctccacc ttcctgccgc cgctgctcac cccgttcgtg aggtcctggc   4800
tcgacagcgg ctccgaccgc gagggcgtgg ccaccgtcac caactggcaa accgagtcct   4860
tcgagaccac ccttggcctc cggagcggcg ccttcacggc gcgtgggaat tctaactact   4920
tccccgacta cttcatcagg aacatctctg gtgttcctct cgtcgtccgc aacgaggacc   4980
tccgccgtcc actgcactac aacgagatca ggaacatcgc ctctccgtcc gggacgcccg   5040
gaggtgcaag ggcgtacatg gtgagcgtcc ataacaggaa gaacaacatc cacgctgtgc   5100
atgagaacgg ctccatgatc cacctggcgc ccaatgatta caccggcttc accatctctc   5160
caatccacgc cacccaagtg aacaaccaga cacgcacctt catctccgag aagttcggca   5220
accagggcga ctccctgagg ttcgagcaga acaacaccac cgccaggtac accctgcgcg   5280
gcaacggcaa cagctacaac ctgtacctgc gcgtcagctc cattggcaac tccaccatca   5340
gggtcaccat caacgggagg gtgtacacag ccaccaatgt gaacacgacg accaacaatg   5400
atggcgtcaa cgacaacggc gcccgcttca gcgacatcaa cattggcaac gtggtggcca   5460
gcagcaactc cgacgtcccg ctggacatca acgtgaccct gaactctggc acccagttcg   5520
acctcatgaa catcatgctg gtgccaacta acatctcgcc gctgtactga taggagctct   5580
gatccccatg ggaattcccg atcgttcaaa catttggcaa taaagtttct taagattgaa   5640
tcctgttgcc ggtcttgcga tgattatcat ataatttctg ttgaattacg ttaagcatgt   5700
aataattaac atgtaatgca tgacgttatt tatgagatgg gtttttatga ttagagtccc   5760
gcaattatac atttaatacg cgatagaaaa caaaatatag cgcgcaaact aggataaatt   5820
atcgcgcgcg gtgtcatcta tgttactaga tcggggatat ccccggggcg gccgcgggga   5880
attcggtacc aagcttacgc gtggccgcag cttggcgtaa tcatggtcat agctgtttcc   5940
tgtgtgaaat tgttatccgc tcacaattcc acacaacata cgagccggaa gcataaagtg   6000
taaagcctgg ggtgcctaat gagtgagcta actcacatta attgcgttgc gctcactgcc   6060
cgctttccag tcgggaaacc tgtcgtgcca gctgcattaa tgaatcggcc aacgcgcggg   6120
gagaggcggt ttgcgtattg ggcgctcttc cgcttcctcg ctcactgact cgctgcgctc   6180
ggtcgttcgg ctgcggcgag cggtatcagc tcactcaaag gcggtaatac ggttatccac   6240
agaatcaggg gataacgcag gaaagaacat gtgagcaaaa ggccagcaaa aggccaggaa   6300
ccgtaaaaag gccgcgttgc tggcgttttt ccataggctc cgcccccctg acgagcatca   6360
caaaaatcga cgctcaagtc agaggtggcg aaacccgaca ggactataaa gataccaggc   6420
gtttccccct ggaagctccc tcgtgcgctc tcctgttccg accctgccgc ttaccggata   6480
cctgtccgcc tttctccctt cgggaagcgt ggcgctttct caatgctcac gctgtaggta   6540
tctcagttcg gtgtaggtcg ttcgctccaa gctgggctgt gtgcacgaac cccccgttca   6600
gcccgaccgc tgcgccttat ccggtaacta tcgtcttgag tccaacccgg taagacacga   6660
```

-continued

```
cttatcgcca ctggcagcag ccactggtaa caggattagc agagcgaggt atgtaggcgg   6720
tgctacagag ttcttgaagt ggtggcctaa ctacggctac actagaagga cagtatttgg   6780
tatctgcgct ctgctgaagc cagttacctt cggaaaaaga gttggtagct cttgatccgg   6840
caaacaaacc accgctggta gcggtggttt ttttgtttgc aagcagcaga ttacgcgcag   6900
aaaaaaagga tctcaagaag atcctttgat cttttctacg gggtctgacg ctcagtggaa   6960
cgaaaactca cgttaaggga ttttggtcat gagattatca aaaaggatct tcacctagat   7020
ccttttgggg tgggcgaaga actccagcat gagatccccg cgctggagga tcatccagcc   7080
ggcgtcccgg aaaacgattc cgaagcccaa cctttcatag aaggcggcgg tggaatcgaa   7140
atctcgtgat ggcaggttgg gcgtcgcttg gtcggtcatt tcgaacccca gagtcccgct   7200
cagaagaact cgtcaagaag gcgatagaag gcgatgcgct gcgaatcggg agcggcgata   7260
ccgtaaagca cgaggaagcg gtcagcccat tcgccgccaa gctcttcagc aatatcacgg   7320
gtagccaacg ctatgtcctg atagcggtcc gccacaccca gccggccaca gtcgatgaat   7380
ccagaaaagc ggccattttc caccatgata ttcggcaagc aggcatcgcc atgggtcacg   7440
acgagatcct cgccgtcggg catgcgcgcc ttgagcctgg cgaacagttc ggctggcgcg   7500
agcccctgat gctcttcgtc cagatcatcc tgatcgacaa gaccggcttc catccgagta   7560
cgtgctcgct cgatgcgatg tttcgcttgg tggtcgaatg ggcaggtagc cggatcaagc   7620
gtatgcagcc gccgcattgc atcagccatg atggatactt tctcggcagg agcaaggtga   7680
gatgacagga gatcctgccc cggcacttcg cccaatagca gccagtccct tcccgcttca   7740
gtgacaacgt cgagcacagc tgcgcaagga acgcccgtcg tggccagcca cgatagccgc   7800
gctgcctcgt cctgcagttc attcagggca ccggacaggt cggtcttgac aaaaagaacc   7860
gggcgcccct gcgctgacag ccggaacacg gcggcatcag agcagccgat tgtctgttgt   7920
gcccagtcat agccgaatag cctctccacc caagcggccg gagaacctgc gtgcaatcca   7980
tcttgttcaa tcatgcgaaa cgatcctcat cctgtctctt gatcagatct tgatcccctg   8040
cgccatcaga tccttggcgg caagaaagcc atccagttta ctttgcaggg cttcccaacc   8100
ttaccagagg gcgccccagc tggcaattcc ggttcgcttg ctgtccataa aaccgcccag   8160
tctagctatc gccatgtaag cccactgcaa gctacctgct ttctctttgc gcttgcgttt   8220
tcccttgtcc agatagccca gtagctgaca ttcatccggg gtcagcaccg tttctgcgga   8280
ctggctttct acgtgttccg cttcctttag cagcccttgc gccctgagtg cttgcggcag   8340
cgtgaagct                                                           8349
```

<210> SEQ ID NO 17
<211> LENGTH: 1912
<212> TYPE: DNA
<213> ORGANISM: Bacillus thuringiensis

<400> SEQUENCE: 17

```
atgaatagtg tattgaatag cggaagaact actatttgtg atgcgtataa tgtagcggct     60
catgatccat ttagttttca acacaaatca ttagataccg tacaaaagga atggacggag    120
tggaaaaaaa ataatcatag tttataccta gatcctattg ttggaactgt ggctagtttt    180
ctgttaaaga aagtggggag tcttgttgga aaaaggatac taagtgagtt acggaattta    240
atatttccta gtggtagtac aaatctaatg caagatattt taagagagac agaaaaattc    300
ctgaatcaaa gacttaatac agacactctt gcccgtgtaa atgcggaatt gacagggctg    360
```

-continued

```
caagcaaatg tagaagagtt taatcgacaa gtagataatt ttttgaaccc taaccgaaac    420

gctgttcctt tatcaataac ttcttcagtt aatacaatgc aacaattatt tctaaataga    480

ttaccccagt tccagatgca aggataccaa ctgttattat tacctttatt tgcacaggca    540

gccaatttac atctttcttt tattagagat gttattctaa atgcagatga atggggaatt    600

tcagcagcaa cattacgtac gtatcgagat tacttgaaaa attatacaag agattactct    660

aactattgta taaatacgta tcaaagtgcg tttaaaggtt taaacactcg tttacacgat    720

atgttagaat ttagaacata tatgttttta aatgtatttg agtatgtatc tatctggtcg    780

ttgtttaaat atcaaagtct tctagtatct tccggtgcta atttatatgc aagtggtagt    840

ggaccacagc agacccaatc atttacttca caagactggc cattttata ttctcttttc    900

caagttaatt caaattatgt gttaaatgga tttagtggtg ctaggctttc taataccttc    960

cctaatatag ttggtttacc tggttctact acaactcacg cattgcttgc tgcaagggtt   1020

aattacagtg gaggaatttc gtctggtgat ataggtgcat ctccgtttaa tcaaaatttt   1080

aattgtagca catttctccc cccattgtta acgccatttg ttaggagttg gctagattca   1140

ggttcagatc gggagggcgt tgccaccgtt acaaattggc aaacagaatc ctttgagaca   1200

actttagggt taaggagtgg tgcttttaca gctcgcggta attcaaacta tttcccagat   1260

tattttattc gtaatatttc tggagttcct ttagttgtta gaaatgaaga tttaagaaga   1320

ccgttacact ataatgaaat aagaaatata gcaagtcctt caggaacacc tggtggagca   1380

cgagcttata tggtatctgt gcataacaga aaaaataata tccatgctgt tcatgaaaat   1440

ggttctatga ttcatttagc gccaaatgac tatacaggat ttactatttc gccgatacat   1500

gcaactcaag tgaataatca aacacgaaca tttatttctg aaaaatttgg aaatcaaggt   1560

gattctttaa ggtttgaaca aaacaacacg acagctcgtt atacgcttag agggaatgga   1620

aatagttaca atctttattt aagagtttct tcaataggaa attccactat tcgagttact   1680

ataaacggta gggtatatac tgctacaaat gttaatacta ctacaaataa cgatggagtt   1740

aatgataatg gagctcgttt ttcagatatt aatatcggta atgtagtagc aagtagtaat   1800

tctgatgtac cattagatat aaatgtaaca ttaaactccg gtactcaatt tgatcttatg   1860

aatattatgc ttgtaccaac taatatttca ccactttatt aaggtttgag ta           1912
```

<210> SEQ ID NO 18
<211> LENGTH: 633
<212> TYPE: PRT
<213> ORGANISM: Bacillus thuringiensis

<400> SEQUENCE: 18

```
Met Asn Ser Val Leu Asn Ser Gly Arg Thr Thr Ile Cys Asp Ala Tyr
  1               5                  10                  15

Asn Val Ala Ala His Asp Pro Phe Ser Phe Gln His Lys Ser Leu Asp
             20                  25                  30

Thr Val Gln Lys Glu Trp Thr Glu Trp Lys Lys Asn Asn His Ser Leu
         35                  40                  45

Tyr Leu Asp Pro Ile Val Gly Thr Val Ala Ser Phe Leu Leu Lys Lys
     50                  55                  60

Val Gly Ser Leu Val Gly Lys Arg Ile Leu Ser Glu Leu Arg Asn Leu
 65                  70                  75                  80

Ile Phe Pro Ser Gly Ser Thr Asn Leu Met Gln Asp Ile Leu Arg Glu
                 85                  90                  95

Thr Glu Lys Phe Leu Asn Gln Arg Leu Asn Thr Asp Thr Leu Ala Arg
```

-continued

```
            100                 105                 110

Val Asn Ala Glu Leu Thr Gly Leu Gln Ala Asn Val Glu Glu Phe Asn
        115                 120                 125

Arg Gln Val Asp Asn Phe Leu Asn Pro Asn Arg Asn Ala Val Pro Leu
    130                 135                 140

Ser Ile Thr Ser Ser Val Asn Thr Met Gln Gln Leu Phe Leu Asn Arg
145                 150                 155                 160

Leu Pro Gln Phe Gln Met Gln Gly Tyr Gln Leu Leu Leu Leu Pro Leu
                165                 170                 175

Phe Ala Gln Ala Ala Asn Leu His Leu Ser Phe Ile Arg Asp Val Ile
            180                 185                 190

Leu Asn Ala Asp Glu Trp Gly Ile Ser Ala Ala Thr Leu Arg Thr Tyr
        195                 200                 205

Arg Asp Tyr Leu Lys Asn Tyr Thr Arg Asp Tyr Ser Asn Tyr Cys Ile
    210                 215                 220

Asn Thr Tyr Gln Ser Ala Phe Lys Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Gln Gln Thr Gln Ser Phe
        275                 280                 285

Thr Ser Gln Asp Trp Pro Phe Leu Tyr Ser Leu Phe Gln Val Asn Ser
    290                 295                 300

Asn Tyr Val Leu Asn Gly Phe Ser Gly Ala Arg Leu Ser Asn Thr Phe
305                 310                 315                 320

Pro Asn Ile Val Gly Leu Pro Gly Ser Thr Thr Thr His Ala Leu Leu
                325                 330                 335

Ala Ala Arg Val Asn Tyr Ser Gly Gly Ile Ser Ser Gly Asp Ile Gly
            340                 345                 350

Ala Ser Pro Phe Asn Gln Asn Phe Asn Cys Ser Thr Phe Leu Pro Pro
        355                 360                 365

Leu Leu Thr Pro Phe Val Arg Ser Trp Leu Asp Ser Gly Ser Asp Arg
    370                 375                 380

Glu Gly Val Ala Thr Val Thr Asn Trp Gln Thr Glu Ser Phe Glu Thr
385                 390                 395                 400

Thr Leu Gly Leu Arg Ser Gly Ala Phe Thr Ala Arg Gly Asn Ser Asn
                405                 410                 415

Tyr Phe Pro Asp Tyr Phe Ile Arg Asn Ile Ser Gly Val Pro Leu Val
            420                 425                 430

Val Arg Asn Glu Asp Leu Arg Arg Pro Leu His Tyr Asn Glu Ile Arg
        435                 440                 445

Asn Ile Ala Ser Pro Ser Gly Thr Pro Gly Gly Ala Arg Ala Tyr Met
    450                 455                 460

Val Ser Val His Asn Arg Lys Asn Asn Ile His Ala Val His Glu Asn
465                 470                 475                 480

Gly Ser Met Ile His Leu Ala Pro Asn Asp Tyr Thr Gly Phe Thr Ile
                485                 490                 495

Ser Pro Ile His Ala Thr Gln Val Asn Asn Gln Thr Arg Thr Phe Ile
            500                 505                 510

Ser Glu Lys Phe Gly Asn Gln Gly Asp Ser Leu Arg Phe Glu Gln Asn
        515                 520                 525
```

-continued

```
Asn Thr Thr Ala Arg Tyr Thr Leu Arg Gly Asn Gly Asn Ser Tyr Asn
    530                 535                 540

Leu Tyr Leu Arg Val Ser Ser Ile Gly Asn Ser Thr Ile Arg Val Thr
545                 550                 555                 560

Ile Asn Gly Arg Val Tyr Thr Ala Thr Asn Val Asn Thr Thr Thr Asn
                565                 570                 575

Asn Asp Gly Val Asn Asp Asn Gly Ala Arg Phe Ser Asp Ile Asn Ile
            580                 585                 590

Gly Asn Val Val Ala Ser Ser Asn Ser Asp Val Pro Leu Asp Ile Asn
        595                 600                 605

Val Thr Leu Asn Ser Gly Thr Gln Phe Asp Leu Met Asn Ile Met Leu
    610                 615                 620

Val Pro Thr Asn Ile Ser Pro Leu Tyr
625                 630
```

METHODS FOR TRANSFORMING PLANTS TO EXPRESS CRY2AB δ-ENDOTOXINS TARGETED TO THE PLASTIDS

1.0 BACKGROUND OF THE INVENTION

1.1 Field of the Invention

The present invention relates generally to transgenic plants having insecticidal capabilities, and to DNA constructs utilized to transfer genes conferring insect resistance into plant genomes. More specifically, the present invention relates to a method of expressing insecticidal proteins in plants transformed with a *B. thuringiensis* δ-endotoxin encoding gene, resulting in effective control of susceptible target pests.

1.2 Description of Related Art

1.2.1 Methods of Controlling Insect Infestation in Plants

The Gram-positive soil bacterium *B. thuringiensis* is well known for its production of proteinaceous parasporal crystals, or δ-endotoxins, that are toxic to a variety of Lepidopteran, Coleopteran, and Dipteran larvae. *B. thuringiensis* produces crystal proteins during sporulation which are specifically toxic to certain species of insects. Many different strains of *B. thuringiensis* have been shown to produce insecticidal crystal proteins. Compositions comprising *B. thuringiensis* strains which produce proteins having insecticidal activity have been used commercially as environmentally-acceptable topical insecticides because of their toxicity to the specific target insect, and non-toxicity to plants and other non-targeted organisms.

δ-endotoxin crystals are toxic to insect larvae by ingestion. Solubilization of the crystal in the midgut of the insect releases the protoxin form of the δ-endotoxin which, in most instances, is subsequently processed to an active toxin by midgut protease. The activated toxins recognize and bind to the brush-border of the insect midgut epithelium through receptor proteins. Several putative crystal protein receptors have been isolated from certain insect larvae (Knight et al., 1995; Gill et al., 1995; Masson et al., 1995). The binding of active toxins is followed by intercalation and aggregation of toxin molecules to form pores within the midgut epithelium. This process leads to osmotic imbalance, swelling, lysis of the cells lining the midgut epithelium, and eventual larvae mortality.

1.2.2 Transgenic *B. thuringiensis* δ-Endotoxins as Biopesticides

Plant resistance and biological control are central tactics of control in the majority of insecticide improvement programs applied to the most diverse crops. With the advent of molecular genetic techniques, various δ-endotoxin genes have been isolated and their DNA sequences determined. These genes have been used to construct certain genetically engineered *B. thuringiensis* products that have been approved for commercial use. Recent developments have seen new δ-endotoxin delivery systems developed, including plants that contain and express genetically engineered δ-endotoxin genes. Expression of *B. thuringiensis* δ-endotoxins in plants holds the potential for effective management of plant pests so long as certain problems can be overcome. These problems include the development of insect resistance to the particular Cry protein expressed in the plant, and development of morphologically abnormal plants because of the presence of the transgene.

Expression of *B. thuringiensis* δ-endotoxins in transgenic cotton, corn, and potatoes has proven to be an effective means of controlling agriculturally important insect pests (Perlak et al., 1990; Koziel et al., 1993; Perlak et al., 1993). Transgenic crops expressing *B. thuringiensis* δ-endotoxins enable growers to significantly reduce the application of costly, toxic, and sometimes ineffective topical chemical insecticides. Use of transgenes encoding *B. thuringiensis* δ-endotoxins is particularly advantageous when insertion of the transgene has no negative effect on the yield of desired product from the transformed plants. Yields from crop plants expressing certain *B. thuringiensis* δ-endotoxins such as Cry1A or Cry3A have been observed to be equivalent or better than otherwise similar non-transgenic commercial plant varieties. This indicates that expression of some *B. thuringiensis* δ-endotoxins does not have a significant negative impact on plant growth or development. This is not the case, however, for all *B. thuringiensis* δ-endotoxins that may be used to transform plants.

The use of topical *B. thuringiensis*-derived insecticides may also result in the development of insect strains resistant to the insecticides. Resistance to Cry1A *B. thuringiensis* δ-endotoxins applied as foliar sprays has evolved in at least one well documented instance (Shelton et al., 1993). It is expected that insects may similarly evolve resistance to *B. thuringiensis* δ-endotoxins expressed in transgenic plants. Such resistance, should it become widespread, would clearly limit the commercial value of corn, cotton, potato, and other germplasm containing genes encoding *B. thuringiensis* δ-endotoxins. One possible way to both increase the effectiveness of the insecticide against target pests and to reduce the development of insecticide-resistant pests would be to ensure that transgenic crops express high levels of *B. thuringiensis* δ-endotoxins (McGaughey and Whalon, 1993; Roush, 1994).

In addition to producing a transgenic plant which expresses *B. thuringiensis* δ-endotoxins at high levels, commercially viable *B. thuringiensis* genes must satisfy several additional criteria. For instance, expression of these genes in transgenic crop plants must not reduce the vigor, viability or fertility of the plants, nor may it affect the normal morphology of the plants. Such detrimental effects have two undesired results: they may interfere with the recovery and propagation of transgenic plants; they may also impede the development of mature plants, or confer unacceptable agronomic characteristics.

There remains a need for compositions and methods useful in producing transgenic plants which express *B. thuringiensis* δ-endotoxins at levels high enough to effectively control target plant insect pests as well as prevent the development of insecticide-resistant pest strains. A method resulting in higher levels of expression of the *B. thuringiensis* δ-endotoxins will also provide the advantages of more frequent attainment of commercially viable transformed plant lines and more effective protection from infestation for the entire growing season.

There also remains a need for a method of increasing the level of expression of *B. thuringiensis* δ-endotoxins which does not simultaneously result in plant morphological changes that interfere with optimal growth and development of desired plant tissues. For example, the method of potentiating expression of the *B. thuringiensis* δ-endotoxins in corn should not result in a corn plant which cannot optimally develop for cultivation. Achievement of these goals such as high expression levels as well as recovery of morphologically normal plants has been elusive, and their pursuit has been ongoing and an important aspect of the long term value of insecticidal plant products.

2.0 SUMMARY OF THE INVENTION

Described are novel methods for expressing Cry2A *B. thuringiensis* δ-endotoxins which lack significant Dipteran inhibiting activity in transformed plants. This method advantageously results in both increased levels of expression of *B. thuringiensis* δ-endotoxins as well as a higher rate of recovery of morphologically-normal plants.

By achieving high rates of expression, the present invention addresses another limitation of the prior art: development of insect resistance. Specifically, the instant invention provides a superior strategy for the delay or elimination of the development of resistance to Cry1A δ-endotoxins, the *B. thuringiensis* proteins most commonly expressed by transgenic lines. The disclosed methods involve expression of the Cry2A class of *B. thuringiensis* δ-endotoxins and particularly those that lack Dipteran-inhibiting activity. *B. thuringiensis* δ-endotoxins of the Cry2A group have no significant homology to Cry1A-type δ-endotoxins and display distinct binding and pore-forming characteristics (English et al., 1994), and as such are expected to control insects that become resistant to, or that are not affected by, Cry1A δ-endotoxins (Hofte and Whiteley, 1989).

In preferred embodiments, the present invention provides an isolated and purified DNA construct comprising a Cry2A δ-endotoxin-encoding region localized to a plastid or chloroplast, or localized to a plant cell nuclear genome and operably linked to a region encoding a plastid transit peptide (PTP). Preferred DNA constructs of the present invention include those constructs that encode Cry2A δ-endotoxins lacking Dipteran-inhibitory activity, though complete inactivity towards Dipterans is not required. In an illustrative embodiment, DNA constructs of the present invention encode a Cry2Ab δ-endotoxin operably linked to a DNA segment (or sequence) encoding a plastid transit peptide, which is one means of enabling localization of a Cry2Ab δ-endotoxin to a plastid or chloroplast. In certain embodiments, the Cry2Ab δ-endotoxin comprises the sequence of SEQ ID NO:2. The inventors contemplate, however, that any Cry2A δ-endotoxin lacking Dipteran-inhibitory activity may be utilized according to the present invention, with those bearing substantial homologies to Cry2Ab being particularly preferred.

In another embodiment, the DNA constructs of the present invention exploit nucleic acid segments encoding PTPs to potentiate expression of the δ-endotoxin. The use of one type of PTP, a chloroplast targeting peptide (CTP), in conjunction with a crylA *B. thuringiensis* transgene to promote expression of the transgene in the transformed plant is disclosed in U.S. Pat. No. 5,500,365 (specifically incorporated herein by reference in its entirety). Where increased expression was observed, however, it was ascribed in part to the use of a new 5' untranslated leader sequence in the expression vector.

In contrast to the prior art, the present invention discloses a structural DNA sequence that causes the production of an RNA sequence which encodes a targeted fusion protein comprising an amino-terminal plastid transit peptide with a Cry2Ab δ-endotoxin; and a 3' non-translated DNA sequence which functions in plant cells to cause transcriptional termination and the addition of polyadenylated nucleotides to the 3' end of the RNA sequence. Surprisingly, this DNA construct results in increased levels of expression of the Cry2A δ-endotoxin. The targeted fusion protein is non-active to all species, but is produced as a means for localizing the mature, insecticidally active δ-endotoxin protein to the chloroplast, yielding surprising and unexpected beneficial agronomic effects.

One embodiment conceived of in the present invention is the introduction of a gene encoding a Cry2A δ-endotoxin lacking Dipteran activity into the chloroplast or plastid genome. Alternatively, a gene encoding a Cry2A δ-endotoxin lacking Dipteran activity could be expressed from an autonomously replicating episomal element located within the chloroplast or plastid.

In another preferred embodiment, the invention provides for transgenic plants which have been transformed with an isolated and purified DNA construct that is translated and expressed at high levels by the plant. Both monocot and dicot plants may be transformed according to the methods and with the DNA constructs disclosed herein. The plant transformed by the instant invention may be prepared, in a further preferred embodiment, by a process including obtainment of the isolated and purified DNA construct, and then transforming the plant with the construct so that the plant expresses the proteins for which the construct encodes. The inventors have observed that transformation of plants by the disclosed methods results in increased frequency of transformants which express the transgene, as well as the generation of more morphologically normal plants from initial transformants.

It is contemplated that the increased expression levels observed in the disclosed invention will allow for reduced development of insect resistance to Bt δ-endotoxins. This may be achieved by transforming a plant with the preferred DNA construct to achieve high rates of Cry2A expression alone, or by simultaneously exposing target insects to Cry1A and non-Dipteran active Cry2A δ-endotoxins expressed in susceptible plants. Such insects include Ostrina spp., Diatraea spp., Helicoverpa spp., and Spodoptera spp., in *Zea mays; Heliothis virescens,* Helicoverpa spp., Pectinophora spp., in *Gossypium hirsutum;* Anticarsia spp., Pseudoplusia spp., Epinotia spp., in *Glycine max;* and *Scirpophaga incertulas* in *Oryza sativa.*

It is therefore contemplated that the method disclosed by the present invention will provide many advantages over the prior art including those specifically outlined above. These advantages include: obtaining improved control of susceptible insects; minimizing the development of insecticide-resistant insect strains; obtaining a greater number of commercially viable insect resistant plant lines; achieving season long protection from insect pathogens; and increasing the incidence of morphologically-normal transformed plants. An additional advantage of the present invention is that reduced numbers of transgenic lines would need to be produced in order to identify a transgenic event with normal growth characteristics.

2.1 Nucleic Acid Compositions

In one important embodiment, the invention provides an isolated and purified nucleic acid construct comprising a Cry2A coding region and a PTP coding region. These DNA constructs, when transferred into a plant, undergo cellular processes resulting in increased expression of δ-endotoxins in the transgenic plant. The Cry2A endotoxins of the instant invention are preferably not effective against Dipteran species, though some adverse effects on Dipterans may be tolerated. In certain embodiments, the DNA construct encodes a Dipteran-inactive Cry2Ab δ-endotoxin, and in more preferred embodiments, the Cry2Ab δ-endotoxin has the polypeptide sequence of SEQ ID NO:2, or one substantially homologous to the polypeptide sequence of SEQ ID NO:2. Such nucleotide homologues may be greater than approximately 88% homologous, greater than about 90% homologous, greater than about 95% homologous, and even greater than about 99% homologous with the Cry2Ab δ-endotoxin disclosed in SEQ ID NO:2. Exemplary peptides include those that are about 88, 89, 90, 91, 92, 93, 94, 95, 96, 97, 98 or even 99 or greater percent homologous to the Cry2Ab δ-endotoxin disclosed in SEQ ID NO:2.

In even more preferred embodiments, the DNA construct of the present invention comprises a Cry2Ab δ-endotoxin-encoding region with the nucleic acid sequence of SEQ ID NO:1, or a sequence substantially homologous to that of SEQ ID NO:1. Also envisioned as within the scope of this invention are those DNA constructs having segments with substantial homologies to the nucleic acid sequence disclosed in SEQ ID NO:1, such as those which may be about 90% homologous, or about 95% homologous, or even about 99% homologous. More specifically, homologous nucleic acid sequences included in the present invention include those that are about 90, 91, 92 ,93, 94, 95, 96, 97, 98, and 99 percent homologous to the nucleic acid sequence of SEQ ID NO:1.

The DNA constructs provided herein also include a PTP coding region positioned upstream of the cry2A δ-endotoxin coding region and downstream of a promoter. These plastid transit peptide coding regions may encode any plant functional PTP, and may operate to target encoded proteins to certain plastids within the plant cell, or to increase the expression of the δ-endotoxin for which the DNA construct encodes. In preferred embodiments, the present invention may include a PTP selected from the group including zmSSU, PTP1, PTP1Δ, and PTP2, or any other plant functional PTPs. More preferably, the plastid transit peptide coding region encodes a plastid transit peptide having the amino acid sequence of SEQ ID NO:4, SEQ ID NO:6, SEQ ID NO:8, or SEQ ID NO:10, or any polypeptide sequence substantially homologous to these. Even more preferably, the instant invention comprises a plastid transit peptide coding region having the nucleic acid sequence of SEQ ID NO:3, SEQ ID NO:5, SEQ ID NO:7, or SEQ ID NO:9, or a nucleic acid sequence which is substantially homologous to these.

Also, the inventors contemplate that the present invention would further achieve the goals of increased pathogenicity to pests, and result in decreased development of pesticide-resistant insects, if the DNA constructs provided herein were co-expressed along with other pesticidal compositions such as other proteins. Accordingly, the invention provides for use of the disclosed DNA constructs which further comprise plant-expressible coding regions for other Cry proteins. Included in these would be coding regions for Cry1 proteins such as Cry1A, Cry1Ab, Cry1Bb, or Cry1 chimeras (see co-pending U.S. applications Ser. No.'s 08/754,490 and 08/922,505, and co-pending PCT Application PCT/US97/17507 based on U.S. application Ser. No. 08/721,259, each specifically incorporated herein by reference in its entirety).

In certain preferred embodiments, the DNA construct is an expression cassette which can be excised and isolated from said plasmid.

2.2 Additional Nucleic acid Composition Elements

The polynucleotide compositions of the present invention are useful in transforming both monocotyledonous and dicotyledonous plants. Accordingly, the DNA construct of the present invention may further comprise other various regulatory elements to aid in protein expression and to further facilitate introduction of the DNA construct into the plant. One example of this is the inclusion, in the DNA construct, of an intron positioned in the untranslated leader, upstream relative to the plastid transit peptide coding region. One useful leader sequence is the petunia heat shock protein. In various alternative embodiments, the intron may be any of the following: Adh intron 1, sucrose synthase intron, TMV omega element, maize heat shock protein (hsp) 70, or the rice ActI intron. In preferred embodiments, the intron is either maize heat shock protein 70 or petunia heat shock protein 70.

Provided in another preferred embodiment of the present invention is a polynucleotide sequence comprising a substantially Dipteran inactive cry2A δ-endotoxin coding region and a PTP coding region positioned under the control of a plant operable promoter. The use of a promoter is required for driving cellular processes so that expression of the gene is maximized. Preferred promoters include the following: CaMV 35S, histone, CaMV 19S, nos, OCS, Adh, sucrose synthase, α-tubulin, actin, cab, PEPCase, ssRUBISCO, Actl, Famv, enhanced FMV, or R-gene complex associated promoters. In more preferred embodiments, the promoter is the enhanced or duplicated CaMV 35S promoter (Kay et al., 1987). In additional preferred embodiments, the promoter is the FMV35S promoter. Plant chloroplast or plastid functional promoters are also within the scope of the present invention.

The present invention further contemplates the inclusion of a terminator region in the DNA construct to aid cellular processes involved with protein expression. In various embodiments, this terminator may be any of the following: the *Agrobacterium tumefaciens* nopaline synthase gene terminator, the *Agrobacterium tumefaciens* octopine synthase gene terminator, and the 3' end of the protease inhibitor I or II genes from potato or tomato. In an especially preferred embodiment, the terminator is the *Agrobacterium tumefaciens* nopaline synthase gene terminator.

2.3 Transformation Vectors

Because the DNA construct of the present invention is primarily, though not exclusively, intended for use in the transformation of plants, it is in certain preferred embodiments, contained within an expression vector. Such expression vectors may contain a variety of regulatory and other elements intended to allow for optimal expression of the desired proteins for which the expression vector encodes. These additional elements may include promoters, terminators, and introns as outlined above in section 2.2. The vector containing the DNA construct and any regulatory or other elements may be selected from the group consisting of a yeast artificial chromosome, bacterial artificial chromosome, a plasmid, or a cosmid.

Further, the expression vectors themselves may be of a variety of forms. These forms may differ for various reasons, and will likely be comprised of varying components depending upon whether they are intended to transform a monocotyledonous plant or a dicotyledonous plant. For example, FIG. 1 illustrates one possible embodiment, where the monocotyledonous expression vector contains the cry2Ab gene in the plasmid designated as (SEQ ID NO:16). It is further contemplated that other expression vectors containing the expression cassettes embodied in these plasmid vectors, as well as expression cassettes containing substantial homologues, will also be useful transformation constructs. Accordingly, any transformation vector containing the nucleic acid sequence of from nucleic acid 1781 to 5869 of SEQ ID NO:16.

Figure 2:
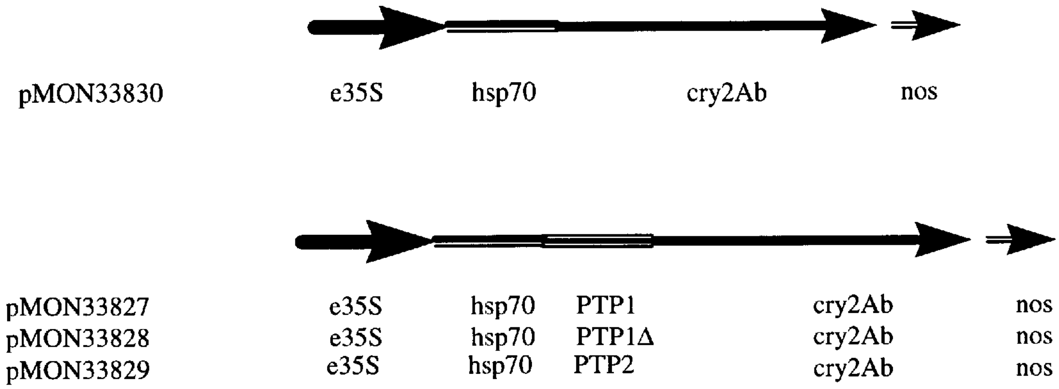

FIG. 2 illustrates one possible dicotyledonous expression vector. It contains the cry2Ab gene embodied in the plasmids designated as pMON33827 (SEQ ID NO:13), pMON33828 (SEQ ID NO:14), and pMON33829 (SEQ ID NO:15). As with the illustrative monocotyledonous transformation vectors, the inventors further contemplate that other expression vectors containing the expression cassettes embodied in these plasmid vectors, or substantial homologues to those expression cassettes, will be useful as dicotyledonous transformation constructs. Preferred dicotyledonous expression cassettes include those embodied by nucleic acids 17 to 3182 of SEQ ID NO:13; nucleic acids 17 to 3092 of SEQ ID NO:14; and nucleic acids 17 to 3155 of SEQ ID NO:15. Illustrative embodiments of vectors containing such expression cassettes are disclosed in the sequences designated herein as SEQ ID NO:13, SEQ ID NO:14, and SEQ ID NO:15.

Vectors further envisioned to be within the scope of the present invention include those vectors capable of containing both the Dipteran-inactive cry2A nucleic acid compositions disclosed in section 2.1 above, as well as any other DNA constructs which further comprise plant-expressible coding regions for other Cry proteins such as a Cry1 protein. Vectors capable of containing both of these constructs may further comprise an internal ribosome entry site between the DNA construct; they may also contain a variety of different cistrons, rendering them polycistronic or multicistronic 2.4 Transformed Host Cells Another preferred embodiment of the present invention encompasses cells transformed with the DNA constructs disclosed herein in sections 2.1 and 2.2, and by use of the transformation vectors disclosed in section 2.3. Transformed cells contemplated in the present invention include both prokaryotic and eukaryotic cells which express the proteins encoded-for by the novel DNA constructs of the present invention. The process of producing transgenic cells is well-known in the art. In general, the method comprises transforming a suitable host cell with a DNA segment which contains a promoter operatively linked to a coding region that encodes a *B. thuringiensis* δ-endotoxin. Such a coding region is generally operatively linked to a transcription-terminating region, whereby the promoter is capable of driving the transcription of the coding region in the cell, and hence providing the cell the ability to produce the δ-endotoxin in vivo. Alternatively, in instances where it is desirable to control, regulate, or decrease the amount of a particular δ-endotoxin or endotoxins expressed in a particular transgenic cell, the invention also provides for the expression of δ-endotoxin antisense mRNA; intron antisense mRNA; PTP antisense mRNA; or UTR antisense mRNA. The use of antisense mRNA as a means of controlling or decreasing the amount of a given protein of interest in a cell is well-known in the art.

In a preferred embodiment, the invention encompasses a plant cell which has been transformed with a nucleic acid segment or DNA construct of the invention, and which expresses a gene or gene segment encoding one or more of the Dipteran-inactive Cry2A *B. thuringiensis* δ-endotoxins as disclosed herein. As used herein, the term "transgenic plant cell" is intended to refer to a plant cell that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of a Dipteran-inactive Cry2A *B. thuringiensis* δ-endotoxin-encoding DNA constructs as disclosed in sections 2.1 and 2.2 above. In some instances, more than one transgene will be incorporated into the nuclear genome, or into the chloroplast or plastid genome of the transformed host plant cell. Such is the case when more than one crystal protein-encoding DNA segment is incorporated into the genome of such a plant. In certain situations, it may be desirable to have one, two, three, four, or even more *B. thuringiensis* crystal protein-encoding polynucleotides (either native or recombinantly-engineered) incorporated and stably expressed in the transformed transgenic plant.

In preferred embodiments, the introduction of the transgene into the genome of the plant cell results in a stable integration wherein the offspring of such plants also contain a copy of the transgene in their genome. The heritability of this genetic element by the progeny of the plant into which the gene was originally introduced is a preferred aspect of this invention. A preferred gene which may be introduced includes, for example a *B. thuringiensis* δ-endotoxin, and particularly one or more of those described herein.

Means for transforming a plant cell and the preparation of a transgenic cell line are well-known in the art (as exemplified in U.S. Pat. Nos. 5,550,318; 5,508,468; 5,482,852; 5,384,253; 5,276,269; and 5,225,341, all specifically incorporated herein by reference in their entirety), and are briefly discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant.

Transgenic cells specifically contemplated in the present invention include transgenic plant cells. Particularly preferred plant cells include those cells obtained from corn, wheat, soybean, turf grasses, ornamental plant, fruit tree, shrubs, vegetables, grains, legumes, and the like, or any plant into which introduction of a Dipteran-inactive *B. thuringiensis* δ-endotoxin transgene is desired.

2.5 Transformed Plants

In another aspect, plants transformed with any DNA construct of the present invention that express the proteins for which the construct encodes, are contemplated as being a part of this invention. Accordingly, the invention further provides transgenic plants which have been transformed with a DNA construct, as disclosed herein in sections 2.1 and 2.2, and transformed by use of transformation vectors as disclosed in section 2.3. Agronomic, horticultural, ornamental, and other economically or commercially useful plants can be made in accordance with the methods described herein, to express *B. thuringiensis* δ-endotoxins at levels high enough to confer resistance to insect pathogens while remaining morphologically normal.

Such plants may co-express the δ-endotoxin polypeptide along with other antifungal, antibacterial, or antiviral pathogenesis-related peptides, polypeptides, or proteins; insecticidal proteins; proteins conferring herbicide resistance; and proteins involved in improving the quality or quantity of plant products or agronomic performance of plants. Simultaneous co-expression of multiple proteins in plants is advantageous in that it exploits more than one mode of action to control plant pathogenic damage. This can minimize the possibility of developing resistant pathogen strains, broaden the scope of resistance, and potentially result in a synergistic insecticidal effect, thereby enhancing a plant's ability to resist insect infestation (Intl. Patent Appl. Publ. No. WO 92/17591, Oct. 15, 1992, specifically incorporated herein by reference in its entirety).

The transformed plant of the current invention may be either a monocotyledonous plant or a dicotyledonous plant. Where the plant is a monocotyledonous plant, it may be any one of a variety of species. Preferred monocotyledonous species encompassed by the present invention may include maize, rice, wheat, barley, oats, rye, millet, sorghum, sugarcane, asparagus, turfgrass, or any of a number of other grains or cereal plants. In preferred embodiments, the monocot is a maize plant.

The present invention also contemplates a variety of dicotyledonous plants such as cotton, soybean, tomato, potato, citrus, tobacco, sugar beet, alfalfa, fava bean, pea, bean, apple, cherry, pear, strawberry, raspberry, or any other legume, tuber, or fruit plant. In preferred embodiments, the dicot is a soybean plant, a tobacco plant, or a cotton plant.

Many of the plants intended to be transformed according to the disclosed invention are commercial crop plants. The commercial form of these plants may be the original plants, or their offspring which have inherited desired transgenes. Accordingly, plants further contemplated within the ambit of the present invention include any offspring of plants transformed with any of the permutations of the DNA construct which are noted in this application. Specifically, the offspring may be defined as an $R_0$ transgenic plant. Other progeny of the transformed plant are also included within the scope of the present invention, including any progeny plant of any generation of the transformed plant, wherein the progeny plant has inherited the DNA construct from any $R_0$ plant.

Upon transformation with a specific DNA construct, the nucleic acid or polynucleotide segments of the construct may be incorporated in various portions into a chromosome of the transformant. Therefore, in another embodiment, the present invention encompasses any transgenic plant or plant cell prepared by the use of a DNA construct disclosed herein. Such a plant or cell encompassed by the present invention includes those prepared by a process which has the following steps: (1) obtaining a DNA construct including a Dipteran-inactive Cry2A *B. thuringiensis* δ-endotoxin coding region positioned in frame and under the control of a promoter operable in the plant, and a plastid transit peptide coding region positioned upstream of the Cry2A *B. thuringiensis* δ-endotoxin coding region and downstream of the promoter; and (2) transforming the plant with the obtained DNA construct, so that the plant expresses the Cry2A *B. thuringiensis* δ-endotoxin. The plant may also have been transformed so that it further incorporates into its genome and expresses other Cry δ-endotoxins.

In a related aspect, the present invention also encompasses a seed produced by the transformed plant, a progeny from such seed, and a seed produced by the progeny of the original transgenic plant, produced in accordance with the above process. Such progeny and seeds will have a Dipteran-inactive *B. thuringiensis* δ-endotoxin transgene stably incorporated into its genome, and such progeny plants will inherit the traits afforded by the introduction of a stable transgene in Mendelian fashion. All such transgenic plants having incorporated into their genome transgenic DNA segments encoding any DNA construct disclosed herein, particularly those disclosed in sections 2.1 and 2.2 are aspects of this invention.

Recombinant plants, cells, seeds, and other tissues could also be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67–70, 1987). Methods and compositions for obtaining cells containing chloroplasts into which heterologous DNA has been inserted has been described by Daniell et al., U.S. Pat. No. 5,693,507 (1997).

2.6 Plant Transformation Methods

2.6.1 Method of Expressing a Cry2A δ-Endotoxin in a Plant

In another preferred embodiment, the present invention provides a method for expressing Dipteran-inactive Cry2A *B. thuringiensis* δ-endotoxins at high levels in transgenic plants. The disclosed methods may exploit any of the DNA constructs disclosed in sections 2.1 and 2.2 above, as well as any of the transformation vectors disclosed, for example, in section 2.3 above. The contemplated methods enable Cry2A δ-endotoxins, an alternative to Cry1A *B. thuringiensis* δ-endotoxins for the control of several insect pests, to be expressed in plants without negatively affecting the recovery of agronomic qualities of transgenic plants. The invention described herein also enables expression of Cry2A δ-endotoxins at levels up to 25 times higher than that achieved by current methods.

The method described here thus enables plants expressing Cry2A to be used as either an alternative or supplement to plants expressing Cry1A-type *B. thuringiensis* δ-endotoxins for both control and resistance management of key insect pests, including Ostrina sp, Diatraea sp, Helicoverpa sp, Spodoptera sp in *Zea mays; Heliothis virescens,* Helicoverpa sp, Pectinophora sp. in *Gossypium hirsutum;* and Anticarsia sp, Pseudoplusia sp, Epinotia sp in *Glycine max.* It is also contemplated that the methods described may be used to dramatically increase expression of *B. thuringiensis* δ-endotoxins including and related to Cry2A, thus increasing its effectiveness against target pests and decreasing the likelihood of evolved resistance to these proteins. In one embodiment of the present invention, the Cry2Ab δ-endotoxin is expressed. Target pests of this protein and their common hosts are shown below in Table 1.

TABLE 1

Cry2Ab Target Pests and Common Plant Hosts of those Pests

| Pests | Hosts | Reference |
|---|---|---|
| *Ostrina nubialis* | *Zea mays* | Donovan |
| *Diatraea grandiosella* | *Gossypium hirsutum* | U. S. Pat. No. 5,338,544 |
| *Helicoverpa zea* | Glycine max | |
| *Heliothis virescens* | | |
| *Pectinophora gossypiella* | | |
| *Anticarsia gemmatalis* | | |
| *Pseudoplusia includens* | | |
| *Epinotia aporema* | | |

The method of expressing a Cry2A *B. thuringiensis* δ-endotoxin in a plant disclosed herein includes the steps of: (1) obtaining nucleic acid segment comprising a promoter operably linked to a first polynucleotide sequence encoding a plastid transit peptide, and a second polynucleotide sequence, encoding a Cry2A *B. thuringiensis* δ-endotoxin lacking Dipteran activity, to yield a fusion protein comprised of an amino-terminal plastid transit peptide and a Cry2A *B. thuringiensis* δ-endotoxin lacking Dipteran activity; and (2) transforming the plant with the DNA construct of step 1 so that the plant expresses the protein fusion. In a preferred embodiment, the nucleic acid segment employed in step (1) of this method is structured so that the 5' end of the second polynucleotide sequence is operably linked in the same translational reading frame to the 3' end of the first polynucleotide sequence.

The plant or plant cell transformed by the method disclosed herein may be either a monocotyledonous plant or a dicotyledonous plant. Where the plant is a monocotyledonous plant, it may be any one of a variety of species. Preferred monocotyledonous species encompassed by the present invention may include maize, rice, wheat, barley, oats, rye, millet, sorghum, sugarcane, asparagus, turfgrass, or any of a number of other grains or cereal plants. In preferred embodiments, the monocot is a maize plant.

The present invention also contemplates a process by which a variety of dicotyledonous plants or plant cells are transformed. Such dicotyledonous plants may include plants such as cotton, soybean, tomato, potato, citrus, tobacco, sugar beet, alfalfa, fava bean, pea, bean, apple, cherry, pear, strawberry, raspberry, or any other legume, tuber, or fruit plant. In preferred embodiments, the dicot is a soybean plant, a tobacco plant or cell, or a cotton plant or cell.

2.6.2 Method of expressing a Cry2Ab δ-endotoxin in a Progeny Plant

As noted with regard to other embodiments disclosed in the present invention, many of the plants intended to be transformed according to the disclosed invention are commercial crop plants. The commercial form of these plants may be the original plants, or their offspring which have inherited desired transgenes. Accordingly, the inventors further contemplate that the method disclosed herein includes a method of producing a transgenic progeny plant or progeny plant cell. The method of producing such progeny includes: The method of expressing a Cry2A *B. thuringiensis* δ-endotoxin in a plant disclosed herein includes the steps of: (1) obtaining nucleic acid segment comprising a promoter operably linked to a first polynucleotide sequence encoding a plastid transit peptide, and a second polynucleotide sequence, encoding a Cry2A *B. thuringiensis* δ-endotoxin lacking Dipteran activity, to yield a fusion protein comprised of an amino-terminal plastid transit peptide and a Cry2A *B. thuringiensis* δ-endotoxin lacking Dipteran activity; (2) obtaining a second plant; and (3) crossing the first and second plants to obtain a crossed transgenic progeny plant or plant cell which has inherited the nucleic acid segments from the first plant. The present invention specifically encompasses the progeny, progeny plant or seed from any of the monocotyledonous or dicotyledonous plants, including those noted in sections 2.5 and 2.6.1 above.

2.6.3 Method of Co-Expressing Cry2Ab and other Cry *B. thuringiensis* δ-endotoxins in a Plant and a Progeny Plant In another preferred embodiment, the method of expressing the Dipteran-inactive Cry2A *B. thuringiensis* δ-endotoxin disclosed herein includes co-expression of the disclosed DNA construct in any of its various embodiments, along with a Cry1 *B. thuringiensis* δ-endotoxin. The method of expressing these Cry *B. thuringiensis* δ-endotoxins together is expected to achieve increased insecticidal properties in the transformed plant through increased expression and decreased development of insect resistance - all of which are desired results not present in existing technologies. This co-expression may be in the original transformant, or in any number of generations of progeny of the original transformant which have inherited the genes to co-express the proteins encoded for by any of the DNA constructs disclosed herein.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Schematic illustration of elements of monocot plant cry2Ab expression vectors pMON30464, pMON30463, and pMON26800.

FIG. 2. Schematic illustration of elements of dicot cry2Ab expression vectors pMON33830, pMON33827, pMON33828, and pMON33829.

Figure 3:
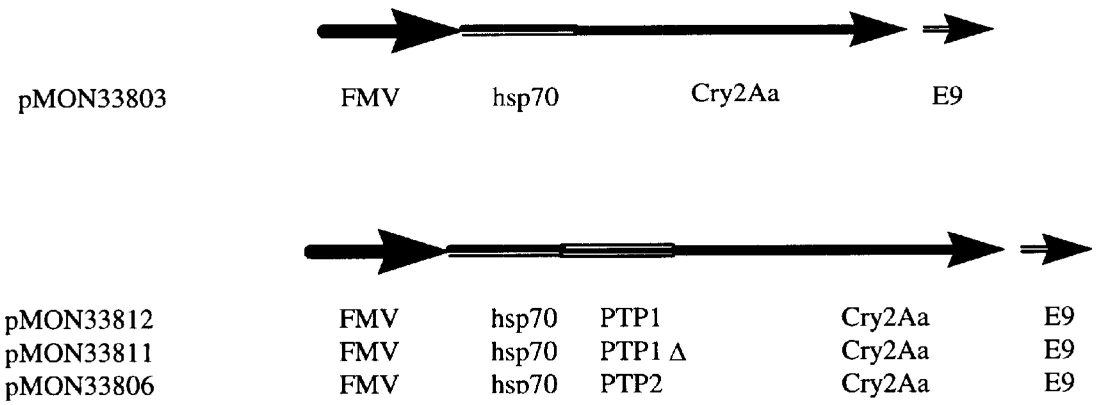

FIG. 3. Schematic illustration of elements of dicot cry2Aa expression vectors pMON33803, pMON33812, pMON338 11, and pMON33806.

Figure 4:
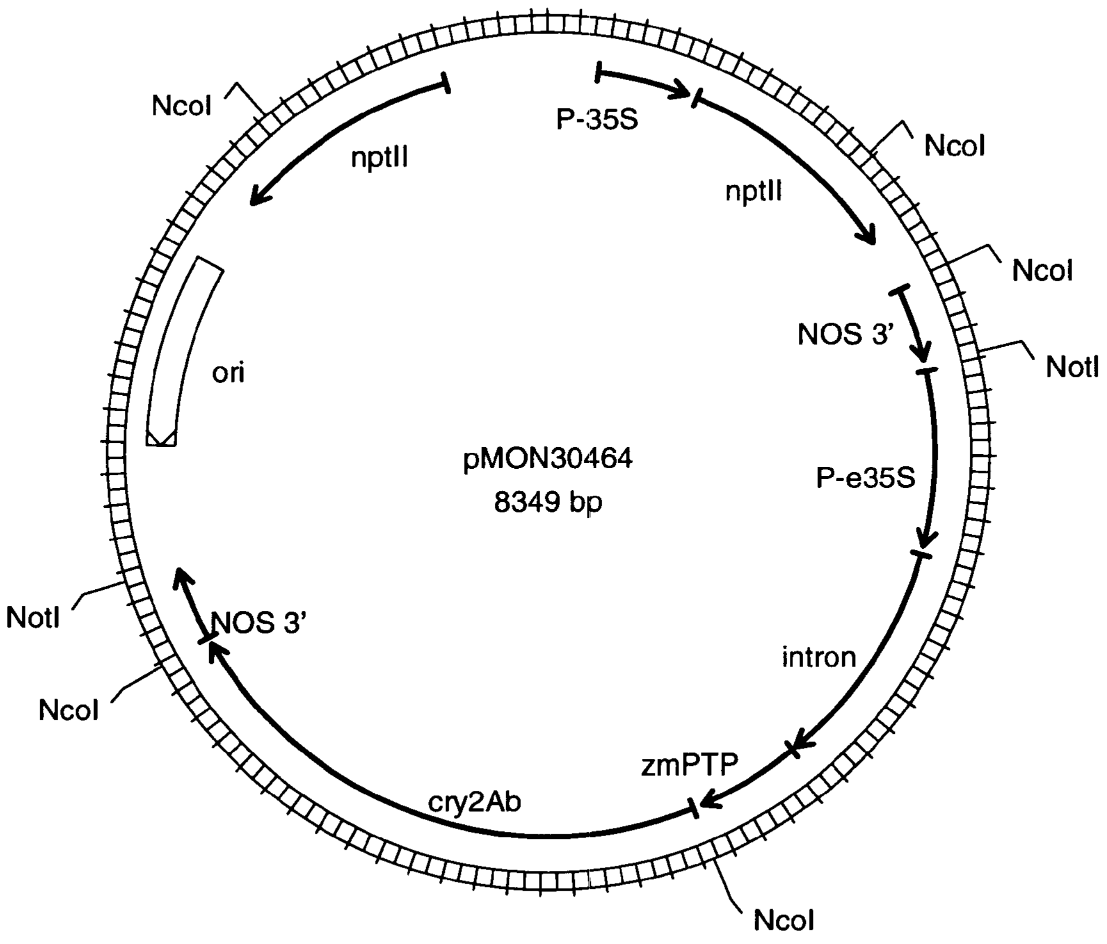

FIG. 4. Plasmid designated pMON30464.

Figure 5:
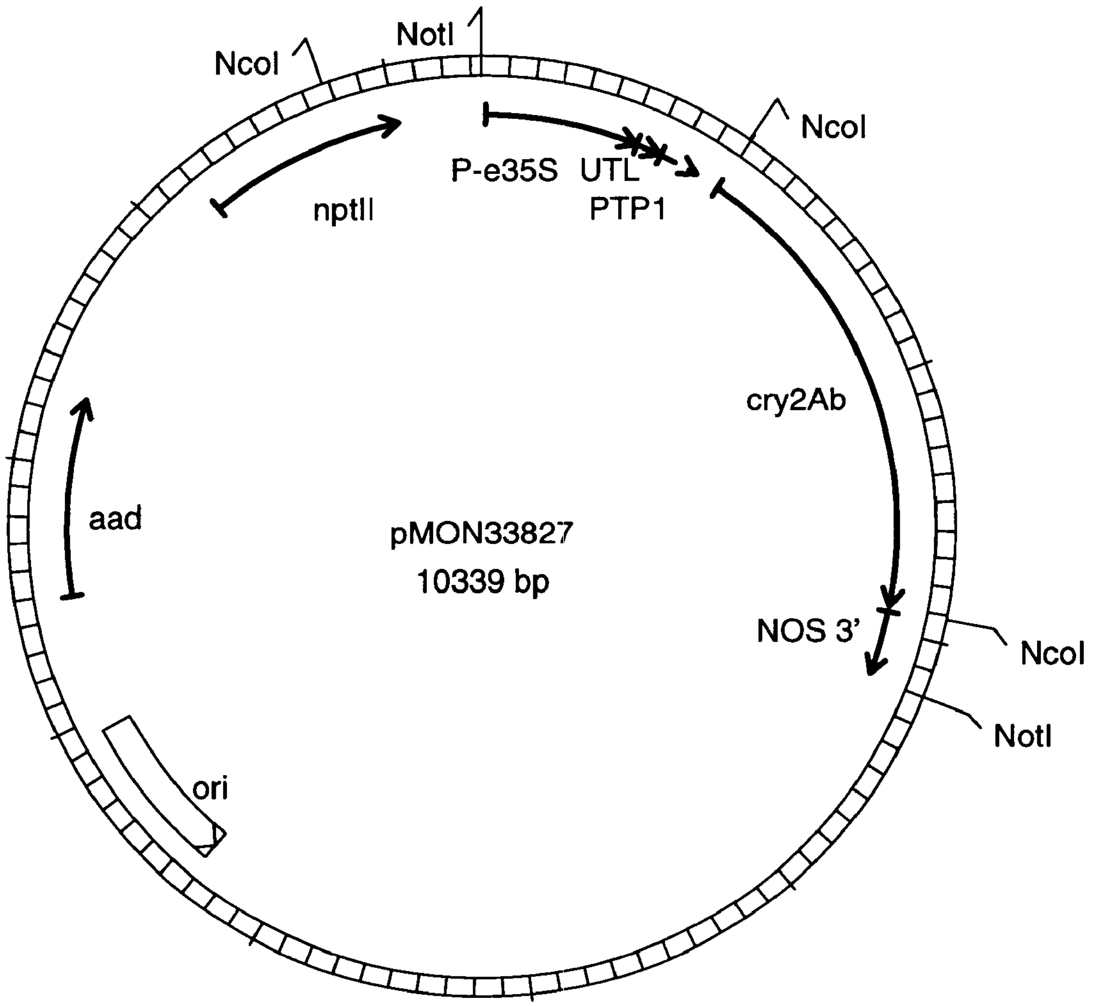

FIG. 5. Plasmid designated pMON33827.

Figure 6:
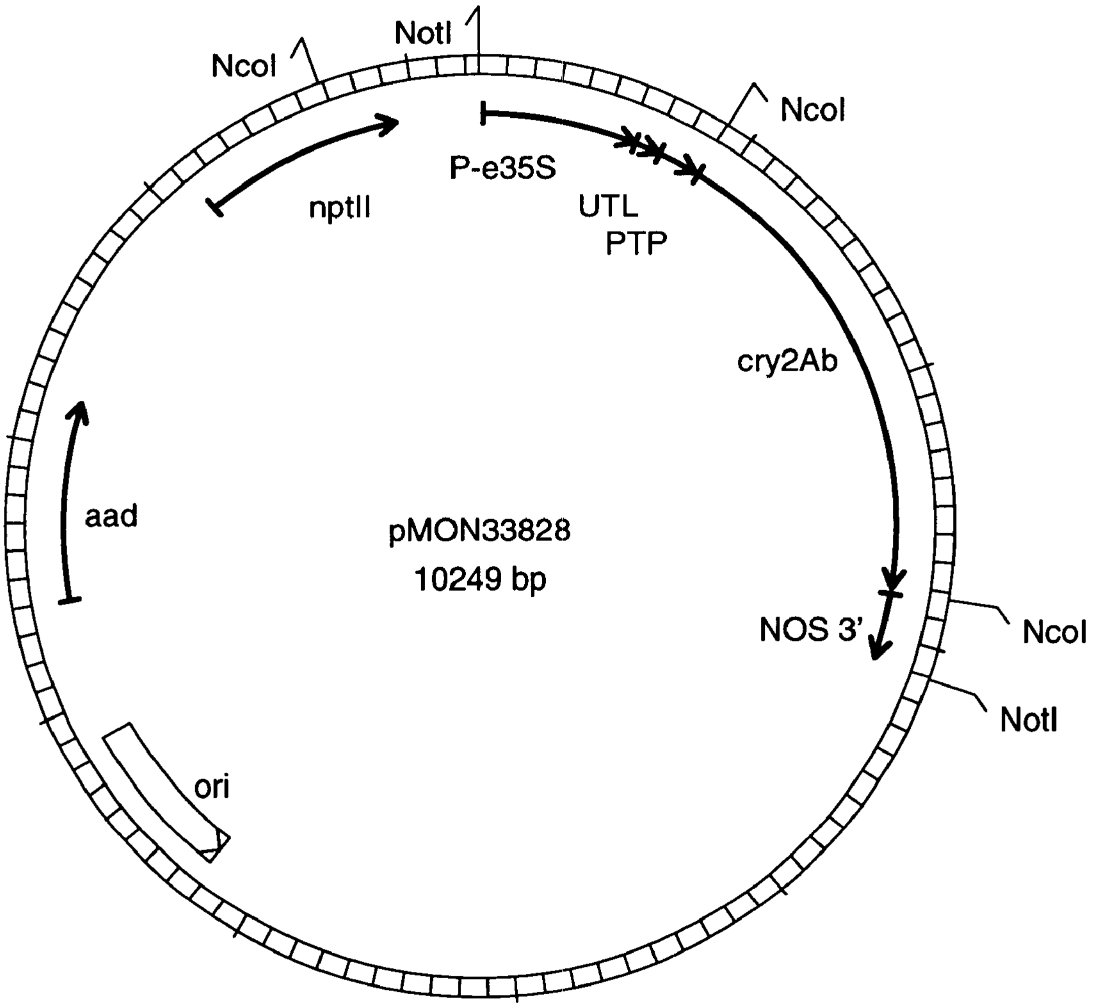

FIG. 6. Plasmid designated pMON33828.

Figure 7:
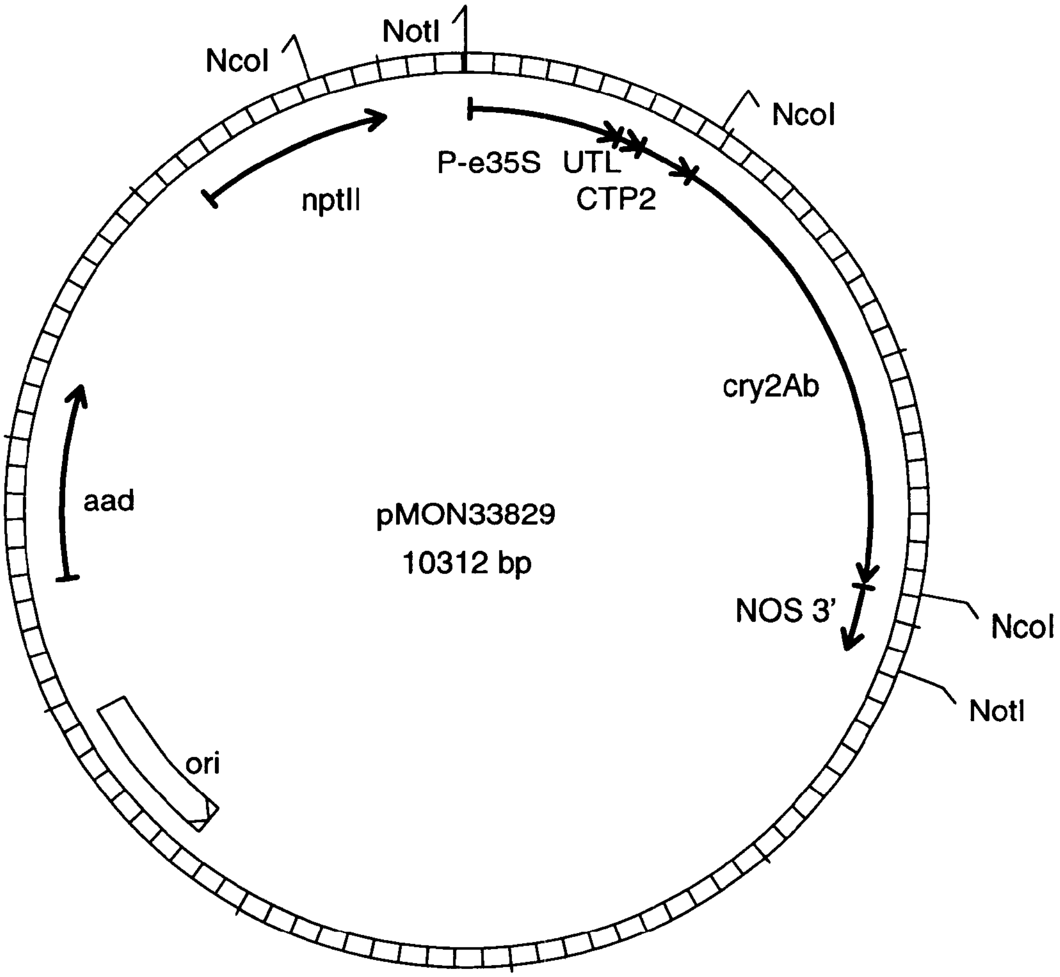

FIG. 7. Plasmid designated pMON33829.

4.0 DESCRIPTION OF ILLUSTRATIVE EMBODIMENTS

The following detailed description of the invention is provided to aid those skilled in the art in practicing the present invention. Even so, the following detailed description should not be construed to unduly limit the present invention as modifications and variations in the embodiments discussed herein may be made by those of ordinary skill in the art without departing from the spirit or scope of the present inventive discovery.

4.1 Identification of Sequences

SEQ ID NO:1. Nucleic acid sequence of a cry2Ab gene.

SEQ ID NO:2. Amino acid sequence of a Cry2Ab *B. thuringiensis* δ-endotoxin.

SEQ ID NO:3. Nucleic acid sequence of a zmSSU plastid transit peptide.

SEQ ID NO:4. Amino acid sequence of a zmSSU plastid transit peptide.

SEQ ID NO:5. Nucleic acid sequence of a plastid transit peptide 1 (PTP1).

SEQ ID NO:6. Amino acid sequence of a PTP1.

SEQ ID NO:7. Nucleic acid sequence of a plastid transit peptide 1Δ(PTP1Δ).

SEQ ID NO:8. Amino acid sequence of a PTP1Δ.

SEQ ID NO:9. Nucleic acid sequence of a plastid transit peptide 2 (PTP2).

SEQ ID NO:10. Amino acid sequence of a PTP2.

SEQ ID NO:11. Nucleic acid sequence of a cry2Aa gene.

SEQ ID NO:12. Amino sequence of a$_o$Cry2Aa polypeptide.

SEQ ID NO:13. pMON33827.

SEQ ID NO:14. pMON33828.

SEQ ID NO:15. pMON33829.

SEQ ID NO:16. pMON30464.

SEQ ID NO:17. *Bacillus thuringiensis* cry2Ab gene sequence, UWGCG accession number M23724 (Widner and Whiteley).

SEQ ID NO:18. *Bacillus thuringiensis* cry2Ab amino acid sequence translated from SEQ ID NO:17.

4.2 Definitions

The following words and phrases herein have the meanings as set forth below.

Biological functional equivalents. As used herein such equivalents with respect to the insecticidal proteins of the present invention are peptides, polypeptides and proteins that contain a sequence or moiety exhibiting sequence similarity to the novel peptides of the present invention, such as Cry2Ab, and which exhibit the same or similar functional properties as that of the polypeptides disclosed herein, including insecticidal activity. Biological equivalents also include peptides, polypeptides and proteins that react with, ie. specifically bind to antibodies raised against Cry2Ab and that exhibit the same or similar insecticidal activity, including both monoclonal and polyclonal antibodies.

Chloroplast or plastid localized, as used herein, refers to a biological molecule, either polynucleotide or polypeptide, which is positioned within the chloroplast or plastid such that the molecule is isolated from the cellular cytoplasmic milieu, and functions within the chloroplast or plastid cytoplasm to provide the effects claimed in the instant invention. Localization of a biological molecule to the chloroplast or plastid can occur, with reference to polynucleotides, by artificial mechanical means such as electroporation, mechanical microinjection, or by polynucleotide coated microprojectile bombardment, or with reference to polypeptides, by secretory or import means wherein a natural, synthetic, or heterologous plastid or chloroplast targeting peptide sequence is used which functions to target, insert, assist, or localize a linked polypeptide into a chloroplast or plastid.

Combating or Controlling Insect Damage in an agricultural context refers to reduction in damage to a crop caused by infection by an insect pest. More generally, this phrase refers to reduction in the adverse effects caused by the presence of an undesired insect in any particular location.

Event refers to a transgenic plant derived from the insertion of foreign DNA into one or more unique sites in the nuclear genomic DNA.

Expression: The combination of intracellular processes, including transcription, translation, and other intracellular protein and RNA processing and stabilization functions, undergone by a coding DNA molecule such as a structural gene to produce a polypeptide.

Insecticidal polypeptide refers to a polypeptide having insecticidal properties, e.g., a polypeptide which inhibits the growth, development, viability or fecundity of target insect pests.

Operably Linked: Nucleic acid coding segments connected in frame so that the properties of one influence the expression of the other.

Plant-Expressible Coding Regions: Coding regions which are expressible in planta because they contain typical plant regulatory elements to facilitate the expression of the gene of interest.

Plastid Transit Peptide: Any amino acid sequence useful in targeting or localizing a linked amino acid, such as a protein fusion, to a subcellular compartment or organelle such as a plastid.

Progeny: "Progeny" includes any offspring or descendant of the transgenic plant, or any subsequent plant which has the transformant in its lineage. Progeny is not limited to one generation, but rather encompasses the transformant's descendants so long as they contain or express the transgene. Seeds containing transgenic embryos as well as seeds from the transgenic plants and their offspring or descendants are also important parts of the invention.

Promoter: A recognition site on a DNA sequence or group of DNA sequences that provide an expression control element for a structural gene and to which RNA polymerase specifically binds and initiates RNA synthesis (transcription) of that gene.

$R_0$ is the primary regenerant plant derived from transformation of plant tissue or cells in culture. Subsequent progeny or generations derived from the $R_0$ are referred to as $R_1$ (first generation), $R_2$ (second generation), etc.

Regeneration: The process of growing a plant from a plant cell (e.g., plant protoplast or explant).

Stably maintained within a plant plastid or chloroplast refers to the introduction by electroporation, transformation, transduction, or micelle or liposome-like fusion of a polynucleotide or nucleic acid into a chloroplast or plastid in such a way that the nucleic acid remains within the recipient chloroplast or plastid and within all subsequent progeny of the recipient chloroplast or plastid either by incorporation by recombination into the chloroplast or plastid genome, or as an autonomously replicating covalently closed circular replicon residing within the chloroplast or plastid by means of growth of any plant, plant cell, or plant tissue containing such transformed chloroplast or plastid and while in the presence of a chemical or compound which requires one or more genes present on and expressed from the replicon in order to ensure the survival of the transformed plastid or chloroplast and their progeny plastids or chloroplasts within the plant, plant cell, or plant tissue.

Structural Coding Sequence refers to a DNA sequence that encodes a peptide, polypeptide, or protein that is made by a cell following transcription of the structural coding sequence to messenger RNA (mRNA), followed by translation of the mRNA to the desired peptide, polypeptide, or protein product.

Structural gene: A gene that is expressed to produce a polypeptide.

Substantial homology: As this term is used herein, it refers to nucleic acid or polypeptide sequences which are about 86% homologous, to about 90% homologous, to about 95% homologous, to about 99% homologous. More specifically, the inventors envision substantial homologues to be about 86, 87, 88, 89, 90, 91, 92, 93, 94, 95, 96, 97, 98, and 99 percent homologous to the referent nucleic acid sequence of polypeptide.

Substantial temporal or spatial regulation refers to the expression of a gene within a plant or plant tissue from a plant operable promoter. With reference to temporal regulation, a promoter may be regulated for expression only during specific times during plant cell or tissue or even whole plant growth and development. A promoter which is actively expressing one or more genes only during seed germination would be one example of temporal regulation. Other examples could include promoters which are actively expressing one or more genes only during times when the plant, plant cell or plant tissue is exposed to certain light intensities or during total darkness. Substantial temporal regulation refers to a promoter which is actively expressed at a certain time but which may or may not be completely suppressed at other times, such that expression may still be detected by monitoring for the presence of some indicator such as an enzyme produced from a coding sequence linked to such promoter, or as measured by the increase or decrease in some gene product such as an mRNA produced at various times throughout plant growth, differentiation, and development and/or in response to various environmental stimuli. Substantial spatial regulation refers to the expression of a gene linked to a promoter from which expression proceeds only during growth and development of certain cells or tissues within a plant. For example, a tapetal promoter would only be expected to be expressed during flower growth and development. Similarly, a root specific or root enhanced promoter would only be expected to be expressed from within root cells or root tissues. Substantially spatially regulated also refers to the level of expression from a particular tissue specific promoter in that particular tissue and as related to levels of expression from that or a similar promoter in other tissues, wherein expression may also be detected in tissues other than the particular tissue in which the promoter expression is preferred, but at significantly lower expression levels as measured by the production of an enzyme produced from a coding sequence linked to the promoter or by the appearance of some detectable gene product. Promoters can also be both substantially temporally and substantially spatially regulated together and simultaneously in a coordinately regulated manner.

Synthetic gene: Synthetic genes encoding the *B. thuringiensis* δ-endotoxins of the present invention are those prepared in a manner involving any sort of genetic isolation or manipulation. This includes isolation of the gene from its naturally occurring state, manipulation of the gene as by codon modification (as described herein), or site-specific mutagenesis (as described herein), truncation of the gene or any other manipulative or isolative method.

Terminator: The 3' end transcription termination and polyadenylation sequence.

Transformation: A process of introducing an exogenous DNA sequence (e.g., a vector, or a recombinant DNA molecule) into a cell or protoplast in which that exogenous DNA is incorporated into a chromosome or is capable of autonomous replication.

Transformed cell: A cell which has been altered by the introduction of one or more exogenous DNA molecules into that cell.

Transgene: A gene construct or DNA segment comprising a gene which is desired to be expressed in the recipient cell, tissue or organism. This may include an entire plasmid, or other vector, or may simply include the functional coding section, region, domain, or segment of the transferred DNA construct.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic event: A plant or progeny thereof derived from the insertion of foreign DNA into the nuclear genome of a plant cell or protoplast.

Transgenic plant: A plant or progeny thereof which has been genetically modified to contain and express heterologous DNA sequences as proteins. As specifically exemplified herein, a transgenic soybean plant is genetically modified to contain and express at least one heterologous DNA sequence operably linked to and under the regulatory control of transcriptional control sequences which function in plant cells or tissue or in whole plants. A transgenic plant may also be referred to as a transformed plant. A transgenic plant also refers to progeny of the initial transgenic plant where those progeny contain and are capable of expressing the heterologous coding sequence under the regulatory control of the plant-expressible transcription control sequences described herein.

Vector: A DNA molecule capable of replication in a host cell and/or to which another DNA segment can be operatively linked so as to bring about replication of the linked segment. A plasmid is an exemplary vector.

4.3 Synthesis and Isolation of a Nucleic Acid Segment Encoding a *B. thuringiensis* δ-endotoxin and Plastid Targeting Sequences The present invention discloses novel DNA constructs comprising polynucleotide sequences encoding *B. thuringiensis* δ-endotoxins, as well as plastid targeting sequences. Methods for the construction and expression of synthetic *B. thuringiensis* genes in plants are well known by those of skill in the art and are described in detail in U.S. Pat. No. 5,500,365. The present invention contemplates the use of Cry2A *B. thuringiensis* genes in the transformation of both monocotyledonous and dicotyledonous plants. To potentiate the expression of these genes, the present invention provides DNA constructs comprising polynucleotide segments encoding plastid targeting peptides positioned upstream of the polynucleotide sequences encoding the desired *B. thuringiensis* δ-endotoxins. In particular, sequences encoding *B. thuringiensis* δ-endotoxins lacking substantial Dipteran species inhibitory activity are contemplated.

4.4 Probes and Primers

In one aspect, nucleotide sequence information provided by the invention allows for the preparation of relatively short DNA sequences having the ability to specifically hybridize to gene sequences of the selected polynucleotides disclosed herein. In these aspects, nucleic acid probes of an appropriate length are prepared based on a consideration of selected polypeptide sequences encoding Cry2A δ-endotoxin polypeptides, e.g., a sequence such as that shown in SEQ ID NO:1. These nucleic acid probes may also be prepared based on a consideration of selected polynucleotide sequences encoding a plastid targeting peptide, such as those shown in SEQ ID NO:3, SEQ ID NO:5, SEQ ID NO:7, and SEQ ID NO:9. The ability of such nucleic acid probes to specifically hybridize to a gene sequence encoding a δ-endotoxin polypeptide or a plastid targeting peptide sequence lends to them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. The process may also be used to detect, amplify or mutate a defined segment of the polynucleotide encoding a plastid targeting peptide. Segments of genes related to the polynucleotides encoding the δ-endotoxin polypeptides and plastid targeting peptides of the present invention may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a polynucleotide sequence encoding a crystal protein, such as that shown in SEQ ID NO:1, or sequences that are complementary to at least a 14 to 30 or so long nucleotide stretch of a sequence encoding a plastid targeting peptide, such as those shown in SEQ ID NO:3, SEQ ID NO:5, SEQ ID NO:7, and SEQ ID NO:9.

A size of at least 14 nucleotides in length helps to ensure that the fragment will be of sufficient length to form a duplex molecule that is both stable and selective. Molecules having complementary sequences over segments greater than 14 bases in length are generally preferred. In order to increase stability and selectivity of the hybrid, and thereby improve the quality and degree of specific hybrid molecules obtained, one will generally prefer to design nucleic acid molecules having gene-complementary sequences of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202 (each specifically incorporated herein by reference), or by excising selected DNA fragments from recombinant plasmids containing appropriate inserts and suitable restriction sites.

4.5 Expression Vectors

The present invention also contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region. The coding region may include a segment encoding a *B. thuringiensis* δ-endotoxin and a segment encoding a plastid target peptide. The DNA molecule comprising the expression vector may also contain a functional intron As used herein, the terms "operatively linked" or "operably linked" mean that a promoter is connected to a coding region in such a way that the transcription of that coding region is controlled and regulated by that promoter. Means for operatively linking a promoter to a coding region to regulate both upstream and downstream are well known in the art.

Preferred plant transformation vectors include those derived from a Ti plasmid of *Agrobacterium tumefaciens,* as well as those disclosed, e.g., by Herrera-Estrella (1983), Bevan (1983), Klee (1985) and Eur. Pat Appl. No. EP 0120516 (each specifically incorporated herein by reference).

Promoters that function in bacteria are well known in the art. Exemplary and preferred promoters for the *B. thuringiensis* crystal proteins include the sigA, sigE, and sigK gene promoters. Alternatively, native, mutagenized, heterologous, or recombinant crystal protein-encoding gene promoters themselves can be used.

Where an expression vector of the present invention is to be used to transform a plant, a promoter is selected that has the ability to drive expression in that particular species of plant. Promoters that function in different plant species are also well known in the art. Promoters useful in expressing the polypeptide in plants are those which are inducible, viral, synthetic, or constitutive as described (Odell et al., 1985), and/or temporally regulated, spatially regulated, and spatiotemporally regulated. Preferred promoters include the enhanced CaMV35S promoters, and the FMV35S promoter.

4.5.1 Vectors with Plastid Targeting Peptide-Encoding Segments

In accordance with the present invention, expression vectors designed to specifically potentiate the expression of the polypeptide in the transformed plant may include certain regions encoding plastid targeting peptides (PTP). These regions allow for the cellular processes involved in transcription, translation and expression of the encoded protein to be fully exploited when associated with certain *B. thuringiensis* δ-endotoxins. Such plastid targeting peptides function in a variety of ways, such as for example, by transferring the expressed protein to the cell structure in which it most effectively operates, or by transferring the expressed protein to areas of the cell in which cellular processes necessary for expression are concentrated.

The use of PTPs may also increase the frequency of recovery of morphologically normal plants, and the frequency at which transgenic plants may be recovered. Given that commercially viable expression of both Cry1A and Cry3A-type *B. thuringiensis* δ-endotoxins have been achieved by expression of forms of the proteins that remain localized in the cytosol (i.e. non-targeted forms), expression of non-targeted forms of both Cry2Aa and Cry2Ab were also initially attempted in transgenic cotton, tobacco, and corn.

In corn, non-targeted Cry2Ab expression transformation vectors yield relatively few transgenic events (i.e. independent insertion events into the corn genome) with Cry2Ab expression levels sufficient for commercially acceptable insect control. Moreover, many of the corn transformants expressing non-targeted Cry2Ab exhibited obvious growth defects such as severe reduction in stature (stunting) or severe yellowing of the leaves (chlorosis) that rendered the plants commercially unacceptable. Expression levels of non-targeted Cry2Ab in corn were no higher than approximately 15 ppm, a level minimally required for Cry2Ab-mediated control of European corn borer (ECB).

Although studies involving expression of plastid targeted Cry1A-type *B. thuringiensis* δ-endotoxins in transgenic plants have been described (Wong et al., 1992) , targeting of the non-homologous Cry2A or Cry2A proteins has not previously been described. One report of plastid targeted Cry1Ac expression indicated that such targeting results in little or no increase in Cry1Ac expression (U.S. Pat. No. 5,500,365). Another report indicated that an increase in expression of a plastid targeted form of Cry1Ac required the inclusion of a new 5' untranslated leader sequence (Wong et al., 1992) and that the effect of the leader and targeting sequences on expression was highly dependent on the coding sequence of the structural gene. Wong et al. concluded that inclusion of both the leader sequence and plastid transit peptide increased Cry1Ac expression 18-fold, but the same sequences increased β-glucuronidase expression only 6-fold. Finally, none of the previous reports predicted that plastid targeting would result in increased recovery of morphologically normal *B. thuringiensis* expressing plants.

The present invention discloses that transgenic corn plants expressing Dipteran inactive Cry2A δ-endotoxins, such as Cry2Ab, at levels up to 10-fold higher than required for ECB control were recovered at significantly higher frequencies when a plastid targeted form of the Cry2A was used. In the case of Cry2Ab, elevated expression is critical in obtaining transgenic corn with ECB control since the $LC_{50}$ of Cry2Ab against ECB is significantly higher than the $LC_{50}$ ECB of the Cry1Ab *B. thuringiensis* currently used to control ECB in transgenic corn (U.S. Pat. No. 5,338,544, 1994; MacIntosh et al., 1990; Armstrong et al., 1995).

Increased expression is also especially valuable in that it provides additional protection against development of resistance via a high dose strategy (McGaughey and Whalon, 1993; Roush, 1994). High level expression is even further desirable as it provides sustained insect protection in instances where insecticidal gene expression decreases due to environmental conditions. Additionally and unexpectedly, corn plants transformed with plastid targeted Cry2Ab expression vectors exhibited normal growth and development.

A significant distinction between targeted and non-targeted (cytosolic) expression of Cry2Ab was the dramatic increase in levels of Cry2Ab protein in plants transformed with the plastid targeted Cry2Ab expression vector relative to plants transformed with the cytosolic Cry2Ab vector. This result was very unexpected. Also, in contrast to the teachings of previous work, the invention disclosed herein reveals that enhanced recovery of phenotypically normal transgenic plants can be achieved using the disclosed methods of plastid targeted expression.

An example of a plastid targeting peptide (PTP) is a chloroplast targeting peptide. Chloroplast targeting peptides have been found particularly useful in the glyphosate resistant selectable marker system. In this system, plants transformed to express a protein conferring glyphosate resistance are transformed with a PTP that targets the peptide to the cell's chloroplasts. Glyphosate inhibits the shikimic acid pathway which leads to the biosynthesis of aromatic compounds including amino acids and vitamins. Specifically, glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS). Supplemental EPSPS, conferred via insertion of a transgene encoding this enzyme, allows the cell to resist the effects of the glyphosate. Thus, as the herbicide glyphosate functions to kill the cell by interrupting aromatic amino acid biosynthesis, particularly in the cell's chloroplast, the PTP allows increased resistance to the herbicide by concentrating what glyphosate resistance enzyme the cell expresses in the chloroplast, i.e. in the target organelle of the cell. Exemplary herbicide resistance enzymes include ESPS as noted above, glyphosate oxido-reductase (GOX) and the aroA gene (see U.S. Pat. No. 4,535,060, specifically incorporated herein by reference in its entirety).

PTPs can target proteins to chloroplasts and other plastids. For example, the target organelle may be the amyloplast. Preferred PTPs of the present invention include those targeting both chloroplasts as well as other plastids. Specific examples of preferred PTPs include the maize RUBISCO SSU protein PTP, and functionally related peptides such as PTP1, PTPΔ, and PTP2. These PTPs are exemplified by the polypeptides shown in SEQ ID NO:4, SEQ ID NO:6, SEQ ID NO:8, and SEQ ID NO:10. Polynucleotide sequences encoding for these polypeptides are shown in SEQ ID NO:3, SEQ ID NO:5, SEQ ID NO:7, and SEQ ID NO:9.

Recombinant plants, cells, seeds, and other plant tissues could also be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67–70, 1987). Methods and compositions for obtaining cells containing chloroplasts into which heterologous DNA has been inserted has been described by Daniell et al., U.S. Pat. No. 5,693,507 (1997). McBride et al. (WO 95/24492) disclose localization and expression of genes encoding Cry1A δ-endotoxin protein in tobacco plant chloroplast genomes. As disclosed herein, localization of Cry2Aa to the chloroplast or plastid results in decreased levels of expression as measured by accumulation of Cry2Aa δ-endotoxin, which is in contrast to the improved expression of chloroplast or plastid localized Cry2Ab δ-endotoxin.

4.5.2 Use of Promoters in Expression Vectors

The expression of a gene which exists in double-stranded DNA form involves transcription of messenger RNA (mRNA) from the coding strand of the DNA by an RNA polymerase enzyme, and the subsequent processing of the mRNA primary transcript inside the nucleus. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA. The particular promoter selected should be capable of causing sufficient expression of the enzyme coding sequence to result in the production of an effective insecticidal amount of the *B. thuringiensis* protein.

The 3' non-translated region of the chimeric plant genes of the present invention also contains a polyadenylation signal which functions in plants to cause the addition of adenylate nucleotides to the 3' end of the RNA. Examples of preferred 3' regions are (1) the 3' transcribed, non-translated regions containing the polyadenylation signal of Agrobacterium tumor-inducing (Ti) plasmid genes, such as the nopaline synthase (NOS) gene and (2) the 3' ends of plant genes such as the pea ssRUBISCO E9 gene (Fischhoff et al., 1987).

A promoter is selected for its ability to direct the transformed plant cell's or transgenic plant's transcriptional activity to the coding region, to ensure sufficient expression of the enzyme coding sequence to result in the production of insecticidal amounts of the *B. thuringiensis* protein. Structural genes can be driven by a variety of promoters in plant tissues. Promoters can be near-constitutive (i.e. they drive transcription of the transgene in all tissue), such as the CaMV35S promoter, or tissue-specific or developmentally specific promoters affecting dicots or monocots. Where the promoter is a near-constitutive promoter such as CaMV35S or FMV35S, increases in polypeptide expression are found in a variety of transformed plant tissues and most plant organs (e.g., callus, leaf, seed and root). Enhanced or duplicate versions of the CaMV35S and FMV35S promoters are particularly useful in the practice of this invention (Kay et al., 1987; Rogers, U.S. Pat. No. 5,378,619).

Those skilled in the art will recognize that there are a number of promoters which are active in plant cells, and have been described in the literature. Such promoters may be obtained from plants or plant viruses and include, but are not limited to, the nopaline synthase (NOS) and octopine synthase (OCS) promoters (which are carried on tumor-inducing plasmids of *A. tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), the rice Act1 promoter and the Figwort Mosaic Virus (FMV) 35S promoter. All of these promoters have been used to create various types of DNA constructs which have been expressed in plants (see e.g., McElroy et al., 1990, U.S. Pat. No. 5,463,175).

In addition, it may also be preferred to bring about expression of the *B. thuringiensis* δ-endotoxin in specific tissues of the plant by using plant integrating vectors containing a tissue-specific promoter. Specific target tissues may include the leaf, stem, root, tuber, seed, fruit, etc., and the promoter chosen should have the desired tissue and developmental specificity. Therefore, promoter function should be optimized by selecting a promoter with the desired tissue expression capabilities and approximate promoter strength and selecting a transformant which produces the desired insecticidal activity in the target tissues. This selection approach from the pool of transformants is routinely employed in expression of heterologous structural genes in plants since there is variation between transformants containing the same heterologous gene due to the site of gene insertion within the plant genome (commonly referred to as "position effect"). In addition to promoters which are known to cause transcription (constitutive or tissue-specific) of DNA in plant cells, other promoters may be identified for use in the current invention by screening a plant cDNA library for genes which are selectively or preferably expressed in the target tissues and then determine the promoter regions.

An exemplary tissue-specific promoter is the lectin promoter, which is specific for seed tissue. The lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990). An expression vector containing a coding region that encodes a polypeptide of interest can be engineered to be under control of the lectin promoter and that vector may be introduced into plants using, for example, a protoplast transformation method (Dhir et al., 1991). The expression of the polypeptide would then be directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Other exemplary tissue-specific promoters are corn sucrose synthetase 1 (Yang et al, 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (McBride and Summerfelt, 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al., (1987). Chloroplast or plastid specific promoters are known in the art (Daniell et al., U.S. Pat. No. 5,693,507; herein incorporated by reference), for example promoters obtainable from chloroplast genes, such as the psbA gene from spinach or pea, the rbcL and atpB promoter region from maize, and rRNA promoters. Any chloroplast or plastid operable promoter is within the scope of the present invention.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs wherein the non-translated region is derived from the 5' non-translated sequence that accompanies the promoter sequence. As shown below, a plant gene leader sequence which is useful in the present invention is the petunia heat shock protein 70 (hsp70) leader (Winter et al., 1988).

An exemplary embodiment of the invention involves the plastid targeting or plastid localization of the *B. thuringiensis* amino acid sequence. Plastid targeting sequences have been isolated from numerous nuclear encoded plant genes and have been shown to direct importation of cytoplasmically synthesized proteins into plastids (reviewed in Keegstra and Olsen, 1989). A variety of plastid targeting sequences, well known in the art, including but not limited to ADPGPP, EPSP synthase, or ssRUBISCO, may be utilized in practicing this invention. In alternative embodiments preferred, plastidic targeting sequences (peptide and nucleic acid) for monocotyledonous crops may consist of a genomic coding fragment containing an intron sequence as well as a duplicated proteolytic cleavage site in the encoded plastidic targeting sequences.

The most preferred nucleic acid sequence, referred to herein as zmSSU PTP (SEQ ID NO:3), consists of a genomic coding fragment containing an intron sequence as well as a duplicated proteolytic cleavage site in the encoded plastidic targeting sequences, was derived from plastid targeting sequence zmS1 (Russell et al., 1993). Direct translational fusions of zmSSU PTP peptide sequence (SEQ ID NO:4) to the amino terminus of the sequences are useful in obtaining elevated levels of the polypeptide in transgenic maize. In-frame fusions of the zmSSU PTP nucleic acid sequence (SEQ ID NO:3) to the cry2Ab gene (SEQ ID NO:1) can be effected by ligation of the NcoI site at the 3' (C-terminal encoding) end of the zmSSU PTP sequence with the 5' NcoI site (N-terminal encoding) of the cry2Ab sequence.

The preferred sequence for dicotyledonous crops referred to herein as PTP2 (SEQ ID NO:9), consists of a genomic coding fragment containing the chloroplast targeting peptide sequence from the EPSP synthase gene of *Arabidopsis thaliana* in which the transit peptide cleavage site of the pea ssRUBISCO PTP replaces the native EPSP synthase PTP cleavage site (Klee et al., 1987).

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of Agrobacterium tumor-inducing (Ti) plasmid genes, such as the nopaline synthase (NOS) gene and (2) plant genes such as the pea ssRUBISCO E9 gene (Fischhoff et al., 1987).

4.5.3 Use of Introns in Expression Vectors

For optimized expression in monocotyledonous plants, an intron may also be included in the DNA expression construct. Such an intron is typically placed near the 5'-end of the mRNA in untranslated sequence. This intron could be obtained from, but not limited to, a set of introns consisting of the maize Heat Shock Protein (HSP) 70 intron (U.S. Pat. No. 5,424,412; 1995), the rice ActI intron (McElroy et al., 1990), the Adh intron 1 (Callis et al., 1987), or the sucrose synthase intron (Vasil et al., 1989). As shown herein, the maize HSP70 intron is useful in the present invention.

4.5.4 Use of Terminators in Expression Vectors

RNA polymerase transcribes a nuclear genome coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). For coding sequences introduced into a chloroplast or plastid, or into a chloroplast or plastid genome, mRNA transcription termination is similar to methods well known in the bacterial gene expression art. For example, either in a polycistronic or a monocistronic sequence, transcription can be terminated by stem and loop structures or structures similar to rho dependent sequences.

Constructs will typically include the gene of interest along with a 3' end DNA sequence that acts as a signal to terminate transcription and, in constructs intended for nuclear genome expression, allow for the polyadenylation of the resultant mRNA. The most preferred 3' elements are contemplated to be those from the nopaline synthase gene of *A. tumefaciens* (nos 3' end) (Bevan et al., 1983), the terminator for the T7 transcript from the octopine synthase gene OF *A. tumefaciens,* and the 3' end of the protease inhibitor i or ii genes from potato or tomato. Regulatory elements such as TMV Ω element (Gallie, et al., 1989), may further be included where desired.

4.5.5 Other Expression-Enhancing Elements

Another type of element which can regulate gene expression is the DNA sequence between the transcription initiation site and the start of the coding sequence, termed the untranslated leader sequence. The leader sequence can influence gene expression. Compilations of leader sequences have been made to predict optimum or sub-optimum sequences and generate "consensus" and preferred leader sequences (Joshi, 1987). Preferred leader sequences are contemplated to include those which comprise sequences predicted to direct optimum expression of the linked structural gene, i.e. to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred. One particularly useful leader may be the petunia HSP70 leader.

Transcription enhancers or duplications of enhancers could be used to increase expression. These enhancers often are found 5' to the start of transcription in a promoter that functions in eukaryotic cells, but can often be inserted in the forward or reverse orientation 5' or 3' to the coding sequence. Examples of enhancers include elements from the CaMV 35S promoter, octopine synthase genes (Ellis et al., 1987), the rice actin gene, and promoter from non-plant eukaryotes (e.g., yeast; Ma et al., 1988).

4.5.6 Multigene Vector Constructs and IRES In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

Constructs intended for expression from within a chloroplast or plastid utilizing chloroplast or plastid specific transcriptional and translational machinery can contain either mono- or polycistronic sequences.

4.5.7 Construction of the Expression Vector

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *A. tumefaciens* described (Rogers et al., 1987). However, several other plant integrating vector systems are known to function in plants including pCaMVCN transfer control vector described (Fromm et al., 1986). pCaMVCN (available from Pharmacia, Piscataway, NJ) includes the CaMV35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e. the chimeric gene containing the nopaline synthase promoter, Tn5 neomycin phosphotransferase II (nptII) and nopaline synthase 3' non-translated region described (Rogers et al., 1988).

Means for preparing expression vectors are well known in the art. Expression (transformation) vectors used to transform plants and methods of making those vectors are described in U.S. Pat. Nos. 4,971,908, 4,940,835, 4,769,061 and 4,757,011 (each of which is specifically incorporated herein by reference). Those vectors can be modified to include a coding sequence in accordance with the present invention.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a polynucleotide encoding a *B. thuringiensis* δ-endotoxin or a functional equivalent of such a polynucleotide. In accordance with such embodiments, a coding region comprising the DNA sequence of SEQ ID NO:1 is also preferred.

Specific *B. thuringiensis* δ-endotoxin polypeptide-encoding genes that have been shown to successfully transform plants in conjunction with plastid targeting peptide-encoding genes, to express the *B. thuringiensis* δ-endotoxins at high levels are those genes comprised within the plasmid vectors. Preferred plasmids containing plastid targeting sequences include pMON30464, pMON33827, pMON33828, pMON33829. These plasmids are encoded for by the sequences shown in SEQ ID NO:16, SEQ ID NO:13, SEQ ID NO:14, SEQ ID NO:15. More preferably, plants may be successfully transformed with any vector containing expression cassettes comprising the nucleotide sequences of nucleotide 1781 to 5869 of SEQ ID NO:16, nucleotide 17 to 3182 of SEQ ID NO:13, nucleotide 17 to 3092 of SEQ ID NO:14 or nucleotide 17 to 3155 of SEQ ID NO:15.

The work described herein has identified methods of potentiating in planta expression of *B. thuringiensis* δ-endotoxins, which confer resistance to insect pathogens when incorporated into the nuclear, plastid, or chloroplast genome of susceptible plants. U.S. Pat. No. 5,500,365 (specifically incorporated herein by reference) describes a method for synthesizing plant genes to optimize the expression level of the protein for which the synthesized gene encodes. This method relates to the modification of the structural gene sequences of the exogenous transgene, to make them more "plant-like" and therefore more likely to be translated and expressed by the plant. A similar method for enhanced expression of transgenes, preferably in monocotyledonous plants, is disclosed in U.S. Pat. No. 5,689,052 (specifically incorporated herein by reference). Agronomic, horticultural, ornamental, and other economically or commercially useful plants can be made in accordance with the methods described herein, to express *B. thuringiensis* δ-endotoxins at levels high enough to confer resistance to insect pathogens.

Such plants may co-express the *B. thuringiensis* δ-endotoxin polypeptide along with other antifungal, antibacterial, or antiviral pathogenesis-related peptides, polypeptides, or proteins; insecticidal proteins; proteins conferring herbicide resistance; and proteins involved in improving the quality of plant products or agronomic performance of plants. Simultaneous co-expression of multiple proteins in plants is advantageous in that it exploits more than one mode of action to control plant pathogenic damage. This can minimize the possibility of developing resistant pathogen strains, broaden the scope of resistance, and potentially result in a synergistic insecticidal effect, thereby enhancing plants ability to resist insect infestation (WO 92/17591).

Specifically contemplated for use in accordance with the present invention are vectors which include the ocs enhancer element. This element was first identified as a 16 bp palindromic enhancer from the octopine synthase (ocs) gene of Agrobacterium (Ellis et al., 1987), and is present in at least 10 other promoters (Bouchez et al., 1989). It is proposed that the use of an enhancer element, such as the ocs element and particularly multiple copies of the element, may be used to increase the level of transcription from adjacent promoters when applied in the context of monocot transformation.

It is contemplated that introduction of large DNA sequences comprising more than one gene may be desirable. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al. (1996).

Ultimately, the most desirable DNA segments for introduction into a monocot genome may be homologous genes or gene families which encode a desired trait (for example, increased yield), and which are introduced under the control of novel promoters or enhancers, etc., or perhaps even homologous or tissue specific (e.g., root-collar/sheath-, whorl-, stalk-, earshank-, kernel- or leaf-specific) promoters or control elements. Indeed, it is envisioned that a particular use of the present invention may be the production of transformants comprising a transgene which is targeted in a tissue-specific manner. For example, insect resistant genes may be expressed specifically in the whorl and collar/sheath tissues which are targets for the first and second broods, respectively, of ECB. Likewise, genes encoding proteins with particular activity against rootworm may be targeted directly to root tissues.

Vectors for use in tissue-specific targeting of gene expression in transgenic plants typically will include tissue-specific promoters and also may include other tissue-specific control elements such as enhancer sequences. Promoters which direct specific or enhanced expression in certain plant tissues will be known to those of skill in the art in light of the present disclosure.

It also is contemplated that tissue specific expression may be functionally accomplished by introducing a constitutively expressed gene (all tissues) in combination with an antisense gene that is expressed only in those tissues where the gene product is not desired. For example, a gene coding for the crystal toxin protein from *B. thuringiensis* may be introduced such that it is expressed in all tissues using the 35S promoter from Cauliflower Mosaic Virus. Alternatively, a rice actin promoter or a histone promoter from a dicot or monocot species also could be used for constitutive expression of a gene. Furthermore, it is contemplated that promoters combining elements from more than one promoter may be useful. For example, U.S. Pat. No. 5,491,288 discloses combining a Cauliflower Mosaic Virus promoter with a histone promoter. Therefore, expression of an antisense transcript of the Bt gene in a maize kernel, using for example a zein promoter, would prevent accumulation of the δ-endotoxin in seed. Hence the protein encoded by the introduced gene would be present in all tissues except the kernel. It is specifically contemplated by the inventors that a similar strategy could be used with the instant invention to direct expression of a screenable or selectable marker in seed tissue.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may this be localized using the techniques of molecular biology known to those of skill in the art.

It is contemplated that expression of some genes in transgenic plants will be desired only under specified conditions. For example, it is proposed that expression of certain genes that confer resistance to environmentally stress factors such as drought will be desired only under actual stress conditions. It further is contemplated that expression of such genes throughout a plants development may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. For example, synthesis of abscisic acid (ABA) is induced by certain environmental factors, including but not limited to water stress. A number of genes have been shown to be induced by ABA (Skriver and Mundy, 1990). It also is expected that expression of genes conferring resistance to insect predation would be desired only under conditions of actual insect infestation. Therefore, for some desired traits, inducible expression of genes in transgenic plants will be desired.

It is proposed that, in some embodiments of the present invention, expression of a gene in a transgenic plant will be desired only in a certain time period during the development of the plant. Developmental timing frequently is correlated with tissue specific gene expression. For example expression of zein storage proteins is initiated in the endosperm about 15 days after pollination.

It also is contemplated that it may be useful to target DNA itself with a cell. For example, it may be useful to target introduced DNA to the nucleus as this may increase the frequency of transformation. Within the nucleus itself it would be useful to target a gene in order to achieve site specific integration. For example, it would be useful to have a gene introduced through transformation replace an existing gene in the cell.

4.6 Identification and Isolation of Insecticidal *B. thuringiensis* δ-Endotoxins and Genes It is contemplated that the method described in this invention could be used to obtain substantially improved expression of a number of novel *B. thuringiensis* endotoxins isolated as described below. Identification of new *Bacillus thuringiensis* strains encoding crystalline endotoxins with insecticidal activity has been described previously (Donovan et al., 1992). Isolation of the *B. thuringiensis* endotoxin, followed by amino terminal amino acid sequencing, back-translation of the amino acid sequence to design an oligonucleotide probe or use of a related *B. thuringiensis* gene as a probe, followed by cloning of the gene encoding the endotoxin by hybridization are familiar to those skilled in the art and have been described, (see e.g., Donovan et al., 1992); U.S. Pat. No. 5,264,364, each specifically incorporated herein by reference.

Improved expression of Dipteran-inactive Cry2A *B. thuringiensis* δ-endotoxins in transgenic plants can be achieved via the methods described in this invention. One protein for which improved expression is obtained is Cry2Ab.

Previous work indicated that certain Cry2A δ-endotoxins were capable of wider host range specificity than other closely related Cry2A δ-endotoxins wherein not only Lepidopteran species, but Dipteran species also were particularly susceptible to very low toxin doses. In contrast, the closely related Cry2A endotoxins not displaying substantial Dipteran inhibitory activity were thus shown to be more narrow in their host range specificity (Widner et al., 1989, J. Bacteriol. 171:965–974; Widner et al. (a), 1990, J. Bacteriol. 172:2826–2832). These works indicated that Cry2Ab as used herein does not totally lack Dipteran inhibitory activity, but is simply much less potent than other closely related Cry2A *B. thuringiensis* δ-endotoxins. Those works indicated that Cry2Ab in particular was much less effective than Cry2Aa, and hence lacked Dipteran activity when tested against *Aedes egyptii.* There is no one single acceptable means for distinguishing between closely related δ-endotoxins, however, as indicated herein, selection of an appropriate Cry2A could be accomplished by using one or a combination of several methods including but not limited to comparisons in overall amino acid sequence homology, narrowly focused similarity comparisons between Cry2A's in the region specified by amino acid sequence 307–382, or based on IC50 data. Widner et al. demonstrated 50–100 times more Cry2Ab than Cry2Aa was required to obtain a similar IC50 effect on a Dipteran species. Thus, the range of susceptibility of a Dipteran species toward a Cry2A protein could be used as one means of measuring and distinguishing target insect susceptibility differences between different classes of Cry2A proteins. For example, an IC50 PPM value of about 3-fold greater than that exhibited by Cry2Aa against *Aedes egyptii* could be utilized as a feature for excluding certain Cry2A proteins as lacking substantial Dipteran species inhibitory activity. However, utilizing an approach based on IC50 inhibitory activity ranges should be used with caution, as these values are very dependent upon a number of highly variable conditions including but not limited to the methods and materials used for assaying the proteins and the physical conditioning of the insects assayed. An alternative means for distinguishing Cry2A δ-endotoxins lacking substantial Dipteran species inhibitory activity from δ-endotoxins which are not within the scope of the present invention could encompass excluding Cry2A proteins which are greater than about 87% similar in amino acid sequence to Cry2Aa, or more preferentially excluding Cry2A proteins which are greater than about 90% similar in amino acid sequence to Cry2Aa. In particular, the region of Cry2Aa corresponding to amino acid residues from about 307 to about 382 are believed to be critical for the Dipteran inhibitory activity of the protein, and when substituted for the complementary region of dissimilarity in Cry2Ab, confers Dipteran inhibitory activity to Cry2Ab protein. Thus, an additional means for distinguishing Cry2A δ-endotoxins which are within the scope of the present invention could encompass a similarity comparison of this region of the protein, taking into consideration the level of homology. to be avoided when comparing any particular Cry2A δ-endotoxins to this region in Cry2Aa. The variable amino acids within this 76 amino acid sequence domain, Cry2A δ-endotoxins which are intended to be within the scope of the present invention would preferably be those which are more than from about 80 to about 99 percent similar to Cry2Aa within this sequence, or more preferably those which are more than from about 60 to about 79 percent similar to Cry2Aa within this sequence, or those which are more than from about 40 to about 59 percent similar to Cry2Aa within this sequence, or even more preferably those which are more than from about 24 to about 39 percent similar to Cry2Aa within this sequence, or most preferably those Cry2A δ-endotoxins which are more than from about 0 to about 23 percent similar to Cry2Aa within this sequence.

4.7 Transformed Plant Cells and Transgenic Plants

A plant transformed with an expression vector of the present invention is also contemplated. A transgenic plant derived from such a transformed or transgenic cell is also contemplated. Those skilled in the art will recognize that a chimeric plant gene containing a structural coding sequence of the present invention can be inserted into the genome of a plant by methods well known in the art. Such methods for DNA transformation of plant cells include Agrobacterium-mediated plant transformation, the use of liposomes, transformation using viruses or pollen, electroporation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as infection by *A. tumefaciens* and related Agrobacterium strains, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

4.7.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation is well-known to those of skill in the art. To effect transformation by electroporation, one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner, rendering the cells more susceptible to transformation. Such cells would then be recipient to DNA transfer by electroporation, which may be carried out at this stage, and transformed cells then identified by a suitable selection or screening protocol dependent on the nature of the newly incorporated DNA.

4.7.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like. Using these particles, DNA is carried through the cell wall and into the cytoplasm on the surface of small metal particles as described (Klein et al., 1987; Klein et al., 1988; Kawata et al., 1988). The metal particles penetrate through several layers of cells and thus allow the transformation of cells within tissue explants. The microprojectile bombardment method is preferred for the identification of chloroplast or plastid directed transformation events.

An advantage of microprojectile bombardment, in addition to it being an effective means of reproducibly stably transforming plant cells, is that neither the isolation of protoplasts (Cristou et al., 1988) nor the susceptibility to Agrobacterium infection is required. An illustrative embodiment of a method for delivering DNA into plant cells by acceleration is a Biolistics Particle Delivery System, which can be used to propel particles coated with DNA or cells through a screen, such as a stainless steel or Nytex screen, onto a filter surface covered with the plant cultured cells in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature plant embryos.

Accordingly, it is contemplated that one may desire to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

The methods of particle-mediated transformation is well-known to those of skill in the art. U.S. Pat. No. 5,015,580 (specifically incorporated herein by reference) describes the transformation of soybeans using such a technique.

4.7.3 Agrobacterium-Mediated Transfer

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). The genetic engineering of cotton plants using Agrobacterium-mediated transfer is described in U.S. Pat. No. 5,004,863 (specifically incorporated herein by reference); like transformation of lettuce plants is described in U.S. Pat. No. 5,349,124 (specifically incorporated herein by reference); and the Agrobacterium-mediated transformation of soybean is described in U.S. Pat. No. 5,416,011 (specifically incorporated herein by reference). Further, the integration of the Ti-DNA is a relatively precise process resulting in few rearrangements. The region of DNA to be transferred is defined by the border sequences, and intervening DNA is usually inserted into the plant genome as described (Spielmann et al, 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant varieties where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Other monocots recently have also been transformed with Agrobacterium. Included in this group are corn (Ishida et al) and rice (Cheng et al.).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

An independent segregant may be preferred when the plant is commercialized as a hybrid, such as corn. In this case, an independent segregant containing the gene is crossed with another plant, to form a hybrid plant that is heterozygous for the gene of interest.

An alternate preference is for a transgenic plant that is homozygous for the added structural gene; i.e. a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for gene of interest activity and mendelian inheritance indicating homozygosity relative to a control (native, non-transgenic) or an independent segregant transgenic plant.

Two different transgenic plants can be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see e.g., Potrykus et al., 1985; Lorz et al., 1985; Fromm et al., 1985; Uchimiya et al., 1986; Callis et al., 1987; Marcotte et al., 1988).

Application of these systems to different plant germplasm depends upon the ability to regenerate that particular plant variety from protoplasts. Illustrative methods for the regeneration of cereals from protoplasts are described (see, e.g., Fujimura et al., 1985; Toriyama et al., 1986; Yamada et al., 1986; Abdullah et al., 1986).

To transform plant germplasm that cannot be successfully regenerated from protoplasts, other ways to introduce DNA into intact cells or tissues can be utilized. For example, regeneration of cereals from immature embryos or explants can be effected as described (Vasil, 1988).

4.8 Gene Expression in Plants

Unmodified bacterial genes are often poorly expressed in transgenic plant cells. Plant codon usage more closely resembles that of humans and other higher organisms than unicellular organisms, such as bacteria. Several reports have disclosed methods for improving expression of recombinant genes in plants ( Murray et al., 1989; Diehn et al., 1996; Iannacone et al., 1997; Rouwendal et al., 1997; Futterer et al., 1997; and Futterer and Hohn, 1996). These reports disclose various methods for engineering coding sequences to represent sequences which are more efficiently translated based on plant codon frequency tables, improvements in codon third base position bias, using recombinant sequences which avoid suspect polyadenylation or A/T rich domains or intron splicing consensus sequences. While these methods for synthetic gene construction are notable, synthetic genes of the present invention were prepared according to the method of Brown et al. (U.S. Pat. No. 5,689,052; 1997), which is herein incorporated in its entirety by reference. Thus, the present invention provides a method for preparing synthetic plant genes express in planta a desired protein product at levels significantly higher than the wild-type genes. Briefly, according to Brown et al., the frequency of rare and semi-rare monocotyledonous codons in a polynucleotide sequence encoding a desired protein are reduced and replaced with more preferred monocotyledonous codons. Enhanced accumulation of a desired polypeptide encoded by a modified polynucleotide sequence in a monocotyledonous plant is the result of increasing the frequency of preferred codons by analyzing the coding sequence in successive six nucleotide fragments and altering the sequence based on the frequency of appearance of the six-mers as to the frequency of appearance of the rarest 284, 484, and 664 six-mers in monocotyledonous plants. Furthermore, Brown et al. disclose the enhanced expression of a recombinant gene by applying the method for reducing the frequency of rare codons with methods for reducing the occurrence of polyadenylation signals and intron splice sites in the nucleotide sequence, removing self-complementary sequences in the nucleotide sequence and replacing such sequences with nonself-complementary nucleotides while maintaining a structural gene encoding the polypeptide, and reducing the frequency of occurrence of 5'-CG-3' dinucleotide pairs in the nucleotide sequence. These steps are performed sequentially and have a cumulative effect resulting in a nucleotide sequence containing a preferential utilization of the more-preferred monocotyledonous codons for monocotyledonous plants for a majority of the amino acids present in the desired polypeptide.

The work described herein has identified methods of potentiating in planta expression of *B. thuringiensis* δ-endotoxins, which confer resistance to insect pathogens when incorporated into the nuclear, plastid, or chloroplast genome of susceptible plants. U.S. Pat. No. 5,500,365 (specifically incorporated herein by reference) describes a method for synthesizing plant genes to optimize the expression level of the protein for which the synthesized gene encodes. This method relates to the modification of the structural gene sequences of the exogenous transgene, to make them more "plant-like" and therefore more likely to be translated and expressed by the plant, monocot or dicot. However, the method as disclosed in U.S. Pat. No. 5,689,052 provides for enhanced expression of transgenes, preferably in monocotyledonous plants.

4.9 Production of Insect-Resistant Transgenic Plants

Thus, the amount of a gene coding for a polypeptide of interest (i.e. a bacterial crystal protein or δ-endotoxin polypeptide and a plastid targeting peptide) can be increased in plants by transforming those plants using transformation methods such as those disclosed herein at Section 4.7. In particular, chloroplast or plastid transformation can result in desired coding sequences being present in up to about 10,000 copies per cell in tissues containing these subcellular organelle structures (McBride et al., Bio/Technology 13:362–365, 1995).

DNA can also be introduced into plants by direct DNA transfer into pollen as described (Zhou et al., 1983; Hess, 1987). Expression of polypeptide coding genes can be obtained by injection of the DNA into reproductive organs of a plant as described (Pena et al., 1987). DNA can also be injected directly into the cells of immature embryos and the rehydration of desiccated embryos as described (Neuhaus et al., 1987; Benbrook et al, 1986).

4.9.1 Selection of Transformed Cells

After effecting delivery of exogenous DNA to recipient cells, the next step to obtain a transgenic plant generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

An exemplary embodiment of methods for identifying transformed cells involves exposing the transformed cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing. One example of a preferred marker gene confers resistance to glyphosate. When this gene is used as a selectable marker, the putatively transformed cell culture is treated with glyphosate. Upon treatment, transgenic cells will be available for further culturing while sensitive, or non-transformed cells, will not. This method is described in detail in U.S. Pat. No. 5,569,834, which is specifically incorporated herein by reference. Another example of a preferred selectable marker system is the neomycin phosphotransferase (nptII) resistance system by which resistance to the antibiotic kanamycin is conferred, as described in U.S. Pat. No. 5,569,834 (specifically incorporated herein by reference). Again, after transformation with this system, transformed cells will be available for further culturing upon treatment with kanamycin, while non-transformed cells will not. Yet another preferred selectable marker system involves the use of a gene construct conferring resistance to paromomycin. Use of this type of a selectable marker system is described in U.S. Pat. No. 5,424,412 (specifically incorporated herein by reference).

All contemplated assays are nondestructive and transformed cells may be cultured further following identification. Another screenable marker which may be used is the gene coding for green fluorescent protein.

Transplastonomic selection (selection of plastid or chloroplast transformation events) is simplified by taking advantage of the sensitivity of chloroplasts or plastids to spectinomycin, an inhibitor of plastid or chloroplast protein synthesis, but not of protein synthesis by the nuclear genome encoded cytoplasmic ribosomes. Spectinomycin prevents the accumulation of chloroplast proteins required for photosynthesis and so spectinomycin resistant transformed plant cells may be distinguished on the basis of their difference in color: the resistant, transformed cells are green, whereas the sensitive cells are white, due to inhibition of plastid-protein synthesis. Transformation of chloroplasts or plastids with a suitable bacterial aad gene, or with a gene encoding a spectinomycin resistant plastid or chloroplast functional ribosomal RNA provides a means for selection and maintenance of transplastonomic events (Maliga, Trends in Biotechnology 11:101–106, 1993).

It is further contemplated that combinations of screenable and selectable markers will be useful for identification of transformed cells. In some cell or tissue types a selection agent, such as glyphosate or kanamycin, may either not provide enough killing activity to clearly recognize transformed cells or may cause substantial nonselective inhibition of transformants and nontransformants alike, thus causing the selection technique to not be effective. It is proposed that selection with a growth inhibiting compound, such as glyphosate at concentrations below those that cause 100% inhibition followed by screening of growing tissue for expression of a screenable marker gene such as kanamycin would allow one to recover transformants from cell or tissue types that are not amenable to selection alone. It is proposed that combinations of selection and screening may enable one to identify transformants in a wider variety of cell and tissue types.

4.9.2 Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al, 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region encoding a *B. thuringiensis* δ-endotoxin polypeptide and a plastid targeting peptide. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the *B. thuringiensis* transgene.

4.10 Identification of Transgenic Plant Events with Insect Tolerance

To identify a transgenic plant expressing high levels of the δ-endotoxin of interest, it is necessary to screen the herbicide or antibiotic resistant transgenic, regenerated plants ($R_0$ generation) for insecticidal activity and/or expression of the gene of interest. This can be accomplished by various methods well known to those skilled in the art, including but not limited to: 1) obtaining small tissue samples from the transgenic $R_0$ plant and directly assaying the tissue for activity against susceptible insects in parallel with tissue derived from a non-expressing, negative control plant. For example, $R_0$ transgenic corn plants expressing *B. thuringiensis* endotoxins such as Cry2Ab can be identified by assaying leaf tissue derived from such plants for activity against ECB; 2) analysis of protein extracts by enzyme linked immunoassays (ELISAs) specific for the gene of interest (Cry2Ab); or 3) reverse transcriptase PCR™ (RT PCR™) to identify events expressing the gene of interest.

4.11 Isolating Homologous Gene and Gene Fragments

The genes and δ-endotoxins according to the subject invention include not only the full length sequences disclosed herein but also fragments of these sequences, or fusion proteins, which retain the characteristic insecticidal activity of the sequences specifically exemplified herein.

It should be apparent to a person of skill in this art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these δ-endotoxins.

Equivalent δ-endotoxins and/or genes encoding these δ-endotoxins can also be isolated from Bacillus strains and/or DNA libraries using the teachings provided herein. For example, antibodies to the δ-endotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying insecticidal δ-endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}p$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxin, as well as enzymes such as hydrolyses or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementary between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, more than one coding nucleotide triplet (codon) can be used for most of the amino acids used to make proteins. Therefore different nucleotide sequences can code for a particular amino acid. Thus, the amino acid sequences of the *B. thuringiensis* δ-endotoxins and peptides, and the plastid targeting peptides and the polynucleotides which code for them, can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a gene encoding a δ-endotoxin and gene encoding a plastid targeting peptide, as discussed in the present invention. Such mutants can be made by techniques well known to persons skilled in the art. For example, UV irradiation can be used to prepare mutants of host organisms. Likewise, such mutants may include asporogenous host cells which also can be prepared by procedures well known in the art.

4.12 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Such procedures may favorably change the protein's biochemical and biophysical characteristics or its mode of action. These include, but are not limited to: 1) improved δ-endotoxin formation, 2) improved protein stability or reduced protease degradation, 3) improved insect membrane receptor recognition and binding, 4) improved oligomerization or channel formation in the insect midgut endothelium, and 5) improved insecticidal activity or insecticidal specificity due to any or all of the reasons stated above.

4.13 Biological Functional Equivalents

Modification and changes may be made in the structure of the peptides of the present invention and DNA segments which encode them and still obtain a functional molecule that encodes a protein or peptide with desirable characteristics. The biologically functional equivalent peptides, polypeptides, and proteins contemplated herein should possess about 80% or greater sequence similarity, preferably about 85% or greater sequence similarity, and most preferably about 90% or greater sequence similarity, to the sequence of, or corresponding moiety within, the fundamental cry2Ab amino acid sequence.

The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 3.

TABLE 3

| Amino Acid | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | GIy | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

TABLE 3-continued

| Amino Acid | | | Codons |
|---|---|---|---|
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Polynucleotides encoding δ-endotoxins derived from *B. thuringiensis* are known by those skilled in the art, to be poorly expressed when incorporated into the nuclear DNA of transgenic plants (reviewed by Diehn et al., 1996). Preferably, a nucleotide sequence encoding the δ-endotoxin of interest is designed essentially as described in U.S. Pat. Nos. 5,500,365 and 5,689,052 (each specifically incorporated herein by reference). Examples of nucleotide sequences useful for expression include but are not limited to, cry2Ab (SEQ ID NO:1).

Peptides, polypeptides, and proteins biologically functionally equivalent to Cry2Ab include amino acid sequences containing conservative amino acid changes in the fundamental sequence shown in SEQ ID NO:2. In such amino acid sequences, one or more amino acids in the fundamental sequence is (are) substituted with another amino acid(s), the charge and polarity of which is similar to that of the native amino acid, i.e. a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequence can be made by substituting one amino acid within one of these groups with another amino acid within the same group. Biologically functional equivalents of cry2Ab can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of cry2Ab.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Increased Expression of Cry2Ab by Targeted Vectors

Expression of the Cry2Ab protein in corn plants transformed with targeted and non-targeted Cry2Ab expression vectors was compared and was significantly higher in plants with the targeted vector. Untargeted Cry2Ab plant expression vectors pMON26800 and pMON30463 contain an expression cassette composed of an enhanced CaMV35S promoter, a maize hsp70 intron, a synthetic cry2Ab gene with translational initiation and termination codons (SEQ ID NO:1), and a nopaline synthase polyadenylation site.

The targeted plant expression vector pMON30464 (SEQ ID NO:16) contains an expression cassette including enhanced CaMV35S promoter, a maize hsp70 intron, a maize ssRUBISCO chloroplast transit peptide (SEQ ID NO:3) fused in frame to a synthetic cry2Ab gene, and a nopaline synthase polyadenylation site.

All vectors (pMON26800, pMON30463, and pMON30464) also contain a cassette conferring paromomycin resistance to transformed plant tissue. In the case of pMON26800, this cassette consists of an enhanced CaMV35S promoter , a maize hsp70 intron, a neomycin phosphotransferase gene with a translational initiation and termination codons, and a nopaline synthase polyadenylation site. In the case of pMON30463 and pMON30464, this cassette consists of a CaMV35S promoter, a neomycin phosphotransferase gene with a translational initiation and termination codons, and a nopaline synthase polyadenylation site. Transgenic corn plants resistant to paromomycin were derived essentially as described in U.S. Pat. No. 5,424,412 (specifically incorporated herein by reference).

Leaf tissue from independently transformed transgenic events in the $R_0$ stage was subjected to quantitative analysis of Cry2Ab protein levels by a quantitative ELISA assay. This ELISA used a direct sandwich technique that used a monoclonal capture antibody raised against Cry2Aa, a different Cry2Aa monoclonal antibody conjugated to alkaline phosphatase as the secondary antibody, and purified Cry2Aa protein as a standard.

Comparison of Cry2Ab expression levels in pMON30463 (non-targeted) and pMON30464 (targeted) corn plants show that non-targeted Cry2Ab expression does not exceed 15 ppm while targeted expression is frequently higher than 100 ppm (Table 4). Protein blot analyses confirm that the increased level of cross reactive material produced by pMON30464 (targeted) were due to increased accumulation of an approximately Mr 71,000 protein that co-migrates with Cry2Ab produced by pMON30463 (non-targeted) and Cry2Aa standard from *B. thuringiensis*. This data indicates that the targeting peptide fused to the N-terminus of Cry2Ab protein was efficiently processed or removed.

Increased expression of Cry2Ab in pMON30464 (targeted) vectors relative to pMON26800 (non-targeted) vectors was also observed in $R_1$ progeny plants derived from the original $R_0$ transgenic events, indicating that high expression is heritable (Table 5).

TABLE 4

Expression of Cry2Ab in $R_0$ Corn Transformed with Targeted (pMON30464) and Untargeted (pMON30463) Expression Vectors: Distribution of Expression Levels in Different Events

| Vector | Total Events | Total ECB+ | 0 ppm | 0–5 ppm | 5–15 ppm | 15–50 ppm | 50–100 ppm | 100–200 ppm | >200 ppm |
|---|---|---|---|---|---|---|---|---|---|
| non-targeted (30463) | 16 | 3 (19%) | 0 | 0 | 3 | 0 | 0 | 0 | 0 |
| targeted (30464) | 40 | 14 (35%) | 0 | 2 | 2 | 0 | 0 | 4 | 5 |

TABLE 5

Expression of Cry2Ab In $R_1$ Corn Transformed with Targeted (pMON30464) and Untargeted (pMON26800) Expression Vectors: Distribution of Expression Levels in Different Events

| Vector | Total # events assayed | 0 ppm | 0–5 ppm | 5–15 ppm | 15–50 ppm | 50–100 ppm | 100–200 ppm | >200 ppm |
|---|---|---|---|---|---|---|---|---|
| non-targeted (26800) | 28 | 0 | 18 | 10 | 0 | 0 | 0 | 0 |
| targeted (30464) | 33 | 5 | 3 | 2 | 0 | 2 | 4 | 17 |

To effectively control insects that feed on a variety of corn tissues, it is critical that the insecticidal protein be expressed at high levels throughout all potential feeding sites. To determine if the increases in targeted expression of Cry2Ab occur in other tissues, independent targeted and non-targeted transgenic events representing the high expressing lines obtained with the respective vector types were assayed for Cry2Ab expression levels in parallel. Expression of Cry2Ab is increased in virtually all of the corn tissues attacked by pests such as *Ostrina nubialis* and *Helicoverpa zea* by targeted expression (Table 6). Uniform high level expression of this type is especially valuable in that it is less likely to permit evolved resistance of target pests via behavioral (feeding) adaptation.

frequency with which normal events are obtained are clearly valuable as they increase the odds of identifying an event that can be commercialized. It is also useful to enlarge the pool size of prospective events for screening by increasing the percentage of $R_0$ events (primary regenerated plants) with fertility. As plant transformation is labor intensive, any method that decreases the number of $R_0$ events that must be produced in order to obtain a transgenic event with appropriate performance and growth characteristics is also valuable.

TABLE 6

Targeted and Untargeted Cry2Ab Expression in Transgenic Maize

| Vector | Event | N | Root | Leaf | sheath | stalk | shank | husk | silk | cob | kernel |
|---|---|---|---|---|---|---|---|---|---|---|---|
| N30pMON30464 | #1 | 1 | 13.1 | 117.6 | 140.8 | 514.9 | 397.5 | 121.8 | 130.5 | 165.2 | 106.9 |
| | #2 | 4 | 11.3 ± 4.5 | 105 ± 12 | 121 ± 25 | 96 ± 18 | 134 ± 38 | 52 ± 9.1 | 101 ± 11 | 113 ± 45 | 170 ± 36 |
| N30pMON26800 | #1 | 2 | 1.2 ± 0.4 | 10 ± 5.3 | 20 ± 12 | 28 ± 5.6 | 29 ± 7.5 | 7.6 ± 7.6 | 46 ± 9.9 | 9.6 ± 9.6 | 10.9 ± 4.6 |

Expression in μg Cry2Ab/gm fresh weight (root and leaf) or dry weight tissue (sheath, stalk, shank, husk, silk, cob, kernel) shown ± standard deviation (L30464 #2) or range (L26800 #1).

Further analyses indicate that the increased levels of Cry2Ab protein produced by pMON30464 result in a commensurate increase in the level of bioactivity as measured directly in feeding assays. To assess the level of insecticidal activity produced, corn leaf tissue from control (non-transgenic), targeted (pmon30464), and non-targeted (pMON30464) plants was assayed for activity against *Heliothis virescens* in tissue diet overlay studies (Table 7). Two concentrations of tissue (0.0016 and 0.0031%) were bioassayed and the same sample of tissue used in the diet overlay was also subjected to quantitative ELISA determinations of Cry2Ab levels. The 7.5-fold increase in Cry2Ab levels in targeted (pMON30464) samples relative to the non-targeted (pMON30463) samples clearly correlates with the corresponding 6-fold difference in mean larval weight observed at both concentration rates. These data thus indicate that the increased levels of Cry2Ab produced by pMON30464 result in commensurate increases in the level of bioactivity.

TABLE 7

Correlation of Increased Cry2Ab Expression Levels with Increased Bioactivity in *Heliothis virescens* Tissue Diet Overlay Bioassay

| Tissue Sample | Cry2Ab Conc. (ppm) | Tissue Conc. 1 (0.0031% Tissue) Mean Larval Wt. (mg) | Tissue Conc. 2 (0.0016% Tissue) Mean Larval Wt. (mg) |
|---|---|---|---|
| Control | 0.0 | 22.00 | 24.6 |
| Targeted | 444 | 1.2 | 2.1 |
| Untargeted | 60 | 7.3 | 12.7 |

Large populations of independent transgene $R_0$ insertion events of the non-targeted pMON26800 and pMON30463 vectors, and the targeted pMON30464 vector, were generated and scored for fertility. It was observed that a higher percentage of the $R_0$ events generated with the targeted vector were fertile (Table 8). Progeny of fertile $R_0$ events were subsequently introduced into field tests where they were scored for European corn borer resistance (ECB1) and normal segregation.

Methods for determination of ECB1 ratings and segregation values were essentially as described (Armstrong et al., 1995). Events that passed the ECB1 and segregation criteria were subsequently scored for stunting or height reductions. While 60% of the non-targeted events displayed height reductions, only 3% of the targeted events were stunted (Table 8). Improved fertility and reduced stunting resulted in significantly improved (37% vs. 8%) recovery of unstunted ECB1 positive events with the targeted Cry2Ab vector. In summary, 4-fold more non-targeted $R_0$ events must be produced and screened to obtain the same number of normal, ECB+$R_0$ events obtained with the targeted Cry2Ab vector in a transformation study.

TABLE 8

Comparisons of Percentage of Fertile, Stunted, and Normal Maize Plants Obtained with Untargeted and Targeted Cry2Ab Expression Vectors

| Vector | #ECB LD + $R_0$ Events[a] | % Fertile Events[b] | % Stunted[c] | % Normal, ECB1 +[d] |
|---|---|---|---|---|
| Untargeted | 192 | 66 | 63 | 7 |
| Targeted | 78 | 85 | 4 | 31 |

[a]#ECB LD + $R_0$ events are the # of $R_0$ events that were positive by an ECB leaf disk feeding assay.
[b]% of the ECB LD + $R_0$ events yielding viable R1 progeny (seed).
[c]% Stunted is the % of the ECB1 positive and properly segregating events with reduced stature. (Total ECB1 positive and properly segregating for non-targeted was 38; for targeted was 25).
[d]4)% normal, ECB1 + is the % normal, ECB + events obtained relative to the total number of ECB LD + $R_0$ events screened.

5.2 Example 2

Plastid Targeting of Cry2Ab Increases Frequency of Agronomically-Normal Plants Recovered from Transformation To obtain a commercially viable transgene-based insect control trait, it is crucial that an event with normal plant growth characteristics be obtained. In most instances a fairly large number of independent transgenic events are advanced into field tests to insure that an event that meets all of the key criteria (effective insect control, normal Mendelian behavior of the transgene, and normal growth characteristics or agronomics) will be identified. Methods that increase the

5.3 Example 3

Plastid Targeting of Cry2Ab Increases Frequency of High Level European Corn Borer Control in Transgenic Corn The previously described populations of independently transformed events derived from both targeted (pMON30464) and non-targeted (pMON30463 or pMON26800) Cry2Ab expression vectors were also screened for resistance to second generation European corn borer infestations (ECB2). To facilitate these studies, the commercially efficacious transgenic corn event MON810 (Yieldgard™) transformed with the Cry1Ab gene was included as a positive control. Efficacy against ECB2 was tested in field tests essentially as described (Armstrong et al., 1995). In the 1996 field test, 18 independent non-targeted pMON26800 events were compared to MON810 (Cry1Ab). Of these 18 events, only one delivered ECB2 protection that was both statistically indistinguishable from MON810 and significantly less than the non-transgenic negative control (event UT1 in Table 9). In the 1997 field test, 18 independent targeted events (pMON30464) were tested in parallel with 3 non- targeted events (1 pMON30463 event and the two pMON26800 events derived from the 1996 tests) and MON810 (Table 10). Nine of the eighteen targeted pMON30464 events delivered ECB2 protection that was statistically indistinguishable from ECB2 protection conferred by the commercially efficacious Cry1Ab-expressing MON810 (Yieldgard™) event and all had significantly less ECB2 damage than the non-transgenic negative control (Table 10).

These data sets indicate that the absolute number and frequency of commercially efficacious Cry2Ab lines obtained from the targeted pMON30464 vector is much greater than that obtained from the non-targeted pMON26800 vector. While 9 of 18 targeted Cry2Ab events (50%) delivered ECB2 control that was both statistically indistinguishable from the MON810 Cry1Ab commercial standard and significantly less than the non-transgenic negative control, only 1 of 18 non-targeted Cry2Ab events (6%) displayed ECB2 control that was both statistically indistinguishable from the MON810 cry1Ab commercial standard and significantly less than the non-transgenic negative control. The superiority of the targeted Cry2Ab expression vector is especially evident if one considers that 9 commercially efficacious Cry2Ab events were obtained from a total of 78 ECB leaf disk positive $R_0$ plants for an 11.5% frequency of recovery while only 3 commercially efficacious Cry2Ab events were obtained from a total of 192 ECB leaf disk feeding positive Ros for a 1.6% recovery frequency ($R_0$ ECB data from Table 6).

TABLE 9

Comparison of ECB2 Protection in Untargeted (UT) Cry2Ab Transgenic Corn Relative to MON810 Cry1Ab Yieldgard ™ Transgenic Corn in Field Tests

| Event | Sample Size | Stalk Tunneling (inches) |
|---|---|---|
| MON810 (+ ctrl.) | 20 | 0.3[a] |
| UT1 | 10 | 0.7[a,*] |
| UT2 | 10 | 1.9[a] |
| UT3 | 10 | 2.0[a] |
| UT4 | 10 | 2.5[b] |
| UT5 | 8 | 2.6[b] |
| UT6 | 10 | 2.9[b] |
| UT7 | 10 | 3.1[b] |
| UT8 | 10 | 3.4[b] |
| UT9 | 10 | 3.4[b] |
| UT10 | 10 | 3.5[b] |
| UT11 | 4 | 3.6[b] |
| Wild type | 10 | 3.7[b] |
| UT12 | 10 | 3.8[b] |
| UT13 | 10 | 4.6[b] |
| UT14 | 10 | 5.8[b] |

TABLE 9-continued

Comparison of ECB2 Protection in Untargeted (UT) Cry2Ab Transgenic Corn Relative to MON810 Cry1Ab Yieldgard ™ Transgenic Corn in Field Tests

| Event | Sample Size | Stalk Tunneling (inches) |
|---|---|---|
| UT15 | 10 | 6.8[c] |
| UT16 | 10 | 7.6[c] |
| UT17 | 10 | 9.3[c] |
| UT18 | 10 | 10.1[c] |

[a,b]Values marked with the same superscript (a) are statistically indistinguishable from MON810 in planned comparisons at $P = 0.05$. Values with superscripts (b) are statistically distinct. Events with stalk tunneling values significantly greater than the Cry1Ab commercial standard MON810 are shown in boldface. Genetic background of all events is identical (B73 × H99).
[c,*]Values marked with an asterisk are significantly lower than the wild-type non-transgenic negative control in planned comparisons with the negative control ($P = 0.05$). Values marked with superscript (c) are significantly greater than the wild-type non-transgenic negative control in planned comparisons with the negative control ($P = 0.05$). UT1-UT18: Untargeted pMON26800 events #1–18.

TABLE 10

Comparison of ECB2 Protection in Targeted (T) and Untargeted (UT) Cry2Ab Transgenic Corn Relative to MON810 Cry1Ab Yieldgard ™ Transgenic Corn in Field Tests

| Event | Sample Size | Stalk Tunneling (inches) |
|---|---|---|
| T1 | 9 | 0.6[a] |
| T2 | 10 | 0.6[a] |
| MON810 (+ ctrl.) | 30 | 0.9[a] |
| T3 | 14 | 1[a] |
| T4 | 12 | 1.3[a] |
| T5 | 7 | 1.4[a] |
| UT1 | 10 | 1.6[a] |
| T6 | 13 | 1.6[a] |
| T7 | 11 | 1.6[a] |
| T8 | 10 | 1.7[a] |
| UT2 | 10 | 1.8[a] |
| T9 | 10 | 2.4[a] |
| T10 | 12 | 2.5[b] |
| T11 | 7 | 2.6[b] |
| T12 | 9 | 2.9[b] |
| T13 | 10 | 3.2[b] |
| T14 | 11 | 3.3[b] |
| T15 | 10 | 3.5[b] |
| T16 | 10 | 4.0[b] |
| T17 | 10 | 4.3[b] |
| UT3 | 8 | 4.8[b] |
| T18 | 8 | 5.4[b] |
| wild type (− ctrl.) | 20 | 13.7[c] |

[a,b,c]Values marked with the superscript (a) are statistically indistinguishable from MON810 in planned comparisons at $P = 0.05$. Values with superscripts are statistically distinct. Events with stalk tunneling values significantly greater than the Cry1Ab commercial standard MON810 are shown in boldface; all transgenic events display significantly less tunneling than the wild type non-transgenic negative control in planned comparisons to the negative control ($P = 0.5$). Genetic background of all events is identical (B73 × H99).
T1–T18: Targeted pMON30464 events #1–18. UT1–UT3: Untargeted pMON30463 and pMON26800 events #1–3. UT1 in the 1997 field test is the same pMON26800 event as UT3 in the 1996 field test.

5.4 Example 4

Plastid Targeting of the Cry2Ab Protein Results in Increased Expression in Transgenic Cotton Callus Tissue Levels of the Cry2Ab protein in cotton callus tissue transformed with plastid-targeted and non-targeted Cry2Ab expression vectors were compared. Cry2Ab levels were significantly higher in callus that had been transformed with the plastid-targeted genes (Table 11).

Plant expression vector pMON33830 contained a Cry2Ab expression cassette consisting of the following genetic elements operably linked to produce functional Cry2Ab protein in plant cells: an enhanced CaMV 35S promoter, a petunia hsp70 5' untranslated leader, a synthetic cry2Ab gene with a translation initiation codon (SEQ ID NO:1), and transcription termination and polyadenylation sequences from the nopaline synthase (NOS) gene of *A. tumefaciens.*

Plant expression vectors pMON33827 (SEQ ID NO:13), pMON33828 (SEQ ID NO:14) and pMON33829 (SEQ ID NO:15) contained Cry2Ab expression cassettes similar to that occurring in pMON33830 except that in each a different chloroplast targeting sequence was translationally fused to the N-terminus of the synthetic cry2Ab gene. pMON33827 contained the coding sequence for PTP1 (SEQ ID NO:5) which consists of an *Arabidopsis thaliana* ssRUBISCO (SSU) chloroplast targeting sequence and sequences coding for the first 24 amino acids of ssRUBISCO (SSU) protein (Wong et al., 1992). SEQID NO:6 represents the PIP1 targeting peptide sequence. This peptide contains the complete native targeting sequence including the plastid targeting peptide cleavage site along with the first twenty-four amino acids of the mature RUBISCO SSU protein sequentially linked to a duplicated sequence of amino acids (SEQID NO:6 amino acids position No. 50–57) containing the RUBISCO SSU plastid targeting peptide cleavage site (SEQID NO:6 amino acids position No. 80–87). PTP1 therefor contains a duplicated plastid targeting peptide cleavage site. The polynucleotide cassette containing this PTP coding sequence is linked at its 3' end to an NcoI restriction site which allows for insertions of coding sequences which are translationally in-frame with the PTP coding sequence, for example, those which encode Cry2Ab, Cry2Aa, variants of these, and other useful polypeptide encoding sequences.

pMON33828 contained the coding sequence for PTP1Δ (SEQ ID NO:7), a modification of PTP1 in which the 24 amino acids of SSU between the two transit peptide cleavage sites was removed by cleavage with the restriction enzyme SphI, which cuts once within each copy of the transit peptide cleavage site, and re-ligation, resulting in the presence of only the transit peptide portion of PTP1 followed by a single copy of the transit peptide cleavage site and an NcoI site. The peptide sequence for PTP1A is designated SEQ ID NO:8.

pMON33829 contained the coding sequence for PTP2 (SEQ ID NO:9), the transit peptide sequence from the EPSP synthase gene of *Arabidopsis thaliana*. The peptide sequence for PTP2 is designated SEQ ID NO:10.

All of the above plant transformation expression vectors also contained a selectable marker gene cassette which confers kanamycin resistance to transformed plant cells.

Cotton callus tissue from 12 randomly chosen, independent transgenic events from transformations with each of pMON33827, pMON33828, pMON33829 and pMON33830 was subjected to quantitative analysis of Cry2Ab protein levels using a quantitative ELISA assay. This ELISA used a direct sandwich technique that used a monoclonal capture antibody raised against Cry2Aa, a different Cry2Aa monoclonal antibody conjugated to alkaline phosphatase as the secondary antibody, and purified Cry2Aa protein as a standard. Comparison of Cry2Ab expression levels in targeted and non-targeted callus tissue showed a significant increase in expression when a chloroplast targeting sequence was included (Table 11). PTP1Δ provided a significantly greater mean expression level when compared to non-targeted Cry2Ab as determined by applying a t test ($t=2.31$, $p=0.03$). PTP2 provided a significantly greater probability of obtaining callus lines expressing higher levels of Cry2Ab as determined by applying a G test ($G^2/X^2=5.6$, $p=0.02$).

TABLE 11

Cry2Ab Levels in Independent Transformed Cotton Callus Lines Comparing Chloroplast-Targeted and Untargeted cry2Ab genes

| Cotton Callus Lines | Cry2Ab ng/mL of Callus Extract |
|---|---|
| Non-transformed callus | |
| Line 1 | 0 |
| Line 2 | 0 |
| Line 3 | 0 |
| Line 4 | 0 |
| pMON33827, PTP1-cry2Ab gene | |
| Line 1 | 464 |
| Line 2 | 61 |
| Line 3 | 0 |
| Line 4 | 25 |
| Line 5 | 0 |
| Line 6 | 368 |
| Line 7 | 74 |
| Line 8 | 101 |
| Line 9 | 20 |
| Line 10 | 652 |
| Line 11 | 0 |
| Line 12 | 0 |
| pMON33828, PTP1Δ-cry2Ab Gene | |
| Line 1 | 252 |
| Line 2 | 235 |
| Line 3 | 0 |
| Line 4 | 416 |
| Line 5 | 0 |
| Line 6 | 0 |
| Line 7 | 0 |
| Line 8 | 101 |
| Line 9 | 393 |
| Line 10 | 587 |
| Line 11 | 788 |
| Line 12 | 277 |
| pMON33829, PTP2-cry2Ab Gene | |
| Line 1 | 60 |
| Line 2 | 0 |
| Line 3 | 2220 |
| Line 4 | 2036 |
| Line 5 | 0 |
| Line 6 | 38 |
| Line 7 | 674 |
| Line 8 | 2440 |
| Line 9 | 15 |
| Line 10 | 91 |
| Line 11 | 290 |
| Line 12 | 71 |
| pMON33830, cry2Ab Gene | |
| Line 1 | 19 |
| Line 2 | 166 |
| Line 3 | 47 |
| Line 4 | 20 |
| Line 5 | 33 |
| Line 6 | 47 |
| Line 7 | 781 |
| Line 8 | 35 |
| Line 9 | 31 |
| Line 10 | 0 |
| Line 11 | 0 |
| Line 12 | 136 |

5.5 Example 5

Targeting the Cry2Aa Protein to Plastids Results in Decreased Expression in Transgenic Cotton Callus Tissue In contrast to Example 4 above, and exemplifying that the increase in expression obtained using plastid targeting sequences is specific to particular cry genes, the inventors discovered that the same plastid targeting sequences described above, PTP1, PTP1Δ and PTP2, resulted in significantly lower levels of expression of the closely related cry2Aa gene in transgenic cotton callus (Table 12). Plant expression vector pMON33803 contained a cry2Aa expression cassette consisting of the following genetic elements operably linked to produce functional Cry2Aa protein in plant cells: a FMV35S promoter, a petunia heat shock HSP70 5' untranslated leader, a synthetic cry2Aa gene (SEQ ID NO:11) with a translation initiation codon and NcoI restriction enzyme site at the 5'-end, and transcription termination and polyadenylation sequences from the E9 SSU gene from pea. The peptide sequence for the Cry2Aa protein is designated SEQ ID NO:12. pMON33812, pMON33811, and pMON33806 contained cry2Aa expression cassettes similar to that occurring in pMON33803 except that in each case a different chloroplast targeting sequence (PTP1, PTP1Δ, and PTP2, respectively) was transitionally fused to the N-terminus of the synthetic cry2Aa gene. All of these vectors also contained a selectable marker gene cassette conferring glyphosate resistance to transformed plant cells.

Cotton callus tissue from 10 randomly chosen independent transgenic events from transformations with each of pMON33803, pMON33812, pMON33811 and pMON33806 was subjected to quantitative analysis of Cry2Aa protein levels using the quantitative Cry2 ELISA assay. Comparison of Cry2Aa expression levels in targeted and non-targeted callus tissue showed a significant decrease in expression when chloroplast targeting sequences were included (Table 12). The non-targeted cry2Aa gene conferred expression levels that differed significantly from those achieved using any of the three plastid targeted cry2Aa genes, as determined by using a Tukey-Kramer HSD test ($\alpha$=0.05).

TABLE 12

Cry2Aa Levels In Independent Transformed Cotton Callus Lines Comparing Chloroplast-Targeted And Untargeted Cry2Aa Genes

| Cotton Callus Lines | Cry2Aa ng/mL of Extract |
|---|---|
| Non-transformed callus | |
| Line 1 | 0 |
| Line 2 | 0 |
| Line 3 | 0 |
| Line 4 | 0 |
| pMON33812, PTP1-Cry2Aa Gene | |
| Line 1 | 29 |
| Line 2 | 32 |
| Line 3 | 22 |
| Line 4 | 41 |
| Line 5 | 24 |
| Line 6 | 47 |
| Line 7 | 43 |
| Line 8 | 49 |
| Line 9 | 0 |
| Line 10 | 23 |
| pMON33811.PTP1Δ-Cry2Aa Gene | |
| Line 1 | 0 |
| Line 2 | 59 |
| Line 3 | 48 |
| Line 4 | 72 |
| Line 5 | 29 |
| Line 6 | 37 |
| Line 7 | 44 |
| Line 8 | 32 |
| Line 9 | 20 |
| Line 10 | 0 |
| pMON33806, PTP2-Cry2Aa Gene | |
| Line 1 | 27 |
| Line 2 | 0 |
| Line 3 | 10 |
| Line 4 | 84 |
| Line 5 | 205 |
| Line 6 | 0 |
| Line 7 | 13 |
| Line 8 | 6 |
| Line 9 | 0 |
| Line 10 | 8 |
| pMON33803, Cry2Aa Gene | |
| Line 1 | 63 |
| Line 2 | 2278 |
| Line 3 | 181 |
| Line 4 | 3131 |
| Line 5 | 3752 |
| Line 6 | 851 |
| Line 7 | 303 |
| Line 8 | 1365 |
| Line 9 | 1601 |
| Line 10 | 1648 |

5.6Example 6

Targeting the Cry2Aa Protein to Plastids Results in Decreased Expression and Increased Phytotoxicity in Transgenic Tobacco Plants Transformed tobacco plants were generated using pMON33803, the non-targeted cry2Aa plant expression vector and pMON33806, the chloroplast-targeted PTP2-cry2Aa plant expression vector. Leaf tissue samples of equivalent weight from 48 pMON33803 plants and 41 pMON33806 plants were extracted in equal volumes of extraction buffer and the relative levels of cry2Aa were determined using a qualitative ELISA (Table 13). This ELISA used a direct sandwich technique that used polyclonal capture antibody raised against Cry2Aa, the same polyclonal antibody conjugated to alkaline phosphatase as the secondary antibody, and purified Cry2Aa protein as a standard.

The proportion of the total number of plants recovered from transformation that expressed non-targeted Cry2Aa at high levels was greater than the proportion of plants recovered that expressed targeted Cry2Aa at high levels. Conversely, the proportion of the total number of plants recovered from transformation that failed to express detectable targeted Cry2Aa was greater than the proportion of plants recovered that failed to express non-targeted Cry2Aa. All of the PTP2-Cry2Aa plants that had detectable levels of Cry2Aa expression exhibited a severely abnormal phenotype; these plants were extremely stunted, had shortened internodes, had deformed, wrinkled leaves, and were infertile. All of the PTP2-Cry2Aa plants that lacked Cry2Aa expression appeared normal. In contrast, only some of the high expressing non-targeted Cry2Aa plants displayed a stunted phenotype.

TABLE 13

Cry2Aa Levels in Independent Transformed Tobacco Plants Comparing Chloroplast-Targeted and Untargeted cry2Aa Genes

| Transgenic Plants pMON33803_cry2Aa gene | ELISA O.D. | Transgenic Plants pMON33806 PTP2-cry2Aa gene | ELISA O.D. |
|---|---|---|---|
| Plant 1 | 2.5 | Plant 1 | 0 |
| Plant 2 | 1.1 | Plant 2 | 0 |
| Plant 3 | 2.7 | Plant 3 | 0 |
| Plant 4 | 0.1 | Plant 4 | 0 |
| Plant 5 | 0.1 | Plant 5 | 0 |
| Plant 6 | 2.3 | Plant 6 | 0.9 |
| Plant 7 | 1.9 | Plant 7 | 0.4 |
| Plant 8 | 2.4 | Plant 8 | 0.4 |
| Plant 9 | 0 | Plant 9 | 0 |
| Plant 10 | 2.1 | Plant 10 | 0.6 |
| Plant 11 | 0.1 | Plant 11 | 0 |
| Plant 12 | 0.5 | Plant 12 | 0.5 |
| Plant 13 | 2.4 | Plant 13 | 0.4 |
| Plant 14 | 0.1 | Plant 14 | 0.7 |
| Plant 15 | 2.2 | Plant 15 | 1.5 |
| Plant 16 | 0.2 | Plant 16 | 0.6 |
| Plant 17 | 2.6 | Plant 17 | 0 |
| Plant 18 | 2.5 | Plant 18 | 0 |
| Plant 19 | 2.5 | Plant 19 | 0 |
| Plant 20 | 1.4 | Plant 20 | 0 |
| Plant 21 | 2.4 | Plant 21 | 0 |
| Plant 22 | 2.1 | Plant 22 | 0 |
| Plant 23 | 0.5 | Plant 23 | 0.6 |
| Plant 24 | 2.1 | Plant 24 | 0 |
| Plant 25 | 0.3 | Plant 25 | 0 |
| Plant 26 | 0 | Plant 26 | 0.6 |
| Plant 27 | 0.3 | Plant 27 | 0 |
| Plant 28 | 2.2 | Plant 28 | 0.7 |
| Plant 29 | 0 | Plant 29 | 0.5 |
| Plant 30 | 1.5 | Plant 30 | 0 |
| Plant 31 | 0.1 | Plant 31 | 0 |
| Plant 32 | 0.1 | Plant 32 | 0 |
| Plant 33 | 0.7 | Plant 33 | 0 |
| Plant 34 | 0 | Plant 34 | 0 |
| Plant 35 | 0 | Plant 35 | 0 |
| Plant 36 | 0 | Plant 36 | 0 |
| Plant 37 | 0.2 | Plant 37 | 0 |
| Plant 38 | 2.1 | Plant 38 | 0 |
| Plant 39 | 0 | Plant 39 | 0 |
| Plant 40 | 1.9 | Plant 40 | 0 |
| Plant 41 | 1.5 | Plant 41 | 0 |
| Plant 42 | 2.8 | | |
| Plant 43 | 0.6 | | |
| Plant 44 | 2.1 | | |
| Plant 45 | 0.9 | | |
| Plant 46 | 0 | | |
| Plant 47 | 0 | | |
| Plant 48 | 0 | | |

5.7 Example 7

Transformation of Tobacco Chloroplast with a Cry2Ab Gene

Recombinant plants can be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67–70, 1987). Methods and compositions for obtaining cells containing chloroplasts into which heterologous DNA has been inserted have been described, for example by Daniell et al. (U.S. Pat. No. 5,693,507; 1997) and Maliga et al. (U.S. Pat. No. 5,451,513; 1995). A vector can be constructed which contains an expression cassette from which a Cry2A protein could be produced. A cassette could contain a chloroplast operable promoter sequence driving expression of a cry2A crystal protein gene, constructed in much the same manner as other polynucleotides herein, using thermal amplification methodologies, restriction endonuclease digestion, and ligation etc. A chloroplast expressible gene would provide a promoter and a 5' untranslated region from a heterologous gene or chloroplast gene such as psbA, which would provide for transcription and translation of a DNA sequence encoding a Cry2A protein in the chloroplast; a DNA sequence encoding Cry2A protein; and a transcriptional and translational termination region such as a 3' inverted repeat region of a chloroplast gene that could stabilize an expressed cry2A mRNA. Expression from within the chloroplast would enhance cry2A gene product accumulation. A host cell containing chloroplasts or plastids can be transformed with the expression cassette and then the resulting cell containing the transformed chloroplasts can be grown to express the Cry2A protein. A cassette may also include an antibiotic, herbicide tolerance, or other selectable marker gene in addition to the cry2A gene. The expression cassette may be flanked by DNA sequences obtained from a chloroplast DNA which would facilitate stable integration of the expression cassette into the chloroplast genome, particularly by homologous recombination. Alternatively, the expression cassette may not integrate, but by including an origin of replication obtained from a chloroplast DNA, would be capable of providing for replication of the heterologous cry2A gene in the chloroplast. Plants can be generated from cells containing transformed chloroplasts and can then be grown to produce seeds, from which additional plants can be generated. Such transformation methods are advantageous over nuclear genome transformation, in particular where chloroplast transformation is effected by integration into the chloroplast genome, because chloroplast genes in general are maternally inherited. This provides environmentally "safer" transgenic plants, virtually eliminating the possibility of escapes into the environment. Furthermore, chloroplasts can be transformed multiple times to produce functional chloroplast genomes which express multiple desired recombinant proteins, whereas nuclear genomic transformation has been shown to be rather limited when multiple genes are desired. Segregational events are thus avoided using chloroplast or plastid transformation. Unlike plant nuclear genome expression, expression in chloroplasts or plastids can be initiated from only one promoter and continue through a polycistronic region to produce multiple peptides from a single mRNA.

The expression cassette would be produced in much the same way that other plant transformation vectors are constructed. Plant chloroplast operable DNA sequences can be inserted into a bacterial plasmid and linked to DNA sequences expressing desired gene products, such as Cry2A proteins, so that Cry2A protein is produced within the chloroplast, obviating the requirement for nuclear gene regulation, capping, splicing, or polyadenylation of nuclear regulated genes, or chloroplast or plastid targeting sequences. An expression cassette comprising a cry2A gene, which is either synthetically constructed or a native gene derived directly from a *B. thuringiensis* genome or a *B. thuringiensis* episomal element, would be inserted into a restriction site in a vector constructed for the purpose of chloroplast or plastid transformation. The cassette would be flanked upstream by a chloroplast or plastid functional promoter and downstream by a chloroplast or plastid functional transcription and translation termination sequence.

The resulting cassette could be incorporated into the chloroplast or plastid genome using well known homologous recombination methods.

Alternatively, chloroplast or plastid transformation could be obtained by using an autonomously replicating plasmid or other vector capable of propagation within the chloroplast or plastid. One means of effectuating this method would be to utilize a portion of the chloroplast or plastid genome required for chloroplast or plastid replication initiation as a means for maintaining the plasmid or vector in the transformed chloroplast or plastid. A sequence enabling stable replication of a chloroplast or plastid epigenetic element could easily be identified from random cloning of a chloroplast or plastid genome into a standard bacterial vector which also contains a chloroplast or plastid selectable marker gene, followed by transformation of chloroplasts or plastids and selection for transformed cells on an appropriate selection medium. Introduction of an expression cassette as described herein into a chloroplast or plastid replicable epigenetic element would provide an effective means for localizing a Cry2A *B. thuringiensis* δ-endotoxin to the chloroplast or plastid.

6.0 References

The following references, to the extent that they provide exemplary procedural or other details supplementary to those set forth herein, are specifically incorporated herein by reference.

U.S. Pat. No. 4,535,060; 1985
U.S. Pat. No. 4,554,101; 1985
U.S. Pat. No. 4,683,195; 1987
U.S. Pat. No. 4,683,202; 1987
U.S. Pat. No. 4,757,011; 1988
U.S. Pat. No. 4,769,061; 1988
U.S. Pat. No. 4,940,835; 1990
U.S. Pat. No. 4,971,908; 1990
U.S. Pat. No. 5,004,863; 1991
U.S. Pat. No. 5,015,580; 1991
U.S. Pat. No. 5,023,179; 1991
U.S. Pat. No. 5,225,341; 1993
U.S. Pat. No. 5,264,364; 1993
U.S. Pat. No. 5,276,269; 1994
U.S. Pat. No. 5,322,687; 1994
U.S. Pat. No. 5,338,544; 1994
U.S. Pat. No. 5,349,124; 1994
U.S. Pat. No. 5,378,619; 1995
U.S. Pat. No. 5,384,253; 1995
U.S. Pat. No. 5,416,011; 1995
U.S. Pat. No. 5,424,412; 1995
U.S. Pat. No. 5,451,513; 1995
U.S. Pat. No. 5,463,175, 1995
U.S. Pat. No. 5,482,852; 1996
U.S. Pat. No. 5,491,288; 1996
U.S. Pat. No. 5,500,365; 1996
U.S. Pat. No. 5,508,468; 1996
U.S. Pat. No. 5,569,834; 1996
U.S. Pat. No. 5,689,052, 1997
U.S. Pat. No. 5,693,507; 1997
EPO 0120516
WO 92/17591
WO 95/24492
Armstrong et al., *Plant Cell Rep.,* 9:335–339, 1990.
Armstrong et al., *Crop Science,* 35(2):550–557, 1995.
Barton et al., *Plant Physiol.,* 85:1103–1109, 1987.
Benfey et al., *EMBO J.,* 8:2195–2202, 1989.
Bevan et al., *Nature,* 304:184, 1983.
Callis et al., *Genes Dev.,* 1: 1183–1200; 1987.
Cheng et al., *Proc. Natl. Acad. Sci. USA,* 96(6):2767–2772, 1998.
Dhir et al., *Plant Cell Rep.,* 10: 106–10; 1991
Diehn et al., In: *Genetic Engineering,* Ed. J. K. Setlow, Plenum Press, New York, N.Y., 18:83–99, 1996.
Donovan et al., *Mol. Gen. Genet.,* 214:365–372, 1988.
Donovan et al., *Appl. Environ. Microbiol.,* 58:3921–3927, 1992.
English et al., Insect. *Biochem. Molec. Bio.,* 24(10):1025–1026, (1994)
Feinberg and Vogelstein, *Anal Biochem.,* 132:6–13, 1983.
Fischhoff et al., *Bio/Technology,* 5:807–813, 1987.
Frischauf et al., *Methods Enzymol.,* 153:103–115, 1987.
Fromm et al., *Nature,* 319:791–793, 1986.
Fromm et al., *Bio/Technology,* 8:833–839, 1990.
Gould et al., *J. Cell Biol.,* 105:2923–2931, 1987.
Hanley-Bowden et al., *Trends in Biochemical Sciences* 12:67–70; 1987.
Herrera-Estrella et al., *Nature,* 303:209, 1983.
Hertig et al., *Plant Mol. Biol.,* 16:171–174, 1991.
Hofte and Whiteley, *Microbiol. Rev.,* 53(2):242–255, 1989.
Horsch et al., *Science,* 227:1229–1231, 1985.
Horton et al., *Gene,* 77:61–68, 1989.
Ishida et al., *Nat. Biotechnol.,* 14(6):745–750, 1996.
Kay et al., *Science,* 236:1299–1302, 1987.
Keegstra and Olsen, *Ann. Rev. Plant Physiol. Mol. Biol.,* 40:471–501, 1989.
Klee et al., *Bio/Technology,* 3:637–642, 1985.
Klee et al., *Mol. Gen. Genet.,* 210:437–442, 1987.
Koehler and Ho, *Plant Cell,* 2:769–783, 1990.
Koziel et al., *Bio/Technology,* 11:194–200, 1993.
Lambert et al., *Appl. Environ. Microbiol.,* 62:80–86, 1996.
Lee et al., *Science,* 239:1288–1291, 1988.
Lindstrom et al., *Dev. Genet.,* 11:160–7; 1990.
Macejak and Sarnow, *Nature,* 353:90–94, 1991.
MacIntosh et al., *J. Invert. Pathol.,* 56:258–266, 1990.
Maliga, *Trends in Biotechnology,* 11:101–106, 1993.
McElroy et al., *Plant Cell,* 2:163–171, 1990.
McGaughey and Whalon, *Science,* 258:1451–1455, 1993.
Nayak et al., *Proc. Natl. Acad. Sci. USA,* 94(6):2111–2116, 1997.
Odell et al., *Nature,* 313: 810–12; 1985.
Pelletier and Sonenberg, *Nature,* 334:320–325, 1988.
Perlak et al., *Bio/technology,* 8:939–943, 1990.
Perlak et al., *Plant Molecular Biol.,* 22:313–321, 1993.
Roush, *Biocontrol Sci. Technol.,* 4:501–516, 1994.
Russell et al., *Plant Cell Reports,* 13:24–27, 1993.
Shelton et al., *J. Econ. Entomol.,* 86:697–705, 1993.
Tang et al., *Appl. Environ. Microbiol.,* 62:564–569, 1996.
Tillmann et al., *EMBO J.,* 8(9):2463–2467, 1989.
Vaeck et al., *Nature,* 328:33–37, 1987.
Vasil et al., Plant Physiol., 91:1575–1579; 1989.
Vodkin et al., Cell, 34:1023–1031; 1983.
Widner et al., J. Bacteriol., 171:965–974; 1989.
Widner et al., (a), J. Bacteriol., 172:2826–2832; 1990.
Winter et al., *Mol. Gen. Genet.,* 221(2):315–319, 1988.
Wong et al., *Plant Molec. Biol.,* 20:81–93, 1992.
Xu et al., *Plant Mol. Biol.,* 27:237–248, 1995.
Yamamoto et al., *Plant Cell,* 3:371–382, 1991.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A plant comprising a nucleotide sequence encoding a Cry2Ab *Bacillus thuringiensis* δ-endotoxin protein comprising a plant functional promoter sequence operably linked to a first polynucleotide sequence encoding a plastid transit peptide, which linked in-frame to a second polynucleotide sequence encoding said Cry2Ab *Bacillus thuringiensis* δ-endotoxin protein, said second polynucleotide sequence being operably linked to a plant functional 3' end transcription termination and polyadenylation sequence, wherein expression of said nucleotide sequence in said plant yields a fusion protein comprised of an amino-terminal plastid transit peptide covalently linked to said δ-endotoxin protein, and said plastid transit peptide functions to localize said δ-endotoxin protein to a plastid.

2. The plant of claim 1 wherein said nucleotide sequence further comprises one or more plant functional intron sequences, wherein said one or more plant functional intron sequences are included within said nucleotide sequence from positions selected from the group consisting of a) between said promoter sequence and said first polynucleotide sequence; and b) within said first polynucleotide sequence.

3. The plant of claim 2, wherein said intron sequence is a maize heat shock protein 70 intron sequence.

4. The plant of claim 1, wherein said first polynucleotide sequence encodes a plastid transit peptide selected from the group consisting of zmSSU PTP, PTP1, PTP1Δ, and PTP2.

5. The plant of claim 4, wherein said nucleotide sequence comprises nucleotides 17 to 3182 of SEQ ID NO:13.

6. The plant of claim 4, wherein said nucleotide sequence comprises nucleotides 17 to 3092 of SEQ ID NO:14.

7. The plant of claim 4, wherein said nucleotide sequence comprises nucleotides 17 to 3155 of SEQ ID NO:15.

8. The plant of claim 4, wherein the plant is a monocotyledonous plant selected from the group consisting of maize, rice, wheat, barley, oats, rye, millet, sorghum, sugarcane, and turfgrass.

9. The plant of claim 8, wherein said monocotyledonous plant is a maize plant.

10. The plant of claim 1, wherein the plant is a dicotyledonous plant selected from the group consisting of cotton, soybean, tomato, potato, citrus, tobacco, canola, and strawberry.

11. The plant of claim 10, wherein said dicotyledonous plant is a cotton plant or a soybean plant.

12. A plant produced from the transgenic plant of claim 1, wherein said plant has inherited said nucleotide sequence from said transgenic plant.

13. The plant of claim 1, wherein said plant further comprises a DNA sequence comprising a plant functional promoter operably linked to a polynucleotide sequence encoding a Cry1 *Bacillus thuringiensis* δ-endotoxin protein.

14. A plant tissue from progeny of the plant according to claim 13, wherein said plant tissue comprises said nucleotide sequence encoding said Cry2Ab *Bacillus thuringiensis* δ-endotoxin protein.

15. A method of producing a first transgenic plant which exhibits increased levels of accumulation of a Cry2Ab *Bacillus thuringiensis* δ-endotoxin protein and decreased phytotoxic effects of expression of a nucleotide sequence encoding said Cry2Ab *Bacillus thuringiensis* δ-endotoxin protein when compared to a second transgenic plant, said method comprising the steps of:

a) transforming a plant cell with a nucleotide sequence comprising in operable linkage a plant functional promoter sequence linked to a first polynucleotide sequence encoding a plastid transit peptide and a second polynucleotide sequence encoding said Cry2Ab *Bacillus thuringiensis* δ-endotoxin protein;

b) regenerating said first transgenic plant from said transformed plant cell; and c) comparing the level of Cry2Ab *Bacillus thuringiensis* δ-endotoxin protein accumulation and plant morphology of said first transgenic plant to said second transgenic plant transformed to express a nucleic acid sequence encoding a Cry2Ab *Bacillus thuringiensis* δ-endotoxin protein that is not linked to a plastid transit peptide, wherein expression of said nucleotide sequence in said first transgenic plant yields a fusion protein comprising an amino-terminal plastid transit peptide covalently linked to said δ-endotoxin protein, and said plastid transit peptide functions to localize said δ-endotoxin protein to a plastid.

16. The method of claim 15, wherein said decreased phytotoxic effects is selected from the group of effects consisting of an absence of chlorosis, stunting, shortened internodes, deformed leaves, and infertility when compared to transgenic plants transformed to express a nucleotide sequence encoding a Cry2Ab *Bacillus thuringiensis* δ-endotoxin protein which is not localized to the plastid.

17. The method of claim 16, wherein increased levels of accumulation of said Cry2Ab *Bacillus thuringiensis* δ-endotoxin protein. comprises from about 1 μg to about 500

μg Cry2Ab *Bacillus thuringiensis* δ-endotoxin protein per gram of one or more tissues of said first transgenic plant as set forth in Table 6.

18. The method according to claim 17 wherein said increased levels of accumulation of said δ-endotoxin protein comprises from about 15 μg to about 300 μg Cry2Ab *Bacillus thuringiensis* δ-endotoxin protein per gram of one or more tissues of said first transgenic plant as set forth in Table 6.

19. The method according to claim 18 wherein said increased levels of accumulation of said δ-endotoxin protein comprises from about 25 μg to about 200 μg Cry2Ab *Bacillus thuringiensis* δ-endotoxin protein per gram of one or more tissues of said first transgenic plant as set forth in Table 6.

20. The method according to claim 19 wherein said increased levels of accumulation of said δ-endotoxin protein comprises from about 100 μg to about 200 μg Cry2Ab *Bacillus thuringiensis* δ-endotoxin protein per gram of one or more tissues of said first transgenic plant as set forth in Table 6.

21. The method according to claim 20 wherein said increased levels of accumulation of said δ-endotoxin protein is about 200 μg Cry2Ab *Bacillus thuringiensis* δ-endotoxin protein per gram of one or more tissues of said first transgenic plant as set forth in Table 6.

22. The method according to claim 17, wherein said nucleotide sequence further comprises one or more plant functional intron sequences, wherein said one or more plant functional intron sequences are included within said nucleotide sequence from positions selected from the group consisting of a) between said promoter sequence and said first polynucleotide sequence; and b) within said first polynucleotide sequence.

23. The method of claim 22, wherein said intron sequence is a maize heat shock protein 70 intron sequence.

24. The method of claim 23, wherein said first polynucleotide sequence encodes a plastid transit peptide selected from the group consisting of zmSSU PTP, PTP1, PTP1Δ, and PTP2.

25. The method of claim 22, wherein said nucleotide sequence encoding said Cry2Ab *Bacillus thuringiensis* δ-endotoxin protein comprises nucleotides 17 to 3182 of SEQ ID NO:13.

26. The method of claim 22, wherein said nucleotide sequence encoding said Cry2Ab *Bacillus thuringiensis* δ-endotoxin protein comprises nucleotides 17 to 3092 of SEQ ID NO:14.

27. The method of claim 22, wherein said nucleotide sequence encoding said Cry2Ab *Bacillus thuringiensis* δ-endotoxin protein comprises nucleotides 17 to 3155 of SEQ ID NO:15.

28. The method of claim 24, wherein the plant cell is a monocotyledonous plant cell selected from the group consisting of maize, rice, wheat, barley, oats, rye, millet, sorghum, sugarcane, and turfgrass.

29. The method of claim 28, wherein said monocotyledonous plant cell is a maize plant cell.

30. The method of claim 17, wherein the plant cell is a dicotyledonous plant cell selected from the group consisting of cotton, soybean, tomato, potato, citrus, tobacco, canola, and strawberry.

31. The method of claim 30, wherein said dicotyledonous plant cell is a cotton plant cell or a soybean plant cell.

32. A plant produced by the method of claim 15, wherein said plant has inherited said nucleotide sequence encoding said Cry2Ab *Bacillus thuringiensis* δ-endotoxin protein from said first transgenic plant.

33. A progeny plant produced from the plant of claim 13, wherein said progeny plant comprises said polynucleotide sequence encoding said Cry2Ab *Bacillus thuringiensis* δ-endotoxin protein and said DNA sequence encoding said Cry1 *Bacillus thuringiensis* δ-endotoxin protein.

34. A tissue from the plant according to claim 32, wherein said tissue comprises said polynucleotide sequence encoding said Cry2Ab *Bacillus thuringiensis* δ-endotoxin protein.

35. A tissue from the progeny plant according to claim 33, wherein said tissue comprises said polynucleotide sequence encoding said Cry2Ab *Bacillus thuringiensis* δ-endotoxin protein and said DNA sequence encoding said Cry1 *Bacillus thuringiensis* δ-endotoxin protein.

36. A method for increasing the frequency of morphologically normal transgenic plants obtained after transformation which express a Cry2Ab *Bacillus thuringiensis* δ-endotoxin protein localized to a plastid comprising the steps of:

a) transforming plant cells with a nucleotide sequence comprising in operable linkage a plant functional promoter linked to a first polynucleotide sequence encoding a plastid transit peptide, and a second polynucleotide sequence encoding said Cry2Ab *Bacillus thuringiensis* δ-endotoxin protein;

b) selecting plant cells expressing said protein;

c) regenerating transgenic plants from said selected plant cells; and d) comparing the number of morphologically normal transgenic plants expressing said protein to the number of plants obtained after transformation which express a nucleic acid encoding a protein selected from the group consisting of a Cry2A protein which is not localized to a plastid and a Cry2A protein other than a Cry2Ab protein localized to a plastid;

wherein expression of said nucleotide sequence in said transgenic plants yields a fusion protein comprised of an amino-terminal plastid transit peptide covalently linked to said δ-endotoxin protein, and said plastid transit peptide functions to localize said δ-endotoxin protein to a plastid.

37. The method according to claim 36, wherein the increase in frequency of morphologically normal transgenic plants obtained which express a Cry2Ab *Bacillus thuringiensis* δ-endotoxin protein comprises an increase of about 4-fold more plants than the number of morphologically normal plants obtained from plants transformed to express a nucleic acid sequence encoding a Cry2Ab protein which is not localized to a plastid.

38. The method of claim 37, wherein said morphologically normal transgenic plants obtained exhibit decreased phytotoxic effects selected from the group consisting of an absence of chlorosis, stunting, shortened internodes, deformed leaves, and infertility when compared to transgenic plants transformed to express a Cry2Ab protein which is not localized to the plastid.

39. The method of claim 38, wherein said morphologically normal transgenic plants obtained exhibit increased levels of accumulation of said Cry2Ab *Bacillus thuringiensis* δ-endotoxin protein compared to plants transformed to express a Cry2Ab protein which is not localized to the plastid, wherein said increased levels comprise from about 1 μg to about 500 μg Cry2Ab *Bacillus thuringiensis* δ-endotoxin protein per gram of one or more tissues of said morphologically normal transgenic plant as set forth in Table 6.

40. The method according to claim 39, wherein said nucleotide sequence further comprises one or more plant functional intron sequences, wherein said one or more plant functional intron sequences are included within said nucleotide sequence from positions selected from the group consisting of a) between said promoter sequence and said DNA; and b) within said DNA.

41. The method of claim 40, wherein said one or more plant functional intron sequences is a maize heat shock protein 70 intron sequence.

42. The method of claim 41, wherein said DNA sequence encodes a plastid transit peptide selected from the group consisting of zmSSU PTP, PTP1, PTP1Δ, and PTP2.

43. The method of claim 40, wherein said nucleotide sequence comprises nucleotides 17 to 3182 of SEQ ID NO:13.

44. The method of claim 40, wherein said nucleotide sequence comprises nucleotides 17 to 3092 of SEQ ID NO:14.

45. The method of claim 40, wherein said nucleotide sequence comprises nucleotides 17 to 3155 of SEQ ID NO:15.

46. The method of claim 42, wherein the morphologically normal transgenic plant is a monocotyledonous plant selected from the group consisting of maize, rice, wheat, barley, oats, rye, millet, sorghum, sugarcane, and turfgrass.

47. The method of claim 46, wherein said monocotyledonous plant is a maize plant.

48. The method of claim 37, wherein the morphologically normal transgenic plant is a dicotyledonous plant selected from the group consisting of cotton, soybean, tomato, potato, citrus, tobacco, canola, and strawberry.

49. The method of claim 48, wherein said dicotyledonous plant is a cotton plant or a soybean plant.

50. The method of claim 37 further comprising transforming said plant cells with a nucleic acid sequence comprising a plant functional promoter operably linked to a polynucleotide sequence encoding a Cry1 *Bacillus thuringiensis* δ-endotoxin protein.

51. A method of identifying a morphologically normal transgenic plant which is resistant to insect infestation comprising:

a) obtaining a first plant containing a nucleic acid sequence comprising a plant functional promoter operably linked to a first polynucleotide sequence encoding a plastid transit peptide, which is linked in frame to a second polynucleotide sequence encoding a Cry2Ab *Bacillus thuringiensis* δ-endotoxin protein, said second polynucleotide sequence being operably linked to a plant functional 3' end transcription termination and polyadenylation sequence, wherein expression of said nucleic acid sequence in said plant yields a fusion protein comprising an amino-terminal plastid transit peptide covalently linked to said δ-endotoxin protein, wherein said plastid transit peptide functions to localize said δ-endotoxin protein to a plastid, and wherein said expression results in increased levels of said δ-endotoxin protein relative to plants transformed to express a nucleic acid sequence encoding a Cry2AB protein which is not localized to the plastid;

b) obtaining a second plant; and c) crossing said first plant and said second plant to obtain a crossed transgenic progeny plant, said progeny plant having inherited said nucleic acid sequence from said first plant.

52. A nucleic acid sequence comprising in operable linkage a plant functional promoter linked to a first polynucleotide sequence encoding a plastid transit peptide and a second polynucleotide sequence encoding a Cry2Ab *Bacillus thuringiensis* δ-endotoxin protein, wherein expression of said nucleic acid sequence by a plant cell produces said δ-endotoxin protein localized within a plastid, and wherein said expression is increased relative to a plant cell transformed to express a nucleic acid sequence encoding a Cry2Ab protein which is not localized to a plastid.

53. A morphologically normal plant comprising a nucleic acid sequence comprising in operable linkage a plant functional promoter sequence linked to a first polynucleotide sequence encoding a plastid transit peptide and a second polynucleotide sequence encoding a Cry2Ab *Bacillus thuringiensis* δ-endotoxin protein, wherein said δ-endotoxin protein is selected from the group consisting of SEQ ID NO:2 and SEQ ID NO:18, and wherein expression of said nucleic acid sequence in said plant yields said protein localized to a plastid.

54. A morphologically normal plant comprising a nucleic acid sequence comprising, in 5' to 3' order, a plant functional promoter sequence operably linked to a first polynucleotide sequence encoding a plastid transit peptide, which is linked in frame to a second polynucleotide sequence encoding a Cry2Ab *Bacillus thuringiensis* δ-endotoxin protein selected from the group consisting of SEQ ID NO:2 and SEQ ID NO:18, said second polynucleotide sequence being further linked to a plant functional 3' end transcription termination and polyadenylation sequence, wherein expression of said nucleic acid sequence in said plant yields a fusion protein comprised of an amino terminal plastid transit peptide covalently linked to said δ-endotoxin protein, and wherein said plastid transit peptide functions to localize said δ-endotoxin protein to a plastid.

55. A plant cell comprising a nucleic acid sequence comprising a plant functional promoter sequence operably linked to a first polynucleotide sequence encoding a plastid transit peptide, which is linked in frame to a second polynucleotide sequence encoding a Cry2Ab *Bacillus thuringiensis* δ-endotoxin protein wherein said second polynucleotide sequence is selected from the group consisting of SEQ ID NO:2 and SEQ ID NO:18.

56. A plant produced from the plant cell of claim 55, wherein said plant comprises said nucleic acid sequence.

57. A progeny plant produced from the plant of claim 56, wherein said progeny plant comprises said nucleic acid sequence.

58. A seed produced from the plant of claim 56 or the progeny plant of claim 134, wherein said seed comprises said nucleic acid sequence.

59. A plant produced by the method of claim 17.

60. The plant according to claim 59, wherein said increased levels of accumulation of said protein comprises from about 15 μg to about 300 μg Cry2Ab *Bacillus thuringiensis* δ-endotoxin protein per gram of one or more tissues of said first transgenic plant as set forth in Table 6.

61. The plant according to claim 59, wherein said increased levels of accumulation of said protein comprises from about 25 μg to about 200 μg Cry2Ab *Bacillus thuringiensis* δ-endotoxin protein per gram of one or more tissues of said first transgenic plant as set forth in Table 6.

62. The plant according to claim 59, wherein said increased levels of accumulation of said protein comprises from about 100 μg to about 200 μg Cry2Ab *Bacillus thuringiensis* δ-endotoxin protein per gram of one or more tissues of said first transgenic plant as set forth in Table 6.

63. The plant according to claim 59, wherein said increased levels of accumulation of said protein is about 200 μg Cry2Ab *Bacillus thuringiensis* δ-endotoxin protein per gram of one or more tissues of said first transgenic plant as set forth in Table 6.

* * * * *

UNITED STATES PATENT AND TRADEMARK OFFICE

CERTIFICATE OF CORRECTION

PATENT NO. : 6,489,542 B1 Page 1 of 1
DATED : December 3, 2002
INVENTOR(S) : Corbin et al.

It is certified that error appears in the above-identified patent and that said Letters Patent is hereby corrected as shown below:

Column 114,
Line 42, “claim 134” should read -- claim 57 --.

Signed and Sealed this

Tenth Day of January, 2006

JON W. DUDAS
*Director of the United States Patent and Trademark Office*

UNITED STATES PATENT AND TRADEMARK OFFICE

CERTIFICATE OF CORRECTION

PATENT NO. : 6,489,542 B1
APPLICATION NO. : 09/186002
DATED : December 3, 2002
INVENTOR(S) : David R. Corbin and Charles P. Romano It is certified that error appears in the above-identified patent and that said Letters Patent is hereby corrected as shown below:

In Claim 55, column 114, lines 33-34, delete "wherein said second polynucleotide sequence is".

Signed and Sealed this

Twenty-ninth Day of June, 2010

David J. Kappos
*Director of the United States Patent and Trademark Office*